(12) United States Patent
Sonesson et al.

(10) Patent No.: US 7,763,639 B2
(45) Date of Patent: Jul. 27, 2010

(54) DISUBSTITUTED PHENYLPIPERIDINES/PIPERAZINES AS MODULATORS OF DOPAMINE NEUROTRANSMISSION

(75) Inventors: Clas Sonesson, Billdal (SE); Lars Swanson, Öjersjö (SE); Nicholas Ross Waters, Göteborg (SE)

(73) Assignee: NSAB, Filial AF Neurosearch Sweden AB, Sverige, Ballerup (DK)

(*) Notice: Subject to any disclaimer, the term of this patent is extended or adjusted under 35 U.S.C. 154(b) by 0 days.

(21) Appl. No.: 11/608,313

(22) Filed: Dec. 8, 2006

(65) Prior Publication Data

US 2007/0149542 A1 Jun. 28, 2007

Related U.S. Application Data

(63) Continuation of application No. PCT/EP2005/006147, filed on Jun. 8, 2005.

(60) Provisional application No. 60/577,953, filed on Jun. 8, 2004, provisional application No. 60/637,530, filed on Dec. 20, 2004.

(30) Foreign Application Priority Data

| Jun. 8, 2004 | (SE) | ..... 0401464 |
| Dec. 20, 2004 | (SE) | ..... 0403142 |

(51) Int. Cl.
- A01N 43/40 (2006.01)
- A61K 31/445 (2006.01)
- C07D 401/00 (2006.01)

(52) U.S. Cl. .......... 514/317; 514/331; 546/192; 546/229; 546/230; 546/236; 546/237; 546/241

(58) Field of Classification Search .......... 514/317, 514/331; 546/192, 229, 230, 236, 237, 241
See application file for complete search history.

(56) References Cited

U.S. PATENT DOCUMENTS

| 3,326,916 | A | 6/1967 | Creighton et al. |
| 3,539,573 | A | 11/1970 | Schmutz et al. |
| 4,202,898 | A | 5/1980 | Depoortere |
| 4,333,942 | A | 6/1982 | Eistetter et al. |
| 4,415,736 | A | 11/1983 | Ciganek et al. |
| 4,504,660 | A | 3/1985 | Klaubert et al. |
| 5,462,947 | A | 10/1995 | Svensson et al. |
| 5,502,050 | A | 3/1996 | Gross |
| 6,175,015 | B1 | 1/2001 | Yuan et al. |
| 6,924,374 | B2 * | 8/2005 | Sonesson et al. ...... 546/192 |
| 2003/0109532 | A1 | 6/2003 | Sonesson et al. |

FOREIGN PATENT DOCUMENTS

| EP | 0060179 | 2/1982 |
| EP | 0094159 | 11/1983 |
| EP | 0369887 | 11/1989 |
| EP | 0533266 | 9/1992 |
| EP | 0533267 | 9/1992 |
| EP | 0533268 | 3/1993 |
| EP | 0 659 743 A1 * | 12/1993 |
| EP | 675118 | 4/1995 |
| EP | 0659743 | 6/1995 |
| EP | 0867183 | 10/2004 |
| FR | 1459013 | 5/1965 |
| GB | 850662 | 10/1960 |
| GB | 1560271 | 1/1977 |
| GB | 2078746 | 6/1981 |
| GB | 2083476 | 9/1981 |
| GB | 2027703 | 12/2006 |
| JP | 2000086603 | 3/2000 |
| NL | 6510107 | 2/1966 |
| WO | 8905799 | 6/1989 |
| WO | 9109594 | 7/1991 |
| WO | 9304684 | 12/1991 |
| WO | 9218475 | 10/1992 |
| WO | 9300313 | 1/1993 |
| WO | 9811068 | 3/1998 |
| WO | 0003713 | 1/2000 |
| WO | 0078728 | 12/2000 |
| WO | 01/46146 | 6/2001 |
| WO | 0146144 | 6/2001 |
| WO | 0146145 | 6/2001 |
| WO | WO 01/46146 * | 6/2001 |
| WO | 02/05819 | 1/2002 |
| WO | 02/059108 | 8/2002 |
| WO | 2004/099150 | 11/2004 |

(Continued)

OTHER PUBLICATIONS

Doggrell, The therapeutic potential of dopamine modulators on the cardiovascular and renal systems, Expert opinion on investigational drugs, (May 2002), vol. 11, No. 5, pp. 631-644.*

(Continued)

*Primary Examiner*—James O Wilson
*Assistant Examiner*—Erich A Leeser
(74) *Attorney, Agent, or Firm*—Gauthier & Connors LLP

(57) ABSTRACT

The present invention relates to compounds which have therapeutic effects against disorders in the central nervous system, and in particular new 4-(ortho, meta-disubstituted phenyl)-1-alkypiperidines and piperazines.

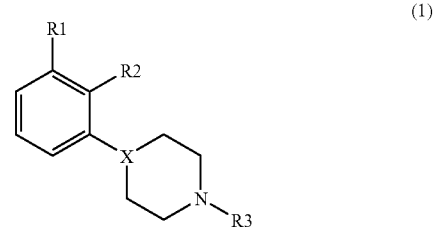

(1)

wherein $R_1$, $R_2$, $R_3$ and X are as defined.

4 Claims, 2 Drawing Sheets

FOREIGN PATENT DOCUMENTS

| WO | 2005/019215 | 3/2005 |
|---|---|---|
| WO | 2005121088 | 12/2005 |
| WO | 2005121092 | 12/2005 |
| WO | 2006039325 | 4/2006 |
| WO | 2006040155 | 4/2006 |
| WO | 2006040156 | 4/2006 |
| WO | 2007042295 | 4/2007 |
| WO | 2007065655 | 6/2007 |

OTHER PUBLICATIONS

Morita et al., "Practical Application od the Palladium-catalyzed Amination in Phenylpiperazine Synthesis: An Efficient Synthesis of a Metabolite of the Antipsychotic Agent Aripiprazole" Tetrahedron 54 (1998) pp. 4811-4818.

Manoury et al., "Synthesis and Analgesic Activities of Some (4-Substituted phenyl-1-piperazinyl) alkyl 2-Aminobenzoates and 2-Aminonicotinates" Journal of Medicinal Chemistry, 1979, vol. 22, No. 5, pp. 554-559.

Osihiro et al., "Novel Antipsychotic Agents with Dopamine Autoreceptor Agoinst Properties: Synthesis and Pharmacology of 7[4-(Phenyl-1-piperazinyl)butoxy]-3,4-dihydro-2(1H)-quinolinone Derivatives" Journal Medical Chem. 1998, 41, pp. 658-667.

Database Online: Chemical Abstracts Service, OH, XP002349551, Database accession No. 126:199585 compound with registry No. 187835-01-04 & Abstract WO 97/03986 A, Tanaka Hiroshi Kuroita, TA, Feb. 6, 1997.

Morita, Seiji et al. "Practical Application of the Palladium-catalyzed Amination in Phenylpiperazine Synthesis: An Efficient Synthesis of a Metobolite of the Antipsychotic Agent Aripiprazole" Tetrahedron 54 pp. 4811-4818; 1998.

Smaill, Jeff B. et al. "Mono- and Difunctional Nitrogen Mustard Analogues of the DNA Minor Groove Binder Pibenzimol. Synthesis, Cytotoxicity and Interaction with DNA" Anti-Cancer Drug Design. vol. 13, pp. 221-242; 1998.

Beugelmans, Rene et al. "Synthesis of 5- and 6-membered Heterocycles by a Strategy Combining SNAr and SRN1 Reactions" Bull Soc Chim Fr. vol. 132, pp. 306-313; 1995.

Egawa, Hiroshi et al. "Pyridonecarboxylic Acids as Antibacterial Agents. Part. 6 A New Synthesis of 7H-pyrido[1,2,3-de][1,4]benzoxazine Derivatives including an Antibacterical Agent, Ofloxacin" Chem. Pharm. Bull. 34(10)4098-4102; 1986.

Takai, Haruki et al. "Reaction of Spiro{4H-3,1-benzoxazine-4,4'-piperidin]-2(1 H)-one Derivatives and Related Compounds with Phosphorus Oxychloride" Chem. Pharm. Bull. 34(5)1901-1906; 1986.

Zhang, Xiuping et al. "Studies on Antimalarials. III. Synthesis and antimalarial effects of some direvatives of 2,4-diamini-6-substituted piperazinylquinazolines" Yaoxue Xuebai 16(6), pp. 415-424; 1981.

Klaubert, Dieter H. et al. "N-(Aminophenyl) Oxamic Acids and Esters as Potent, Orally Active Antiallergy Agents" J. Med. Chem. 26(6), pp. 742-748; 1981.

Self, David et al. "Cine and Tele Substitutions in the Reaction of 2,3-dinitroaniline with Secondary Amines" J.C.S. Chem. Comm. (6) pp. 281-282; 1980.

Elslager, Edward F. "Folate Antagonists. 3. 2,4-Diamino-6-(heterocyclic)quinazolines, a Novel Class of Antimetabolits with Potent Antimalarial and Antibacterial Activity" J. Med. Chem. vol. 15, No. 8, pp. 827-836; 1972.

Berberian, D.A. et al. "Comparison of Schistosomicidal Activity of Xanthenones and 4-Methyl-3-chloroanilines and Their Hydroxymethyl Analogs in Swiss Mice" J. Med. Chem. vol. 12, pp. 607-610; Jul. 1969.

Henry, David W. "A Facile Synthesis of Piperizines from Primary Amines" Journal of Heterocyclic Chemistry. vol. 3, No. 4, pp. 503-511; 1966.

Bergel, F. et al. "Synthetic Analgesics. Part I. Synthesis of Basic Benzofuran Derivatives and Certain 4-phenyl-piperidine Compounds" J. Chem. Soc. pp. 261-264; 1944.

Nacci, V. et al. "Antiblastic Substances. LII. Tylophorine Analogs. 1. Synthesis and Cytostotic and cytotoxic Activity of 4-(3,4-dimethoxphenyl)piperidine" Farmaco Ed. Scintifica. vol. 328, No. 5, pp. 399-410; 1972.

Sonesson, Clas et al. Substituted (S)-phenylpiperidines and Rigid Congeners as Preferential Dopamine Autoreceptor Antagonists: Synthesis and Structure-activity Relationships. J. Med. Chem. vol. 37, No. 17, pp. 2734-2753; 1994.

Radl, Stanislav et al. "Synthesis of Piperidine Analogs of 1-(3-Chlorophenyl)Piperazine a Well Known Serotonin Ligand" J. Heterocyclic Chem., 36, 1017; 1999.

Altomare, Cosimo et al. "Quantitative Structure-Metabolism Relationship Analyses of MAO-Mediated Toxication of 1-Methyl-4-phenyl-1,2,3,6-tetrahydropyridine and Analogues"; Chem. Res. Toxicol. vol. 5, No. 3, pp. 366-375; 1992.

Carlsson, Maria et al. "Interactions Between Glutamatergic and Monoaminergic Systems within the Basal Ganglia-Implications for Schizophrenia and Parkinson's Disease" TINS vol. 13, No. 7, pp. 272-276; 1990.

Coyle, Joseph T. et al. "Alzheimer's Disease: A Disorder of Cortical Cholinergic Innervation" Science. vol. 219, pp. 1184-1190; 1983.

Feldman et al. Principles of Neuropsychopharmacology, Chapter 17 "Mind Altering Drugs". p. 731, pp. 762-763; 1997.

Grunblatt, E. et al. "Potent Neuroprotective and Antioxidant Activity of Apopmorphine in MPTP and 6-Hydroxydopamine Induced Neurotoxicity" J Neural Transm [Suppl] vol. 55, pp. 57-70; 1999.

Grunblatt, Edna et al. "Neuroprotective Strategies in Parkinson's Disease Using Models of 6-Hydroxydopamine and MPTPa" Annals of New York Academy of Sciences. pp. 266-273; 2000.

Strange, Philip G. "Antipsychotic Drugs: Importance of Dopamine Receptors for Mechanisms of Therapeutic Actions and Side Effects" Pharmacol. Rev. vol. 53, No. 1, pp. 119-133; 2001.

Wolff, Manfred E. "Burger's Medicinal Chemistry-4th Edition, Part III",John Wiley & Sons; pp. 872-873; 1979.

Roth, Robert H. et al. "Biochemical Pharmacology of Midbrain Dopamine Neurons" Psychopharmacology: The Fourth Generation of Progress, Chapter 21; 1995.

Moore Kenneth E. et al. "Dopaminergic Neuronal Systems in the Hypothalamus" Psychopharmacology: The Fourth Generation of Progress, Chapter 22; 1995.

Le Moal, Michel. "Mesocorticolimbic Dopaminergic Neurons: Functional and Regulatory Roles" Psychopharmacology: The Fourth Generation of Progress, Chapter 25; 1995.

Seeman, Philip. "Dopamine Receptors: Clinical Correlates" Psychopharmacology: The Fourth Generation of Progress, Chapter 26; 1995.

Koob, George F. "Animal Models of Drug Addiction" Psychopharmacology: The Fourth Generation of Progress, Chapter 66; 1995.

Geyer, Mark A. et al. "Animal Models of Psychiatric Disorders" Psychopharmacology: The Fourth Generation of Progress, Chapter 68; 1995.

Willner, Paul. "Dopaminergic Mechanisms in Depression and Mania" Psychopharmacology: The Fourth Generation of Progress, Chapter 80; 1995.

Bunney, Blynn Garland et al. "Schizophrenia and Glutamate" Psychopharmacology: The Fourth Generation of Progress, Chapter 101; 1995.

Price, Lawrence H. et al. "Pharmacological Challenged in Anxiety Disorders" Psychopharmacology: The Fourth Generation of Progress, Chapter 111; 1995.

Korczyn, Amos D. "Parkinson's Disease" Psychopharmacology: The Fourth Generation of Progress, Chapter 126; 1995.

Bray, George A. "Obesity, Fat Intake, and Chronic Disease" Psychopharmacology: The Fourth Generation of Progress, Chapter 137; 1995.

Halmi, Katherine A. "Basic Biological Overview of Eating Disorders" Psychopharmacology: The Fourth Generation of Progress, Chapter 138; 1995.

Morita et al., "Practical Application of the Palladium-catalyzed Animation in Phenylpiperazine Synthesis: An Efficient Synthesis of a Metabolite of the Antipsychotic Agent Aripiprazole"; 1998 Elsevier Science Ltd., pp. 4811-4818.

Smaill et al., "Mono-and difuntional nitrogen mustard analogues of the DNA minor groove binder pibenzimol synthesis, cytotoxicity and interaction with DNA", Anti-Cancer Drug Design (1998), vol. 13, Oxford University Press; pp. 221-242.

Beugelmans et al., "Synthese d'heterocycles a 5 et 6 chainons par une strategie combinant des reactions SNAr et SRN1"; Institut de Chimie des Substances Naturelles, 1995 vol. 132; pp. 306-313.

Egawa et al, A New Synthesis of 7H-Pyrido[1,2,3-de][1,4]benzoxazine Derivatives Including an Antibacterial Agent, Ofloxacin:; Research Labortories, Osaka, Japan; 1986 vol. 34, pp. 4098-4102.

Takai et al., "Reaction of Spiro[4H-3, 1-benzoxaxine-44'-piperidin]-2(1 H)-one Derivatives and Related Compounds with Phosphorus Oxychloride"; Tokyo Research Laboratory, Tokyo, Japan; pp. 1901-1906, Chem. Pharm. Bull. 34(5), (1986).

Zhang et al., "Acta Pharmaceutica Sinica"; 1981; vol. 16, No. 6; pp. 414-424; Shanghai Institut of Pharmaceutical Industrial Research; Shanghai.

Klaubert et al., "N-(Aminohenyl)oxamic Acids and Esters as Potent, Orally Active Antiallergy Agents"; 1989 American Chemical Society; Research Division, Wyeth Laboratories Inc., Radnor, Pennsylvania; Journal of Medicinal Chemistry, vol. 24; pp. 742-748.

Self et al., "cine and tele Substitutions in the Reaction of 2,3-Dinitroaniline with Secondary Amines"; J.C.S. Chem. Comm., 1980; pp. 281-282.

Elslager et al., "Folate Antagonists. 3. 2,4-Diamino-6-(heterocyclic)quinazolines, a Novel Class of Antimetabolits with Potent Antimalarial and Antibacterial Activity"; Journal of Medicinal Chemistry; 1972 vol. 15, No. 87; pp. 826-836; Department of Chemistry, Research and Development Division, Ann Arbor, Michigan.

Berberian et al., "Comparison of Schistosomicidal Activity of Xanthenones and 4-Methyl-3-chloroanilines and Their Hydroxymethyl Analogs in Swiss Mice and Syrian Hamsters Infected with *Schistosoma mansoni*"; Sterlin-Winthrop Research Institute, Rensselaer, New York, pp. 607-610, J. Med. Chem., vol. 12, (1969).

David W. Henry, "A Facile Synthesis of Piperazines from Primary Amines (1)"; Department of Pharmaceutical Chemistry, Stanford Research Institute; Dec. 1966; pp. 503-511.

Bergel et al., Synthetic Analgesics, Part 1. Synthesis of Basic Benzofuran Derivatives and Certain 4-Phenylpiperidine Compounds; 1944; pp. 261-265.

Nacci et al., "antiblastic substances L11. Tylophorien analogs. 1. Synthesis and cytostotic and cytotoxic activity of 4-(3,4-dimethoxphenyl)piperidine"; Farmaco E. Scintifica 1972, 328, (5) pp. 399-410.

Sonesson et al., "Substituted (S)-Phenylpiperidines and Rigid Congeners as Preferential Dopamine Autoreceptor Antagonists: Synthesis and Structure-Activity Relationships"; Journal of Medicinal Chemistry, 1994 American Chemical Society; pp. 2735-2752.

Radl et al., "Synthesis of Piperidine Analogs of 1-(3-Chlorophenyl)piperazine, a Well Known Serotonin Ligand"; Research Institute for Pharmacy and Biochemistry, Prague, Czech Republic; pp. 1017-1022, J. Heterocyclic Chem., 36 (1999).

Altomare et al., Quantitative Structure-Metabolism Relationship Analyses of MAO-Medicated Toxication of 1-Methyl-4-phenyl-1,2,3,6-tetrahydropyridine and Alalogues; Chem. Res. Toxicol, 1992, vol. 5, pp. 366-375.

Carlsson et al., Interactions between glutamatergic and monoaminergic systems within the basal nanglia-implications for schizophrenia and Parkinson's disease; Department of Pharmacology, University of Goteborg, Goteborg, Sweden; 1990 Elsevier Science Publishers, vol. 13, No. 7, 1990; pp. 272-276.

Coyle et al., "Alzheimer's Disease: A Disorder of Cortical Cholinergic Innervation"; Science, vol. 219, Johns Hopkins School of Medicine, Baltimore, Maryland; pp. 1184-1190.

Feldman et al., 1993; "Mind-Altering Drugs"; Chapter 17; pp. 731, 762 and 763.

Grunblatt et al., "t neuroprotective and antioxidant activity of apomorhine in PMTP and 6-hydroxydopamine induced neurotoxicity"; Journal Neural transm. (1999) [Suppl]I pp. 57-70.

Grunblatt et al., "Neuroprotective Strategies in Parkinson's Disease Using Models of 6-Hydroxydopamine and MPTP"; Bruce Rappaport Family Research Institute and Department of Pharmacology, Haifa, Israel; pp. 262-273, Annals of New York Academy of Sciences (2000).

Philip G. Strange; "Antipsychotic Drugs: Importance of Dopamine Receptors for Mechanisms of Therapeutic Actions and Side Effects"; School of Animal and Microbial Sciences, University of Reading, Whiteknights, Reading, United Kingdom, vol. 53, No. 1; pp. 119-133, Pharmacol. Rev. (2001).

Manfred E. Wolff; "Antipsychotic Agents, 4.1 Biologic Test Methods"; Burger's Medicinal Chemistry; 4th Edition, Part III; John Wiley & Sons; 1979, pp. 872-873.

Roth et al., "Biochemical Pharmacology of Midbrain Dopamine Neurons"; Chapter 21; Yale University of Medicine; New Haven, CT; pp. 227 and 237, Psychopharmacology: The Fourth Generation of Progress, Ch. 21 (1995).

Moore et al., "Dopaminergic Neuronal Systems in the Hypothalamus"; Department of Pharmacology and Toxicology, Michigan State University East Lansing,Michigan; Chapter 22; pp. 245 and 254, Psychopharmacology: The Fourth Generation of Progress (1995).

Michel Le Moal., "Mesocorticolimbic Dopaminergic Neurons Functional and Regulatory Roles"; Universite de Bordeaux, Bordeaux, France; Chapter 25, pp. 283 and 292, Psychopharmacology: The Fourth Generation of Progress (1995).

Philip Seeman., "Dopamine Receptors Clinical Correlates"; Departmants of Pharmacology and Psychiatry, University of Toronto, Toronto, Ontario, Canada; Chapter 26, pp. 295-301, Psychopharmacology: The Fourth Generation of Progress (1995).

George F. Koon; "Animal Models of Drug Addiction"; Department of Neuropharmacology, The Scripps Research Institute, Lo Jolla, California; Chapter 66, pp. 759, 745-746, 760, 744 and 1725, Psychopharmacology: The Fourth Generation of Progress (1995).

Geyer et al., "Animal Models of Psychiatric Disorders"; Department of Neuropharmacology, The Scripps Research Institute, La Jolla, California; Chapter 68, pp. 787 and 793-795, Psychopharmacology: The Fourth Generation of Progress (1995).

Paul Willner; "Dopaminergic Mechanisms in Depression and Mania"; Department of Psychology, University College of Swansea, Wales, United Kingdom; Chapter 80; pp. 921-928, Psychopharmacology: The Fourth Generation of Progress (1995).

Bunney et al., "Schizophrenia and Glutamate"; Department of Pharmacology, University of Goteborg, Goteborg, Sweden; Chapter 101; pp. 1205 and 1207-1209, Psychopharmacology: The Fourth Generation of Progress (1995).

Price et al., "Pharmacological Challenges in Anxiety Disorders"; University of Florida College of Medicine, Gainesville, Florida; Chapter 111; pp. 1311, 1317-1318 and 1320, Psychopharmacology: The Fourth Generation of Progress (1995).

Amos D. Korczyn: "Parkinson's Disease", Tel Aviv University, Rama Aviv, Israel; Chapter 126; pp. 1479-1482, Psychopharmacology: The Fourth Generation of Progress (1995).

George A. Bray; "Obesity, Fat Intake, and Chronic Disease"; Pennington Biomedical Research Center, Louisiana State University, Baton Rouge, Louisiana; Chapter 137; pp. 1591 and 1600, Psychopharmacology: The Fourth Generation of Progress (1995).

Katherine A. Halmi; "Basic Biological Overview of Eating Disorders"; Cornell Medical Center-Westchester Division, White Plains, New York; Chapter 138; pp. 1609-1610 and 1612, Psychopharmacology: The Fourth Generation of Progress (1995).

* cited by examiner

DISUBSTITUTED PHENYLPIPERIDINES/PIPERAZINES AS MODULATORS OF DOPAMINE NEUROTRANSMISSION

PRIORITY INFORMATION

The present invention is a continuation of PCT Application No. PCT/EP2005/006147 filed on Jun. 8, 2005, which claims priority to U.S. Provisional Applications Nos. 60/577,953, filed on Jun. 8, 2004 and 60/637,530, filed on Dec. 20, 2004, and Swedish Applications Nos. SE 0401464-3, filed on Jun. 8, 2004 and SE 0403142-3, filed on Dec. 20, 2004, all of which are incorporated herein by reference in their entireties.

BACKGROUND OF THE INVENTION

1. Field of the Invention

The present invention relates to new modulators of dopamine neurotransmission, and more specifically to new 4-(ortho, meta disubstituted phenyl)-1-alkylpiperidines and piperazines, and use thereof.

2. Description of Prior Art

Dopamine is a neurotransmitter in the brain. Since this discovery, made in the 1950s, the function of dopamine in the brain has been intensely explored. To date, it is well established that dopamine is essential in several aspects of brain function including motor, cognitive, sensory, emotional and autonomous functions (e.g. regulation of appetite, body temperature, sleep). Thus, modulation of dopaminergic function may be beneficial in the treatment of a wide range of disorders affecting brain functions. In fact, drugs that act, directly or indirectly at central dopamine receptors are commonly used in the treatment of neurological and psychiatric disorders, e.g. Parkinson's disease and schizophrenia. However, currently available dopaminergic pharmaceuticals can have severe side effects. For instance, dopamine antagonists are known to induce both motor (extrapyramidal side effects; EPS) and mental side effects (e.g. anhedonia, dysphoria, and impairment of cognition), and dopaminergic agonists are known to induce dyskinesias and psychoses (Goodman and Gilman's *The Pharmacological Basis of Therapeutics*, 9th ed./McGraw-Hill, USA. Chapter 18, p 407-416, Chapter 22, p 509-512, p 515-516). An approach adopted by many researchers to improve efficacy and reduce side effects of dopaminergic pharmaceuticals, is to develop novel dopamine receptor ligands with selectivity at specific dopamine receptor subtypes or with regional selectivity. Yet another class of compounds acting through the dopamine systems of the brain are dopaminergic stabilizers, which have shown to be useful in the treatment of both neurologic and psychiatric disorders (A. Ekesbo, PhD Thesis, Uppsala University, Sweden: Functional consequences of dopaminergic degeneration; clinical and experimental studies using a novel stabilizer of dopaminergic systems: Ekesbo et al, (−)-OSU6162 inhibits levodopa-induced dyskinesias in a monkey model of Parkinson's disease, *Neuroreport*, 8, 2567, 1997; Tedroff et al. Long-lasting improvement in motor function following (−)-OSU6162 in a patient with Huntington's disease. *Neurology*, 22; 53:1605-6, 1999; Gefvert O. et al, (−)-OSU6162 induces a rapid onset of antipsychotic effect after a single dose. A double-blind placebo-controlled pilot study. *Scandinavian Society for Psychopharmacology*, 41$^{st}$ Annual Meeting, Copenhagen Denmark Nordic Journal of Psychiatry 54/2 93-94, April 2000: Carlsson et al, *Annu. Rev. Pharmacol. Toxicol.*, 41, 237, 2001; Carlsson et al. *Current Medicinal Chemistry*, 11, 267, 2004).

Another dopaminergic compound, which has been referred to as a dopamine-serotonin system stabiliser, as well as a partial DA $D_2$ receptor agonist, is the recently-launched antipsychotic compound aripiprazole (Burris et al, *Pharm. Exp. Ther, vol.* 302, 381, 2002.). Furthermore, compounds referred to as dopaminergic stabilizers have been described in WO01/46145, WO01/46146, Pettersson et al. The development of ACR16. A new class of dopaminergic stabilizers. *Society for Neuroscience* 32$^{nd}$ Annual Meeting, Abstract 2002, Vol. 28 part 1 1028, Orlando USA 2002, and Nyberg et al Efficacy and tolerability of the new dopamine stabiliser ACR16 a randomised placebo-controlled add-on study in patients with schizophrenia 12th BIENNIAL WINTER WORKSHOP ON SCHIZOPHRENIA, 7-13 Feb. 2004, Davos, Switzerland.

The typical pharmacological effects which are characteristic for dopaminergic stabilizers as described in WO01/46145, WO01/46146 and Pettersson et al. 2002 can be summarised as: 1) Increased turnover of dopamine in the terminal areas of the ascending dopaminergic projections of the mammalian brain; 2) No or only weak behavioural effects in otherwise untreated rats; and 3) Inhibition of behavioural effects induced by psychostimulants or psychotomimetic compounds in the rat. In the present invention this is referred to as a dopaminergic stabilizer profile.

This invention relates to the field of treatment of mammals suffering from CNS disorders in which the symptoms can be affected by dopaminergic functions, where the treatment comprises administering to said mammal an amount of a new type of compound, with a dopaminergic stabilizer profile.

Compounds belonging to the class of substituted 4-phenyl-N-alkyl piperidines have been reported previously. Among these compounds, some are inactive in the CNS, some display serotonergic or mixed serotonergic/dopaminergic pharmacological profiles while some are full or partial dopamine receptor agonists or antagonists with high affinity for dopamine receptors.

Costall et al. *European J. Pharm.* 31, 94, (1975) and Mewshaw et al. *Bioorg. Med. Chem. Lett.*, 8, 295, (1998) report compounds which are substituted 4-phenyl-piperazines, most of them being 2-, 3- or 4-OH phenyl substituted and displaying DA autoreceptor agonist properties. Fuller R. W. et al, *J. Pharmacol. Exp. Therapeut.* 218, 636, (1981) disclose substituted piperazines (e.g. 1-(m-trifluoro-methylphenyl)piperazine) which reportedly act as serotonin agonists and inhibit serotonin re-uptake. The comparative effects on the 5-hydroxyindole acetic acid concentration in rat brain by 1-(p-chlorophenol)-piperazine are disclosed by Fuller R. W. et al, *Res. Commun. Chem. Pathol. Pharmacol.* 29, 201, (1980). Fuller R. W. et al, *Res. Commun. Chem. Pathol. Pharmacol.* 17, 551, (1977) disclose the comparative effects on the 3,4-dihydroxy-phenylacetic acid concentration in rat brain by 1-(p-chlorophenol)-piperazine.

Boissier J. et al *Chem Abstr.* 61:10691c, disclose disubstituted piperazines. The compounds are reportedly adrenolytics, antihypertensives, potentiators of barbiturates, and depressants of the central nervous system.

A number of differently substituted piperazines have been published as ligands at 5-HT 1A receptors, for example Glennon R. A. et al *J. Med. Chem.*, 31, 1968, (1988), Mokrosz, J. et al *Arch. Pharm.* (Weinheim) 328, 143-148 (1995), and van Steen B. J., *J. Med. Chem.*, 36, 2751, (1993), Dukat M.-L., J. Med. Chem., 39, 4017, (1996).

GB2027703 discloses substituted phenyl piperazines as analgesics and psychotropic agents. GB1560271 discloses para-substituted meta-trifluoromethylphenyl piperazines and their therapeutic use in CNS and cardiovascular disorders.

U.S. Pat. No. 4,202,898 discloses substituted phenylpiperazines for the treatment of anxiety and depression. U.S. Pat. No. 3,326,916 discloses different N-alkyl substituted 4-(3-trifluoromethyl-phenyl)-piperazines for the treatment of anxiety and related psychiatric conditions. WO9811068 discloses substituted piperazines as selective dopamine D4 ligands to be used in the treatment of anxiety, de-pression, schizophrenia, obsessive ideas, Parkinson's disease, tardive dyskinesia, nausea and gastro-intestinal tract disorders.

A number of 4-phenylpiperidine derivatives are known. EP0369887 disclose substituted 4-(meta-trifluoromethylphenyl)-1,2,3,6-tetrahydropyridines for treatment of anxiety. WO00/03713 discloses a method for the treatment of schizophrenia and other dopamine system dysfunctions by using substituted 1-methyl-4-phenyl-1,2,3,6-tetrahydropyridines.

Glennon et al. (U.S. Pat. No. 6,057,371) claim a method for treating sigma receptor associated CNS disorder, comprising the administration of arylamines, including arylpiperidines, which are either unsubstituted or mono-substituted at the aryl ring. The compounds exhibit a high binding affinity with respect to the sigma receptor. WO 91/095954 states that the term "high affinity" is intended to mean a compound which exhibits an $IC_{50}$ of less than 100 nM in the assay against $^3$H-DTG described in Weber et al. Proc. Natl. Acad. Sci. (USA) 83: 8784-8788). Specifically, WO 91/095954 discloses compositions relating to "*the discovery that certain phenylalkyl-amine, aminotetraline, piperazine, piperidine and related derivatives have high binding to the sigma receptor and unexpectedly low binding for the PCP and DA receptors*" (see page 11, lines 33-36).

WO 91/095954 and WO 93/00313 both require that the compounds have a high binding affinity to the sigma receptor and do not disclose that the compounds are pharmacologically active in the absence of sigma receptor affinity. In addition, clinical studies investigating the properties of sigma receptor ligands in schizophrenic patients have not generated evidence of antipsychotic activity, nor activity in any other CNS disorder. Two of the most extensively studied selective sigma receptor antagonists, BW234U (Rimcazole) and BMY14802, have both failed in clinical studies in schizophrenic patients (Borison et al, 1991, *Psychopharmacol Bull* 27(2): 103-106; Gewirtz et al, 1994, *Neuropsychopharmacology* 10:37-40).

U.S. Pat. No. 4,415,736 discloses 4-(2,3-dimethoxy-phenyl)-1-methyl-4-piperidinol (col. 9 lines 18-19) as a synthesis intermediate In addition, it is known that compounds with formulae II (WO01/46145) and III (WO01/46146) possess dopaminergic stabilizer properties.

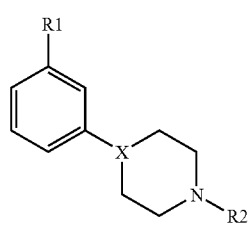

Formula II

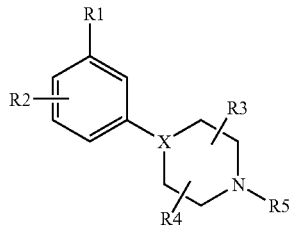

Formula III

In formula II;

X is, inter alia, CH, $R_1$ is selected from the group consisting of $OSO_2CF_3$, $OSO_2CH_3$, $SOR_3$, $SO_2R_3$, $COR_5$, CN, $NO_2$, $CONHR_3$, $CF_3$ (proviso X is CH or C) F, Cl, Br, I (wherein $R_3$ is as specified below);

$R_2$ is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_4$ (wherein $R_4$ is as specified below);

$R_3$ is selected from the group consisting of $C_1$-$C_3$ alkyl, $CF_3$, or $N(R_2)_2$;

$R_4$ is selected from the group consisting of $C_3$-$C_6$ cycloalkyl, 2-tetrahydrofurane, 3-tetra-hydrofuran.

In formula III;

X is, inter alia, CH, $R_1$ is selected from the group consisting of $OSO_2CF_3$, $OSO_2CH_3$, $SOR_7$, $SO_2R_7$, $COR_7$, CN, $NO_2$, $CONHR_3$, $CF_3$, F, Cl, Br, I (wherein $R_3$ is as specified below), 3-thiophene, 2-thiophene, 3-furane, 2-furane;

$R_2$ is selected from the group consisting of F, Cl, Br, I, CN, $CF_3$, $CH_3$, $OCH_3$, OH, $NH_2$ $R_3$ and $R_4$ are independently H or $C_1$-$C_4$ alkyl $R_5$ is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_6$;

$R_6$ is selected from the group consisting of $C_3$-$C_6$ cycloalkyl, 2-tetrahydrofurane, 3-tetrahydrofurane.

$R_7$ is selected from the group consisting of $C_1$-$C_3$ alkyl, $CF_3$ or $N(R_4)_2$ However, WO01/46145 (Formula II) only discloses mono-substitution of the aryl ring, and does not exemplify ortho-substitution. WO01/46146 does not disclose 2,3-disubstitution of the aryl ring, and it can be seen that alternative substitution patterns (e.g. 3,4-disubstitution in which the 4-position is halogen) are not as potent as the 2.3-disubstitution disclosed in the present invention.

SUMMARY OF THE INVENTION

The object of the present invention is to provide new pharmaceutically active compounds, especially useful in treatment of disorders in the central nervous system, having increased potency as dopaminergic stabilizers.

The substances according to the present invention have been found in rat tests to act preferentially on dopaminergic systems in the brain. They have effects on biochemical indices in the brain with the characteristic features of dopamine antagonists. However, the substances according to the invention show no, or only limited, inhibitory effects on spontaneous locomotion over a wide dose range. Furthermore, the substances according to the invention can induce a slight behavioural activation, in particular when baseline locomotor activity is low. However, the substances in the present invention inhibit the behavioural activation induced by psychostimulants and psychotomimetics.

DETAILED DESCRIPTION OF THE INVENTION

Figure 1:
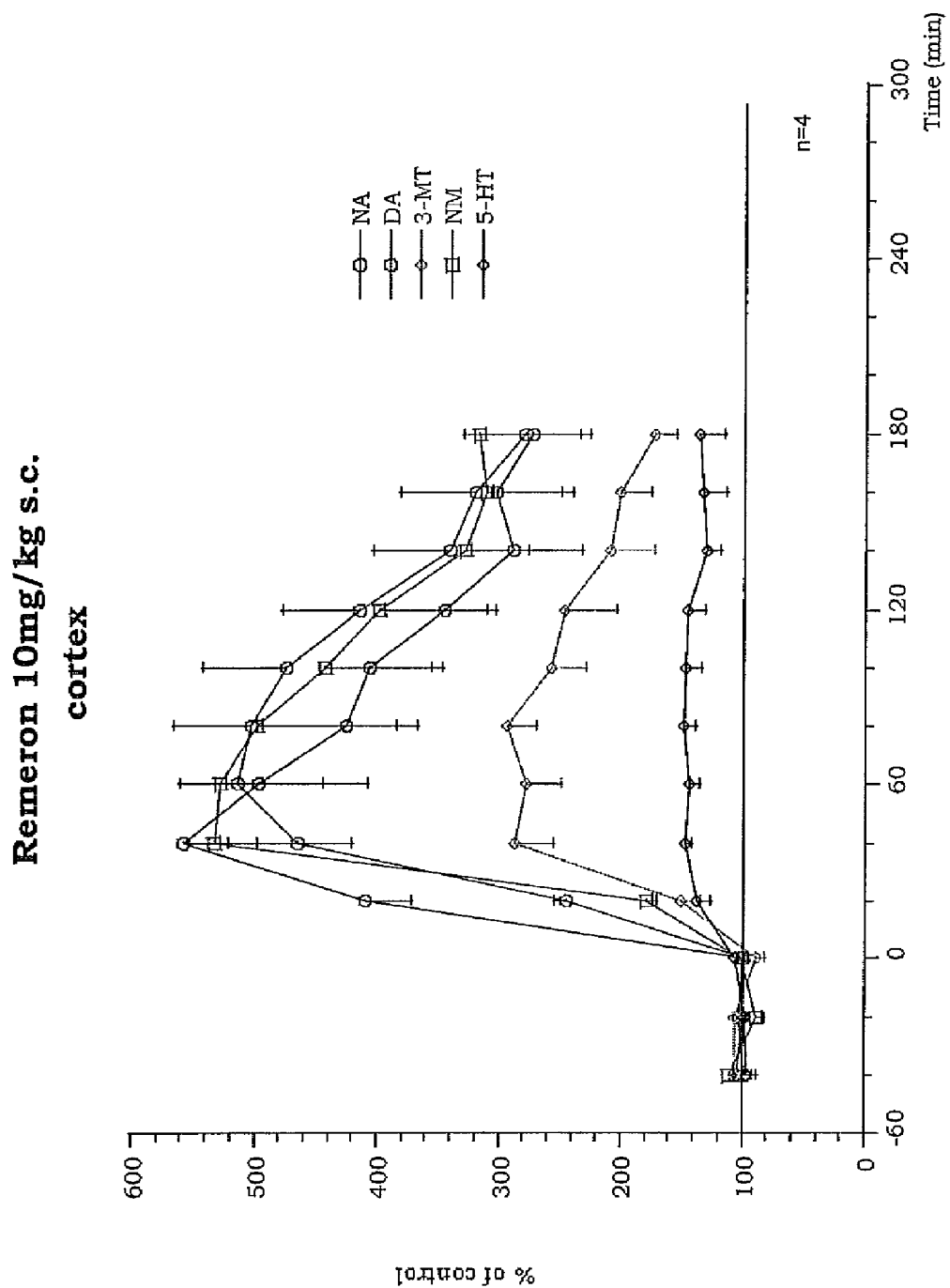
FIG. 1 is a graph showing the percent of control in relation to baseline values where Remeron is injected (s.c.) at time-point 0.

The present invention relates to new 4-(ortho, meta disubstituted phenyl)-1-alkylpiperidines and piperazines in the form of free base or pharmaceutically acceptable salts thereof, pharmaceutical compositions containing said compounds and use of said compounds in therapy.

Specifically, the invention relates to a compound of Formula 1:

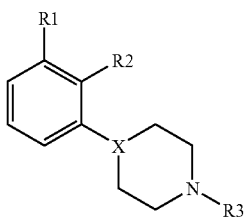

(1)

wherein:
X is N or CH
$R_1$ is selected from the group consisting of $OSO_2CF_3$, $OSO_2CH_3$, $NHSO_2CH_3$, $NHSO_2CF_3$, $SOR_4$, $SO_2R_4$, $SO_2NH_2$, $SO_2NHCH_3$, $SO_2N(CH_3)_2$, $COR_4$, CN, $OCF_3$, $SCF_3$, $OCHF_2$, $SCHF_2$, $CF_3$, F, Cl, Br, I, $NO_2$, $SF_5$, SCN, OCN, $OCOCF_3$, $SCOCF_3$, $OCOCH_3$, $SCOCH_3$, $CH(OH)CF_3$, $CH(OH)CH_3$, $CH_2NO_2$, $CH_2CN$, $CH_2SO_2CF_3$, $CH_2SO_2CH_3$, $CH_2CF_3$, $CH_2COCH_3$, $CH_2COCF_3$;

$R_2$ is selected from the group consisting of CN, $CF_3$, OH, $NH_2$, $OR_4$, F, Cl, Br, I, $CH_3$;

$R_3$ is selected from the group consisting of $C_1$-$C_4$ alkyls, allyl, $CH_2CH_2OCH_3$, $CH_2CH_2CH_2F$, $CH_2CH_2CHF_2$, $CH_2CH_2F$, $CH_2CHF_2$, $CH_2CF_3$, 3,3,3-trifluoropropyl, 4,4,4-trifluorobutyl; $CH_2CH_2OH$, $CH_2CH_2CH_2OH$, $CH_2CH(OH)CH_3$, $CH_2CH_2COCH_3$,

$R_4$ is selected from the group consisting of $C_1$-$C_3$ alkyls, $CF_3$, $CHF_2$, $CH_2F$, CN;

provided that when $R_1$ is CN, $OCF_3$, $OCHF_2$, $SCF_3$, $SCHF_2$, $CF_3$, F or Cl; X is not CH, $R_2$ is not F, Cl, Br, $CH_3$ and $R_3$ is not $C_1$-$C_3$ alkyl or allyl;

provided that when $R_1$ is $CF_3$ or CN, X is not CH, $R_2$ is not F, Cl, Br, $CH_3$ and $R_3$ is not $C_1$-$C_2$ alkyl;

and provided that when $R_1$ is $SO_2R_4$, $SO_2NH_2$, $SO_2NHCH_3$, or $SO_2N(CH_3)_2$; $R_2$ is not OH and the pharmaceutically acceptable salts thereof.

Within this group of compounds, R1 is preferably selected from the group consisting of $OSO_2CF_3$, $OSO_2CH_3$, $SO_2CH_3$, $SO_2CF_3$, $COCH_3$, $COCF_3$, CN, and $CF_3$.

As used herein the term $C_1$-$C_4$ alkyl refers to an alkyl group containing 1-4 carbon atoms in any isomeric form. The various carbon moieties are defined as follows: alkyl refers to an aliphatic hydrocarbon radical and includes branched or unbranched forms such as methyl, ethyl, n-propyl, i-propyl, n-butyl, i-butyl, s-butyl and t-butyl. Alkyl is preferably ethyl or propyl. The term "allyl" refers to the group —$CH_2$—CH=$CH_2$.

Inclusion of two substituents on the aryl ring of such compounds—one in the 2-position and the other in the 3-position—increases their potency in modulating dopamine neurotransmission. The unprecedented increase in potency of these 2,3-disubstituted compounds as compared to the mono-substituted, or the 3,4-disubstituted compounds, is illustrated in TABLE 1 and 4.

TABLE 1

Estimated $ED_{50}$ values on increase of DOPAC (3,4-dihydroxyphenylacetic acid) in the rat striatum after systemic administration of test compound. For methods and statistical calculations see the enclosed tests.

| Examples | $ED_{50}$ DOPAC* μmol/kg | Comparative Examples | $ED_{50}$ DOPAC* μmol/kg |
|---|---|---|---|
| 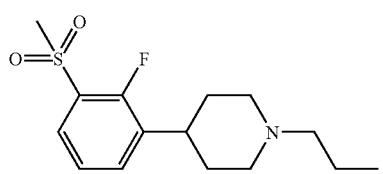<br>Example 1 | 28<br>(25–32) | 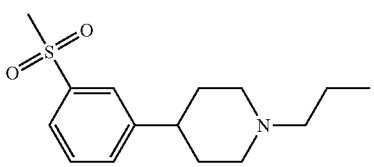<br>Example 6 of<br>WO01/46145 | 82<br>(71–102) |

TABLE 1-continued

Estimated ED$_{50}$ values on increase of DOPAC (3,4-dihydroxyphenylacetic acid) in the rat striatum after systemic administration of test compound. For methods and statistical calculations see the enclosed tests.

| Examples | ED$_{50}$ DOPAC* μmol/kg | Comparative Examples | ED$_{50}$ DOPAC* μmol/kg |
|---|---|---|---|
| 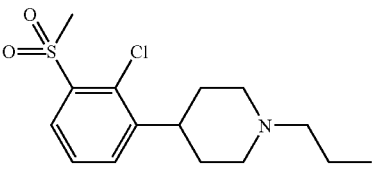 Example 3 | 9.9 (8.6–14) | | |
| 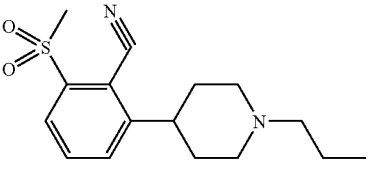 Example 15 | 28 (25–35) | | |
| 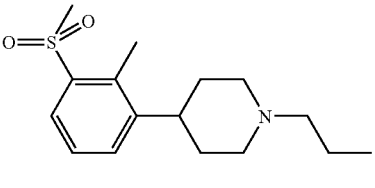 Example 4 | 58 (41–72) | | |
| 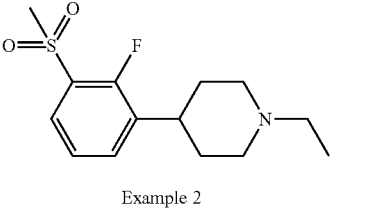 Example 2 | 68 (48–86) | 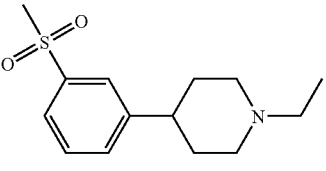 Example 12 of WO01/46145 | 154 (121–198) |
| 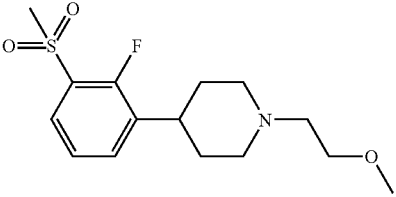 Example 17 | 84 (54–124) | 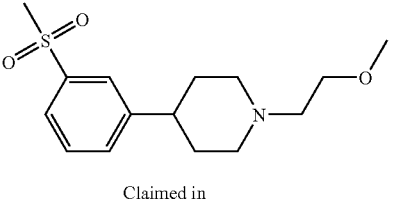 Claimed in WO01/46145 | 208 (135–359) |
| 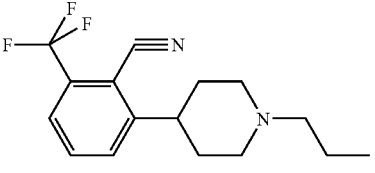 Example 7 | 9.7 (7.5–12) | 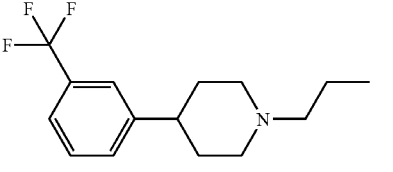 Claimed in WO01/46145 | 84 (47–110) |

TABLE 1-continued

Estimated ED$_{50}$ values on increase of DOPAC (3,4-dihydroxyphenylacetic acid) in the rat striatum after systemic adminstration of test compound. For methods and statistical calculations see the enclosed tests.

| Examples | ED$_{50}$ DOPAC* μmol/kg | Comparative Examples | ED$_{50}$ DOPAC* μmol/kg |
|---|---|---|---|
| 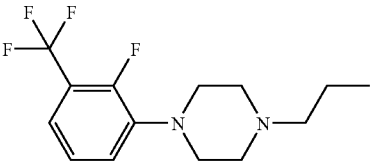<br>Example 9 | 1.9<br>(1.5–2.3) | 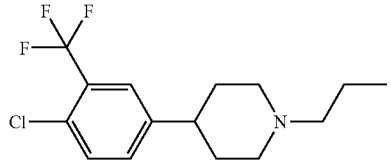<br>Example 9 of<br>WO01/46146 | 40**<br>(36–47) |
| 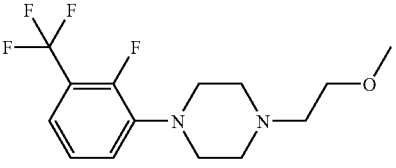<br>Example 10 | 6.2<br>(5.2–7.8) | 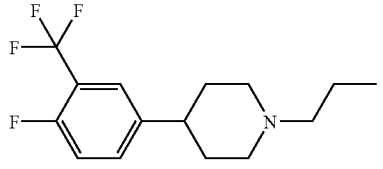<br>Example 43 of<br>WO01/46146 | 35**<br>(27–44) |
| 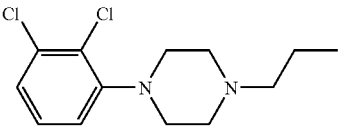<br>Example 11 | 3.5<br>(2.2–5.5) | 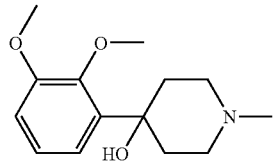<br>Example 1 and 2 in<br>U.S. Pat. No. 4,415,736 | n.d*** |
| 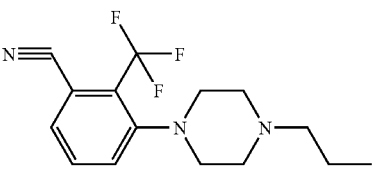<br>Example 14 | 2.4<br>(1.9–2.8) | | |
| 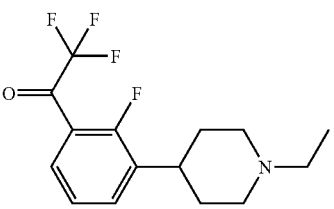 | 12<br>(9.5–14) | | |

*In ED$_{50}$ estimates the maximal effects have been limited to 350–400% of control.

**in ED$_{50}$ estimates the maximal effects have been set to 200% of control.

***N.d. Not determined; The ED$_{50}$ value was not possible to calculate because the compound did not reach sufficient high DOPAC levels after administration of 100 μmol/kg.

One aim of the present invention is to provide new compounds for therapeutic use, and more precisely compounds for modulation of dopaminergic systems in the mammalian brain, including human brain.

Another aim of the invention is to provide compounds with therapeutic effects after oral administration.

In a first embodiment, the present invention relates to 4-(ortho, meta disubstituted phenyl)-1-alkylpiperidines (i.e. compounds of Formula 1 in which X=CH):

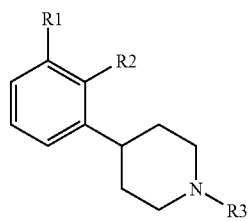

and pharmaceutically acceptable salts thereof, wherein $R_1$, $R_2$, $R_3$, and $R_4$ are as defined above.

Within this group of compounds, $R_1$ is preferably selected from the group consisting of $OSO_2CF_3$, $OSO_2CH_3$, $SO_2CH_3$, $SO_2CF_3$, $COCH_3$, $COCF_3$, CN, and $CF_3$. More preferably, $R_1$ is selected from the group consisting of $OSO_2CH_3$, $SO_2CH_3$ and $SO_2CF_3$.

In one embodiment, $R_2$ is selected from the group consisting of F (provided $R_1$ is not CN, or $CF_3$), Cl (provided $R_1$ is not CN, or $CF_3$) and OH (provided $R_1$ is not $SO_2CH_3$ or $SO_2CF_3$). In another embodiment, $R_3$ is selected from the group consisting of n-propyl and ethyl. Especially preferred compounds of the invention are those in which $R_2$ is F and $R_3$ is selected from the group consisting of n-propyl and ethyl. Further preferred compounds are those in which $R_1$ is $SO_2CH_3$, $R_2$ is F and $R_3$ is selected from the group consisting of n-propyl and ethyl.

The preferred structures are:
4-[3-fluoro-2-(trifluoromethyl)phenyl]-1-propylpiperidine
1-ethyl-4-[3-fluoro-2-(trifluoromethyl)phenyl]piperidine
4-[3-fluoro-2-(trifluoromethyl)phenyl]-1-(2-methoxyethyl)piperidine
1-allyl-4-[3-fluoro-2-(trifluoromethyl)phenyl]piperidine
2-fluoro-6-(1-propylpiperidin-4-yl)phenol
2-(1-ethylpiperidin-4-yl)-6-fluorophenol
2-fluoro-6-[1-(2-methoxyethyl)piperidin-4-yl]phenol
2-(1-allylpiperidin-4-yl)-6-fluorophenol
2-fluoro-6-(1-propylpiperidin-4-yl)aniline
2-(1-ethylpiperidin-4-yl)-6-fluoroaniline
2-fluoro-6-[1-(2-methoxyethyl)piperidin-4-yl]aniline
2-(1-allylpiperidin-4-yl)-6-fluoroaniline
2-fluoro-6-(1-propylpiperidin-4-yl)benzonitrile
2-(1-ethylpiperidin-4-yl)-6-fluorobenzonitrile
2-(1-allylpiperidin-4-yl)-6-fluorobenzonitrile
4-[2-methyl-3-(trifluoromethyl)phenyl]-1-propylpiperidine
1-allyl-4-[2-methyl-3-(trifluoromethyl)phenyl]piperidine
4-[2-fluoro-3-(trifluoromethyl)phenyl]-1-propylpiperidine
1-allyl-4-[2-fluoro-3-(trifluoromethyl)phenyl]piperidine
2-(1-propylpiperidin-4-yl)-6-(trifluoromethyl)phenol
2-(1-ethylpiperidin-4-yl)-6-(trifluoromethyl)phenol
2-[1-(2-methoxyethyl)piperidin-4-yl]-6-(trifluoromethyl)phenol
2-(1-allylpiperidin-4-yl)-6-(trifluoromethyl)phenol
2-(1-propylpiperidin-4-yl)-6-(trifluoromethyl)aniline
2-(1-ethylpiperidin-4-yl)-6-(trifluoromethyl)aniline
2-[1-(2-methoxyethyl)piperidin-4-yl]-6-(trifluoromethyl)aniline
2-(1-allylpiperidin-4-yl)-6-(trifluoromethyl)aniline
2-(1-propylpiperidin-4-yl)-6-(trifluoromethyl)benzonitrile
2-(1-ethylpiperidin-4-yl)-6-(trifluoromethyl)benzonitrile
2-(1-allylpiperidin-4-yl)-6-(trifluoromethyl)benzonitrile
4-[2-chloro-3-(trifluoromethyl)phenyl]-1-propylpiperidine
1-allyl-4-[2-chloro-3-(trifluoromethyl)phenyl]piperidine
1-[2-methyl-3-(1-propylpiperidin-4-yl)phenyl]ethanone
1-[3-(1-ethylpiperidin-4-yl)-2-methylphenyl]ethanone
1-{3-[1-(2-methoxyethyl)piperidin-4-yl]-2-methylphenyl}ethanone
1-[3-(1-allylpiperidin-4-yl)-2-methylphenyl]ethanone
1-[2-fluoro-3-(1-propylpiperidin-4-yl)phenyl]ethanone
1-[3-(1-ethylpiperidin-4-yl)-2-fluorophenyl]ethanone
1-{2-fluoro-3-[1-(2-methoxyethyl)piperidin-4-yl]phenyl}ethanone
1-[3-(1-allylpiperidin-4-yl)-2-fluorophenyl]ethanone
2-acetyl-6-(1-propylpiperidin-4-yl)benzonitrile
2-acetyl-6-(1-ethylpiperidin-4-yl)benzonitrile
2-acetyl-6-[1-(2-methoxyethyl)piperidin-4-yl]benzonitrile
2-acetyl-6-(1-allylpiperidin-4-yl)benzonitrile
1-[2-chloro-3-(1-propylpiperidin-4-yl)phenyl]ethanone
1-[2-chloro-3-(1-ethylpiperidin-4-yl)phenyl]ethanone
1-{2-chloro-3-[1-(2-methoxyethyl)piperidin-4-yl]phenyl}ethanone
1-[3-(1-allylpiperidin-4-yl)-2-chlorophenyl]ethanone
2-methyl-3-(1-propylpiperidin-4-yl)phenyl methanesulfonate
3-(1-ethylpiperidin-4-yl)-2-methylphenyl methanesulfonate
3-[1-(2-methoxyethyl)piperidin-4-yl]-2-methylphenyl methanesulfonate
3-(1-allylpiperidin-4-yl)-2-methylphenyl methanesulfonate
2-fluoro-3-(1-propylpiperidin-4-yl)phenyl methanesulfonate
3-(1-ethylpiperidin-4-yl)-2-fluorophenyl methanesulfonate
2-fluoro-3-[1-(2-methoxyethyl)piperidin-4-yl]phenyl methanesulfonate
3-(1-allylpiperidin-4-yl)-2-fluorophenyl methanesulfonate
2-cyano-3-(1-propylpiperidin-4-yl)phenyl methanesulfonate
2-cyano-3-(1-ethylpiperidin-4-yl)phenyl methanesulfonate
2-cyano-3-[1-(2-methoxyethyl)piperidin-4-yl]phenyl methanesulfonate
3-(1-allylpiperidin-4-yl)-2-cyanophenyl methanesulfonate
2-chloro-3-(1-propylpiperidin-4-yl)phenyl methanesulfonate
2-chloro-3-(1-ethylpiperidin-4-yl)phenyl methanesulfonate
2-chloro-3-[1-(2-methoxyethyl)piperidin-4-yl]phenyl methanesulfonate
3-(1-allylpiperidin-4-yl)-2-chlorophenyl methanesulfonate
4-[2-methyl-3-(methylsulfonyl)phenyl]-1-propylpiperidine
1-ethyl-4-[2-methyl-3-(methylsulfonyl)phenyl]piperidine
1-(2-methoxyethyl)-4-[2-methyl-3-(methylsulfonyl)phenyl]piperidine
1-allyl-4-[2-methyl-3-(methylsulfonyl)phenyl]piperidine
4-[2-fluoro-3-(methylsulfonyl)phenyl]-1-propylpiperidine
1-ethyl-4-[2-fluoro-3-(methylsulfonyl)phenyl]piperidine
4-[2-fluoro-3-(methylsulfonyl)phenyl]-1-(2-methoxyethyl)piperidine
1-allyl-4-[2-fluoro-3-(methylsulfonyl)phenyl]piperidine
2-(methylsulfonyl)-6-(1-propylpiperidin-4-yl)benzonitrile
2-(1-ethylpiperidin-4-yl)-6-(methylsulfonyl)benzonitrile
2-[1-(2-methoxyethyl)piperidin-4-yl]-6-(methylsulfonyl)benzonitrile
2-(1-allylpiperidin-4-yl)-6-(methylsulfonyl)benzonitrile
4-[2-chloro-3-(methylsulfonyl)phenyl]-1-propylpiperidine
4-[2-chloro-3-(methylsulfonyl)phenyl]-1-ethylpiperidine 4-[2-chloro-3-(methylsulfonyl)phenyl]-1-(2-methoxyethyl) piperidine
1-allyl-4-[2-chloro-3-(methylsulfonyl)phenyl]piperidine
4-{2-methyl-3-[(trifluoromethyl)sulfonyl]phenyl}-1-propylpiperidine
1-ethyl-4-{2-methyl-3-[(trifluoromethyl)sulfonyl]phenyl}piperidine
1-(2-methoxyethyl)-4-{2-methyl-3-[(trifluoromethyl)sulfonyl]phenyl}piperidine
1-allyl-4-{2-methyl-3-[(trifluoromethyl)sulfonyl]phenyl}piperidine
4-{2-fluoro-3-[(trifluoromethyl)sulfonyl]phenyl}-1-propylpiperidine
1-ethyl-4-{2-fluoro-3-[(trifluoromethyl)sulfonyl]phenyl}piperidine
4-{2-fluoro-3-[(trifluoromethyl)sulfonyl]phenyl}-1-(2-methoxyethyl)piperidine
1-allyl-4-{2-fluoro-3-[(trifluoromethyl)sulfonyl]phenyl}piperidine
2-(1-propylpiperidin-4-yl)-6-[(trifluoromethyl)sulfonyl]benzonitrile
2-(1-ethylpiperidin-4-yl)-6-[(trifluoromethyl)sulfonyl]benzonitrile
2-[1-(2-methoxyethyl)piperidin-4-yl]-6-[(trifluoromethyl)sulfonyl]benzonitrile
2-(1-allylpiperidin-4-yl)-6-[(trifluoromethyl)sulfonyl]benzonitrile
4-{2-chloro-3-[(trifluoromethyl)sulfonyl]phenyl}-1-propylpiperidine
4-{2-chloro-3-[(trifluoromethyl)sulfonyl]phenyl}-1-ethylpiperidine
4-{2-chloro-3-[(trifluoromethyl)sulfonyl]phenyl}-1-(2-methoxyethyl)piperidine
1-allyl-4-{2-chloro-3-[(trifluoromethyl)sulfonyl]phenyl}piperidine
2-methyl-3-(1-propylpiperidin-4-yl)phenyl trifluoromethanesulfonate
3-(1-ethylpiperidin-4-yl)-2-methylphenyl trifluoromethanesulfonate
3-[1-(2-methoxyethyl)piperidin-4-yl]-2-methylphenyl trifluoromethanesulfonate
3-(1-allylpiperidin-4-yl)-2-methylphenyl trifluoromethanesulfonate
2-fluoro-3-(1-propylpiperidin-4-yl)phenyl trifluoromethanesulfonate
3-(1-ethylpiperidin-4-yl)-2-fluorophenyl trifluoromethanesulfonate
2-fluoro-3-[1-(2-methoxyethyl)piperidin-4-yl]phenyl trifluoromethanesulfonate
3-(1-allylpiperidin-4-yl)-2-fluorophenyl trifluoromethanesulfonate
2-cyano-3-(1-propylpiperidin-4-yl)phenyl trifluoromethanesulfonate
2-cyano-3-(1-ethylpiperidin-4-yl)phenyl trifluoromethanesulfonate
2-cyano-3-[1-(2-methoxyethyl)piperidin-4-yl]phenyl trifluoromethanesulfonate
3-(1-allylpiperidin-4-yl)-2-cyanophenyl trifluoromethanesulfonate
2-chloro-3-(1-propylpiperidin-4-yl)phenyl trifluoromethanesulfonate
2-chloro-3-(1-ethylpiperidin-4-yl)phenyl trifluoromethanesulfonate
2-chloro-3-[1-(2-methoxyethyl)piperidin-4-yl]phenyl trifluoromethanesulfonate
3-(1-allylpiperidin-4-yl)-2-chlorophenyl trifluoromethanesulfonate
4-[3-chloro-2-(trifluoromethyl)phenyl]-1-propylpiperidine
4-[3-chloro-2-(trifluoromethyl)phenyl]-1-ethylpiperidine
4-[3-chloro-2-(trifluoromethyl)phenyl]-1-(2-methoxyethyl)piperidine
1-allyl-4-[3-chloro-2-(trifluoromethyl)phenyl]piperidine
2-chloro-6-(1-propylpiperidin-4-yl)phenol
2-chloro-6-(1-ethylpiperidin-4-yl)phenol
2-chloro-6-[1-(2-methoxyethyl)piperidin-4-yl]phenol
2-(1-allylpiperidin-4-yl)-6-chlorophenol
2-chloro-6-(1-propylpiperidin-4-yl)aniline
2-chloro-6-(1-ethylpiperidin-4-yl)aniline
2-chloro-6-[1-(2-methoxyethyl)piperidin-4-yl]aniline
2-(1-allylpiperidin-4-yl)-6-chloroaniline
2-chloro-6-(1-propylpiperidin-4-yl)benzonitrile
2-chloro-6-(1-ethylpiperidin-4-yl)benzonitrile
2-(1-allylpiperidin-4-yl)-6-chlorobenzonitrile
2-(difluoromethoxy)-6-(1-propylpiperidin-4-yl)phenol
2-(difluoromethoxy)-6-(1-ethylpiperidin-4-yl)phenol
2-(difluoromethoxy)-6-[1-(2-methoxyethyl)piperidin-4-yl]phenol
2-(1-allylpiperidin-4-yl)-6-(difluoromethoxy)phenol
2-(difluoromethoxy)-6-(1-propylpiperidin-4-yl)aniline
2-(difluoromethoxy)-6-(1-ethylpiperidin-4-yl)aniline
2-(difluoromethoxy)-6-[1-(2-methoxyethyl)piperidin-4-yl]aniline
2-(1-allylpiperidin-4-yl)-6-(difluoromethoxy)aniline
2-(difluoromethoxy)-6-(1-propylpiperidin-4-yl)benzonitrile
2-(difluoromethoxy)-6-(1-ethylpiperidin-4-yl)benzonitrile
2-(1-allylpiperidin-4-yl)-6-(difluoromethoxy)benzonitrile
2-(1-propylpiperidin-4-yl)-6-(trifluoromethoxy)phenol
2-(1-ethylpiperidin-4-yl)-6-(trifluoromethoxy)phenol
2-[1-(2-methoxyethyl)piperidin-4-yl]-6-(trifluoromethoxy)phenol
2-(1-allylpiperidin-4-yl)-6-(trifluoromethoxy)phenol
2-(1-propylpiperidin-4-yl)-6-(trifluoromethoxy)aniline
2-(1-ethylpiperidin-4-yl)-6-(trifluoromethoxy)aniline
2-[1-(2-methoxyethyl)piperidin-4-yl]-6-(trifluoromethoxy)aniline
2-(1-allylpiperidin-4-yl)-6-(trifluoromethoxy)aniline
2-(1-propylpiperidin-4-yl)-6-(trifluoromethoxy)benzonitrile
2-(1-ethylpiperidin-4-yl)-6-(trifluoromethoxy)benzonitrile
2-(1-allylpiperidin-4-yl)-6-(trifluoromethoxy)benzonitrile
2,2,2-trifluoro-1-[2-methyl-3-(1-propylpiperidin-4-yl)phenyl]ethanone
1-[3-(1-ethylpiperidin-4-yl)-2-methylphenyl]-2,2,2-trifluoroethanone
2,2,2-trifluoro-1-{3-[1-(2-methoxyethyl)piperidin-4-yl]-2-methylphenyl}ethanone
1-[3-(1-allylpiperidin-4-yl)-2-methylphenyl]-2,2,2-trifluoroethanone
2,2,2-trifluoro-1-[2-fluoro-3-(1-propylpiperidin-4-yl)phenyl]ethanone
1-[3-(1-ethylpiperidin-4-yl)-2-fluorophenyl]-2,2,2-trifluoroethanone
2,2,2-trifluoro-1-{2-fluoro-3-[1-(2-methoxyethyl)piperidin-4-yl]phenyl}ethanone
1-[3-(1-allylpiperidin-4-yl)-2-fluorophenyl]-2,2,2-trifluoroethanone
2-(1-propylpiperidin-4-yl)-6-(trifluoroacetyl)benzonitrile
2-(1-ethylpiperidin-4-yl)-6-(trifluoroacetyl)benzonitrile
2-[1-(2-methoxyethyl)piperidin-4-yl]-6-(trifluoroacetyl)benzonitrile
2-(1-allylpiperidin-4-yl)-6-(trifluoroacetyl)benzonitrile
1-[2-chloro-3-(1-propylpiperidin-4-yl)phenyl]-2,2,2-trifluoroethanone
1-[2-chloro-3-(1-ethylpiperidin-4-yl)phenyl]-2,2,2-trifluoroethanone 1-{2-chloro-3-[1-(2-methoxyethyl)piperidin-4-yl]phenyl}-2,2,2-trifluoroethanone
1-[3-(1-allylpiperidin-4-yl)-2-chlorophenyl]-2,2,2-trifluoroethanone
2,2,2-trifluoro-1-[2-methyl-3-(1-propylpiperidin-4-yl)phenyl]ethanol
1-[3-(1-ethylpiperidin-4-yl)-2-methylphenyl]-2,2,2-trifluoroethanol
2,2,2-trifluoro-1-{3-[1-(2-methoxyethyl)piperidin-4-yl]-2-methylphenyl}ethanol
1-[3-(1-allylpiperidin-4-yl)-2-methylphenyl]-2,2,2-trifluoroethanol
2,2,2-trifluoro-1-[2-fluoro-3-(1-propylpiperidin-4-yl)phenyl]ethanol
1-[3-(1-ethylpiperidin-4-yl)-2-fluorophenyl]-2,2,2-trifluoroethanol
2,2,2-trifluoro-1-{2-fluoro-3-[1-(2-methoxyethyl)piperidin-4-yl]phenyl}ethanol
1-[3-(1-allylpiperidin-4-yl)-2-fluorophenyl]-2,2,2-trifluoroethanol
2-(1-propylpiperidin-4-yl)-6-(2,2,2-trifluoro-1-hydroxyethyl)benzonitrile
2-(1-ethylpiperidin-4-yl)-6-(2,2,2-trifluoro-1-hydroxyethyl)benzonitrile
2-[1-(2-methoxyethyl)piperidin-4-yl]-6-(2,2,2-trifluoro-1-hydroxyethyl)benzonitrile
2-(1-allylpiperidin-4-yl)-6-(2,2,2-trifluoro-1-hydroxyethyl)benzonitrile
1-[2-chloro-3-(1-propylpiperidin-4-yl)phenyl]-2,2,2-trifluoroethanol
1-[2-chloro-3-(1-ethylpiperidin-4-yl)phenyl]-2,2,2-trifluoroethanol
1-{2-chloro-3-[1-(2-methoxyethyl)piperidin-4-yl]phenyl}-2,2,2-trifluoroethanol
1-[3-(1-allylpiperidin-4-yl)-2-chlorophenyl]-2,2,2-trifluoroethanol
2-methyl-3-(1-propylpiperidin-4-yl)benzonitrile
3-(1-allylpiperidin-4-yl)-2-methylbenzonitrile
2-fluoro-3-(1-propylpiperidin-4-yl)benzonitrile
3-(1-allylpiperidin-4-yl)-2-fluorobenzonitrile
2-hydroxy-3-(1-propylpiperidin-4-yl)benzonitrile
3-(1-ethylpiperidin-4-yl)-2-hydroxybenzonitrile
2-hydroxy-3-[1-(2-methoxyethyl)piperidin-4-yl]benzonitrile
3-(1-allylpiperidin-4-yl)-2-hydroxybenzonitrile
2-amino-3-(1-propylpiperidin-4-yl)benzonitrile
2-amino-3-(1-ethylpiperidin-4-yl)benzonitrile
2-amino-3-[1-(2-methoxyethyl)piperidin-4-yl]benzonitrile
3-(1-allylpiperidin-4-yl)-2-aminobenzonitrile
3-(1-propylpiperidin-4-yl)phthalonitrile
3-(1-ethylpiperidin-4-yl)phthalonitrile
3-(1-allylpiperidin-4-yl)phthalonitrile
2-chloro-3-(1-propylpiperidin-4-yl)benzonitrile
3-(1-allylpiperidin-4-yl)-2-chlorobenzonitrile
The most preferred structures in this class are:
2-(1-ethylpiperidin-4-yl)-6-(trifluoromethyl)phenol
1-[3-(1-ethylpiperidin-4-yl)-2-fluorophenyl]ethanone
1-[2-chloro-3-(1-ethylpiperidin-4-yl)phenyl]ethanone
3-(1-ethylpiperidin-4-yl)-2-fluorophenyl methanesulfonate
2-chloro-3-(1-ethylpiperidin-4-yl)phenyl methanesulfonate
1-ethyl-4-[2-fluoro-3-(methylsulfonyl)phenyl]piperidine
4-[2-chloro-3-(methylsulfonyl)phenyl]-1-ethylpiperidine
1-ethyl-4-{2-fluoro-3-[(trifluoromethyl)sulfonyl]phenyl}piperidine
4-{2-chloro-3-[(trifluoromethyl)sulfonyl]phenyl}-1-ethylpiperidine
3-(1-ethylpiperidin-4-yl)-2-fluorophenyl trifluoromethanesulfonate
2-chloro-3-(1-ethylpiperidin-4-yl)phenyl trifluoromethanesulfonate
1-[3-(1-ethylpiperidin-4-yl)-2-fluorophenyl]-2,2,2-trifluoroethanone
1-[2-chloro-3-(1-ethylpiperidin-4-yl)phenyl]-2,2,2-trifluoroethanone
1-[3-(1-ethylpiperidin-4-yl)-2-fluorophenyl]-2,2,2-trifluoroethanol
1-[2-chloro-3-(1-ethylpiperidin-4-yl)phenyl]-2,2,2-trifluoroethanol
3-(1-ethylpiperidin-4-yl)-2-hydroxybenzonitrile
2-(1-propylpiperidin-4-yl)-6-(trifluoromethyl)phenol
1-[2-fluoro-3-(1-propylpiperidin-4-yl)phenyl]ethanone
1-[2-chloro-3-(1-propylpiperidin-4-yl)phenyl]ethanone
2-fluoro-3-(1-propylpiperidin-4-yl)phenyl methanesulfonate
2-chloro-3-(1-propylpiperidin-4-yl)phenyl methanesulfonate
4-[2-fluoro-3-(methylsulfonyl)phenyl]-1-propylpiperidine
4-[2-chloro-3-(methylsulfonyl)phenyl]-1-propylpiperidine
4-{2-fluoro-3-[(trifluoromethyl)sulfonyl]phenyl}-1-propylpiperidine
4-{2-chloro-3-[(trifluoromethyl)sulfonyl]phenyl}-1-propylpiperidine
2-fluoro-3-(1-propylpiperidin-4-yl)phenyl trifluoromethanesulfonate
2-chloro-3-(1-propylpiperidin-4-yl)phenyl trifluoromethanesulfonate
2,2,2-trifluoro-1-[2-fluoro-3-(1-propylpiperidin-4-yl)phenyl]ethanone
1-[2-chloro-3-(1-propylpiperidin-4-yl)phenyl]2,2,2-trifluoroethanone
2,2,2-trifluoro-1-[2-fluoro-3-(1-propylpiperidin-4-yl)phenyl]ethanol
1-[2-chloro-3-(1-propylpiperidin-4-yl)phenyl]-2,2,2-trifluoroethanol
2-hydroxy-3-(1-propylpiperidin-4-yl)benzonitrile In a second embodiment, the invention relates to 4-(ortho, meta disubstituted phenyl)-1-alkylpiperazines (i.e. compounds of Formula 1 in which X=N):

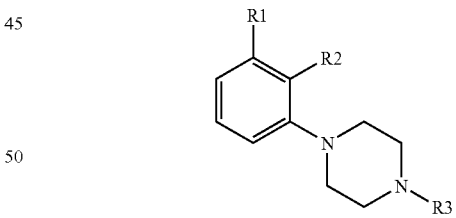

and pharmaceutically acceptable salts thereof, wherein $R_1$, $R_2$, $R_3$, and $R_4$ are as defined above.

Within this group of compounds, $R_1$ is preferably selected from the group consisting of $OSO_2CF_3$, $OSO_2CH_3$, $SO_2CH_3$, $SO_2CF_3$, $COCH_3$, $COCF_3$, CN, and $CF_3$. More preferably, $R_1$ is selected from the group consisting of $CF_3$, $SO_2CH_3$ and $SO_2CF_3$.

In one embodiment, $R_2$ is selected from the group consisting of F, Cl and OH (provided $R_1$ is not $SO_2CH_3$, $SO_2CF_3$). In another embodiment, $R_3$ is selected from the group consisting of n-propyl and ethyl. Especially preferred compounds of the invention are those in which $R_2$ is F and $R_3$ is selected from the group consisting of n-propyl and ethyl. Further preferred compounds are those in which R₁ is CF₃, R₂ is F and R₃ is selected from the group consisting of n-propyl and ethyl.

The preferred structures are:

1-(3-fluoro-2-methylphenyl)-4-propylpiperazine
1-ethyl-4-(3-fluoro-2-methylphenyl)piperazine
1-(3-fluoro-2-methylphenyl)-4-(2-methoxyethyl)piperazine
1-allyl-4-(3-fluoro-2-methylphenyl)piperazine
1-(2,3-difluorophenyl)-4-propylpiperazine
1-(2,3-difluorophenyl)-4-ethylpiperazine
1-(2,3-difluorophenyl)-4-(2-methoxyethyl)piperazine
1-allyl-4-(2,3-difluorophenyl)piperazine
1-[3-fluoro-2-(trifluoromethyl)phenyl]-4-propylpiperazine
1-ethyl-4-[3-fluoro-2-(trifluoromethyl)phenyl]piperazine
1-[3-fluoro-2-(trifluoromethyl)phenyl]-4-(2-methoxyethyl)piperazine
1-allyl-4-[3-fluoro-2-(trifluoromethyl)phenyl]piperazine
2-fluoro-6-(4-propylpiperazin-1-yl)phenol
2-(4-ethylpiperazin-1-yl)-6-fluorophenol
2-fluoro-6-[4-(2-methoxyethyl)piperazin-1-yl]phenol
2-(4-allylpiperazin-1-yl)-6-fluorophenol
2-fluoro-6-(4-propylpiperazin-1-yl)aniline
2-(4-ethylpiperazin-1-yl)-6-fluoroaniline
2-fluoro-6-[4-(2-methoxyethyl)piperazin-1-yl]aniline
2-(4-allylpiperazin-1-yl)-6-fluoroaniline
2-fluoro-6-(4-propylpiperazin-1-yl)benzonitrile
2-(4-ethylpiperazin-1-yl)-6-fluorobenzonitrile
2-fluoro-6-[4-(2-methoxyethyl)piperazin-1-yl]benzonitrile
2-(4-allylpiperazin-1-yl)-6-fluorobenzonitrile
1-(2-chloro-3-fluorophenyl)-4-propylpiperazine
1-(2-chloro-3-fluorophenyl)-4-ethylpiperazine
1-(2-chloro-3-fluorophenyl)-4-(2-methoxyethyl)piperazine
1-allyl-4-(2-chloro-3-fluorophenyl)piperazine
1-[2-methyl-3-(trifluoromethyl)phenyl]-4-propylpiperazine
1-ethyl-4-[2-methyl-3-(trifluoromethyl)phenyl]piperazine
1-(2-methoxyethyl)-4-[2-methyl-3-(trifluoromethyl)phenyl]piperazine
1-allyl-4-[2-methyl-3-(trifluoromethyl)phenyl]piperazine
1-[2-fluoro-3-(trifluoromethyl)phenyl]-4-propylpiperazine
1-ethyl-4-[2-fluoro-3-(trifluoromethyl)phenyl]piperazine
1-[2-fluoro-3-(trifluoromethyl)phenyl]-4-(2-methoxyethyl)piperazine
1-allyl-4-[2-fluoro-3-(trifluoromethyl)phenyl]piperazine
2-(4-propylpiperazin-1-yl)-6-(trifluoromethyl)phenol
2-(4-ethylpiperazin-1-yl)-6-(trifluoromethyl)phenol
2-[4-(2-methoxyethyl)piperazin-1-yl]-6-(trifluoromethyl)phenol
2-(4-allylpiperazin-1-yl)-6-(trifluoromethyl)phenol
2-(4-propylpiperazin-1-yl)-6-(trifluoromethyl)aniline
2-(4-ethylpiperazin-1-yl)-6-(trifluoromethyl)aniline
2-[4-(2-methoxyethyl)piperazin-1-yl]-6-(trifluoromethyl)aniline
2-(4-allylpiperazin-1-yl)-6-(trifluoromethyl)aniline
2-(4-propylpiperazin-1-yl)-6-(trifluoromethyl)benzonitrile
2-(4-ethylpiperazin-1-yl)-6-(trifluoromethyl)benzonitrile
2-[4-(2-methoxyethyl)piperazin-1-yl]-6-(trifluoromethyl)benzonitrile
2-(4-allylpiperazin-1-yl)-6-(trifluoromethyl)benzonitrile
1-[2-chloro-3-(trifluoromethyl)phenyl]-4-propylpiperazine
1-[2-chloro-3-(trifluoromethyl)phenyl]-4-ethylpiperazine
1-[2-chloro-3-(trifluoromethyl)phenyl]-4-(2-methoxyethyl)piperazine
1-allyl-4-[2-chloro-3-(trifluoromethyl)phenyl]piperazine
1-[2-methyl-3-(4-propylpiperazin-1-yl)phenyl]ethanone
1-[3-(4-ethylpiperazin-1-yl)-2-methylphenyl]ethanone
1-{3-[4-(2-methoxyethyl)piperazin-1-yl]-2-methylphenyl}ethanone
1-[3-(4-allylpiperazin-1-yl)-2-methylphenyl]ethanone
1-[2-fluoro-3-(4-propylpiperazin-1-yl)phenyl]ethanone
1-[3-(4-ethylpiperazin-1-yl)-2-fluorophenyl]ethanone
1-{2-fluoro-3-[4-(2-methoxyethyl)piperazin-1-yl]phenyl}ethanone
1-[3-(4-allylpiperazin-1-yl)-2-fluorophenyl]ethanone
2-acetyl-6-(4-propylpiperazin-1-yl)benzonitrile
2-acetyl-6-(4-ethylpiperazin-1-yl)benzonitrile
2-acetyl-6-[4-(2-methoxyethyl)piperazin-1-yl]benzonitrile
2-acetyl-6-(4-allylpiperazin-1-yl)benzonitrile
1-[2-chloro-3-(4-propylpiperazin-1-yl)phenyl]ethanone
1-[2-chloro-3-(4-ethylpiperazin-1-yl)phenyl]ethanone
1-{2-chloro-3-[4-(2-methoxyethyl)piperazin-1-yl]phenyl}ethanone
1-[3-(4-allylpiperazin-1-yl)-2-chlorophenyl]ethanone
2-methyl-3-(4-propylpiperazin-1-yl)phenyl methanesulfonate
3-(4-ethylpiperazin-1-yl)-2-methylphenyl methanesulfonate
3-[4-(2-methoxyethyl)piperazin-1-yl]-2-methylphenyl methanesulfonate
3-(4-allylpiperazin-1-yl)-2-methylphenyl methanesulfonate
2-fluoro-3-(4-propylpiperazin-1-yl)phenyl methanesulfonate
3-(4-ethylpiperazin-1-yl)-2-fluorophenyl methanesulfonate
2-fluoro-3-[4-(2-methoxyethyl)piperazin-1-yl]phenyl methanesulfonate
3-(4-allylpiperazin-1-yl)-2-fluorophenyl methanesulfonate
2-cyano-3-(4-propylpiperazin-1-yl)phenyl methanesulfonate
2-cyano-3-(4-ethylpiperazin-1-yl)phenyl methanesulfonate
2-cyano-3-[4-(2-methoxyethyl)piperazin-1-yl]phenyl methanesulfonate
3-(4-allylpiperazin-1-yl)-2-cyanophenyl methanesulfonate
2-chloro-3-(4-propylpiperazin-1-yl)phenyl methanesulfonate
2-chloro-3-(4-ethylpiperazin-1-yl)phenyl methanesulfonate
2-chloro-3-[4-(2-methoxyethyl)piperazin-1-yl]phenyl methanesulfonate
3-(4-allylpiperazin-1-yl)-2-chlorophenyl methanesulfonate
1-[2-methyl-3-(methylsulfonyl)phenyl]-4-propylpiperazine
1-ethyl-4-[2-methyl-3-(methylsulfonyl)phenyl]piperazine
1-(2-methoxyethyl)-4-[2-methyl-3-(methylsulfonyl)phenyl]piperazine
1-allyl-4-[2-methyl-3-(methylsulfonyl)phenyl]piperazine
1-[2-fluoro-3-(methylsulfonyl)phenyl]-4-propylpiperazine
1-ethyl-4-[2-fluoro-3-(methylsulfonyl)phenyl]piperazine
1-[2-fluoro-3-(methylsulfonyl)phenyl]-4-(2-methoxyethyl)piperazine
1-allyl-4-[2-fluoro-3-(methylsulfonyl)phenyl]piperazine
2-(methylsulfonyl)-6-(4-propylpiperazin-1-yl)benzonitrile
2-(4-ethylpiperazin-1-yl)-6-(methylsulfonyl)benzonitrile
2-[4-(2-methoxyethyl)piperazin-1-yl]-6-(methylsulfonyl)benzonitrile
2-(4-allylpiperazin-1-yl)-6-(methylsulfonyl)benzonitrile
1-[2-chloro-3-(methylsulfonyl)phenyl]-4-propylpiperazine
1-[2-chloro-3-(methylsulfonyl)phenyl]-4-ethylpiperazine
1-[2-chloro-3-(methylsulfonyl)phenyl]-4-(2-methoxyethyl)piperazine
1-allyl-4-[2-chloro-3-(methylsulfonyl)phenyl]piperazine
1-{2-methyl-3-[(trifluoromethyl)sulfonyl]phenyl}-4-propylpiperazine
1-ethyl-4-{2-methyl-3-[(trifluoromethyl)sulfonyl]phenyl}piperazine
1-(2-methoxyethyl)-4-{2-methyl-3-[(trifluoromethyl)sulfonyl]phenyl}piperazine
1-allyl-4-{2-methyl-3-[(trifluoromethyl)sulfonyl]phenyl}piperazine 1-{2-fluoro-3-[(trifluoromethyl)sulfonyl]phenyl}-4-propylpiperazine
1-ethyl-4-{2-fluoro-3-[(trifluoromethyl)sulfonyl]phenyl}piperazine
1-{2-fluoro-3-[(trifluoromethyl)sulfonyl]phenyl}-4-(2-methoxyethyl)piperazine
1-allyl-4-{2-fluoro-3-[(trifluoromethyl)sulfonyl]phenyl}piperazine
2-(4-propylpiperazin-1-yl)-6-[(trifluoromethyl)sulfonyl]benzonitrile
2-(4-ethylpiperazin-1-yl)-6-[(trifluoromethyl)sulfonyl]benzonitrile
2-[4-(2-methoxyethyl)piperazin-1-yl]-6-[(trifluoromethyl)sulfonyl]benzonitrile
2-(4-allylpiperazin-1-yl)-6-[(trifluoromethyl)sulfonyl]benzonitrile
1-{2-chloro-3-[(trifluoromethyl)sulfonyl]phenyl}-4-propylpiperazine
1-{2-chloro-3-[(trifluoromethyl)sulfonyl]phenyl}-4-ethylpiperazine
1-{2-chloro-3-[(trifluoromethyl)sulfonyl]phenyl}-4-(2-methoxyethyl)piperazine
1-allyl-4-{2-chloro-3-[(trifluoromethyl)sulfonyl]phenyl}piperazine
2-methyl-3-(4-propylpiperazin-1-yl)phenyl trifluoromethanesulfonate
3-(4-ethylpiperazin-1-yl)-2-methylphenyl trifluoromethanesulfonate
3-[4-(2-methoxyethyl)piperazin-1-yl]-2-methylphenyl trifluoromethanesulfonate
3-(4-allylpiperazin-1-yl)-2-methylphenyl trifluoromethanesulfonate
2-fluoro-3-(4-propylpiperazin-1-yl)phenyl trifluoromethanesulfonate
3-(4-ethylpiperazin-1-yl)-2-fluorophenyl trifluoromethanesulfonate
2-fluoro-3-[4-(2-methoxyethyl)piperazin-1-yl]phenyl trifluoromethanesulfonate
3-(4-allylpiperazin-1-yl)-2-fluorophenyl trifluoromethanesulfonate
2-cyano-3-(4-propylpiperazin-1-yl)phenyl trifluoromethanesulfonate
2-cyano-3-(4-ethylpiperazin-1-yl)phenyl trifluoromethanesulfonate
2-cyano-3-[4-(2-methoxyethyl)piperazin-1-yl]phenyl trifluoromethanesulfonate
3-(4-allylpiperazin-1-yl)-2-cyanophenyl trifluoromethanesulfonate
2-chloro-3-(4-propylpiperazin-1-yl)phenyl trifluoromethanesulfonate
2-chloro-3-(4-ethylpiperazin-1-yl)phenyl trifluoromethanesulfonate
2-chloro-3-[4-(2-methoxyethyl)piperazin-1-yl]phenyl trifluoromethanesulfonate
3-(4-allylpiperazin-1-yl)-2-chlorophenyl trifluoromethanesulfonate
1-(3-chloro-2-methylphenyl)-4-propylpiperazine
1-(3-chloro-2-methylphenyl)-4-ethylpiperazine
1-(3-chloro-2-methylphenyl)-4-(2-methoxyethyl)piperazine
1-allyl-4-(3-chloro-2-methylphenyl)piperazine
1-(3-chloro-2-fluorophenyl)-4-propylpiperazine
1-(3-chloro-2-fluorophenyl)-4-ethylpiperazine
1-(3-chloro-2-fluorophenyl)-4-(2-methoxyethyl)piperazine
1-allyl-4-(3-chloro-2-fluorophenyl)piperazine
1-[3-chloro-2-(trifluoromethyl)phenyl]-4-propylpiperazine
1-[3-chloro-2-(trifluoromethyl)phenyl]-4-ethylpiperazine
1-[3-chloro-2-(trifluoromethyl)phenyl]-4-(2-methoxyethyl)piperazine
1-allyl-4-[3-chloro-2-(trifluoromethyl)phenyl]piperazine
2-chloro-6-(4-propylpiperazin-1-yl)phenol
2-chloro-6-(4-ethylpiperazin-1-yl)phenol
2-chloro-6-[4-(2-methoxyethyl)piperazin-1-yl]phenol
2-(4-allylpiperazin-1-yl)-6-chlorophenol
2-chloro-6-(4-propylpiperazin-1-yl)aniline
2-chloro-6-(4-ethylpiperazin-1-yl)aniline
2-chloro-6-[4-(2-methoxyethyl)piperazin-1-yl]aniline
2-(4-allylpiperazin-1-yl)-6-chloroaniline
2-chloro-6-(4-propylpiperazin-1-yl)benzonitrile
2-chloro-6-(4-ethylpiperazin-1-yl)benzonitrile
2-chloro-6-[4-(2-methoxyethyl)piperazin-1-yl]benzonitrile
2-(4-allylpiperazin-1-yl)-6-chlorobenzonitrile
1-(2,3-dichlorophenyl)-4-propylpiperazine
1-(2,3-dichlorophenyl)-4-ethylpiperazine
1-(2,3-dichlorophenyl)-4-(2-methoxyethyl)piperazine
1-allyl-4-(2,3-dichlorophenyl)piperazine
1-[3-(difluoromethoxy)-2-methylphenyl]-4-propylpiperazine
1-[3-(difluoromethoxy)-2-methylphenyl]-4-ethylpiperazine
1-[3-(difluoromethoxy)-2-methylphenyl]-4-(2-methoxyethyl)piperazine
1-allyl-4-[3-(difluoromethoxy)-2-methylphenyl]piperazine
1-[3-(difluoromethoxy)-2-fluorophenyl]-4-propylpiperazine
1-[3-(difluoromethoxy)-2-fluorophenyl]-4-ethylpiperazine
1-[3-(difluoromethoxy)-2-fluorophenyl]-4-(2-methoxyethyl)piperazine
1-allyl-4-[3-(difluoromethoxy)-2-fluorophenyl]piperazine
2-(difluoromethoxy)-6-(4-propylpiperazin-1-yl)phenol
2-(difluoromethoxy)-6-(4-ethylpiperazin-1-yl)phenol
2-(difluoromethoxy)-6-[4-(2-methoxyethyl)piperazin-1-yl]phenol
2-(4-allylpiperazin-1-yl)-6-(difluoromethoxy)phenol
2-(difluoromethoxy)-6-(4-propylpiperazin-1-yl)aniline
2-(difluoromethoxy)-6-(4-ethylpiperazin-1-yl)aniline
2-(difluoromethoxy)-6-[4-(2-methoxyethyl)piperazin-1-yl]aniline
2-(4-allylpiperazin-1-yl)-6-(difluoromethoxy)aniline
2-(difluoromethoxy)-6-(4-propylpiperazin-1-yl)benzonitrile
2-(difluoromethoxy)-6-(4-ethylpiperazin-1-yl)benzonitrile
2-(difluoromethoxy)-6-[4-(2-methoxyethyl)piperazin-1-yl]benzonitrile
2-(4-allylpiperazin-1-yl)-6-(difluoromethoxy)benzonitrile
1-[2-chloro-3-(difluoromethoxy)phenyl]-4-propylpiperazine
1-[2-chloro-3-(difluoromethoxy)phenyl]-4-ethylpiperazine
1-[2-chloro-3-(difluoromethoxy)phenyl]-4-(2-methoxyethyl)piperazine
1-allyl-4-[2-chloro-3-(difluoromethoxy)phenyl]piperazine
1-[2-methyl-3-(trifluoromethoxy)phenyl]-4-propylpiperazine
1-ethyl-4-[2-methyl-3-(trifluoromethoxy)phenyl]piperazine
1-(2-methoxyethyl)-4-[2-methyl-3-(trifluoromethoxy)phenyl]piperazine
1-allyl-4-[2-methyl-3-(trifluoromethoxy)phenyl]piperazine
1-[2-fluoro-3-(trifluoromethoxy)phenyl]-4-propylpiperazine
1-ethyl-4-[2-fluoro-3-(trifluoromethoxy)phenyl]piperazine
1-[2-fluoro-3-(trifluoromethoxy)phenyl]-4-(2-methoxyethyl)piperazine
1-allyl-4-[2-fluoro-3-(trifluoromethoxy)phenyl]piperazine
2-(4-propylpiperazin-1-yl)-6-(trifluoromethoxy)phenol
2-(4-ethylpiperazin-1-yl)-6-(trifluoromethoxy)phenol
2-[4-(2-methoxyethyl)piperazin-1-yl]-6-(trifluoromethoxy)phenol
2-(4-allylpiperazin-1-yl)-6-(trifluoromethoxy)phenol 2-(4-propylpiperazin-1-yl)-6-(trifluoromethoxy)aniline
2-(4-ethylpiperazin-1-yl)-6-(trifluoromethoxy)aniline
2-[4-(2-methoxyethyl)piperazin-1-yl]-6-(trifluoromethoxy)aniline
2-(4-allylpiperazin-1-yl)-6-(trifluoromethoxy)aniline
2-(4-propylpiperazin-1-yl)-6-(trifluoromethoxy)benzonitrile
2-(4-ethylpiperazin-1-yl)-6-(trifluoromethoxy)benzonitrile
2-[4-(2-methoxyethyl)piperazin-1-yl]-6-(trifluoromethoxy)benzonitrile
2-(4-allylpiperazin-1-yl)-6-(trifluoromethoxy)benzonitrile
1-[2-chloro-3-(trifluoromethoxy)phenyl]-4-propylpiperazine
1-[2-chloro-3-(trifluoromethoxy)phenyl]-4-ethylpiperazine
1-[2-chloro-3-(trifluoromethoxy)phenyl]-4-(2-methoxyethyl)piperazine
1-allyl-4-[2-chloro-3-(trifluoromethoxy)phenyl]piperazine
2,2,2-trifluoro-1-[2-methyl-3-(4-propylpiperazin-1-yl)phenyl]ethanone
1-[3-(4-ethylpiperazin-1-yl)-2-methylphenyl]-2,2,2-trifluoroethanone
2,2,2-trifluoro-1-{3-[4-(2-methoxyethyl)piperazin-1-yl]-2-methylphenyl}ethanone
1-[3-(4-allylpiperazin-1-yl)-2-methylphenyl]-2,2,2-trifluoroethanone
2,2,2-trifluoro-1-[2-fluoro-3-(4-propylpiperazin-1-yl)phenyl]ethanone
1-[3-(4-ethylpiperazin-1-yl)-2-fluorophenyl]-2,2,2-trifluoroethanone
2,2,2-trifluoro-1-{2-fluoro-3-[4-(2-methoxyethyl)piperazin-1-yl]phenyl}ethanone
1-[3-(4-allylpiperazin-1-yl)-2-fluorophenyl]-2,2,2-trifluoroethanone
2-(4-propylpiperazin-1-yl)-6-(trifluoroacetyl)benzonitrile
2-(4-ethylpiperazin-1-yl)-6-(trifluoroacetyl)benzonitrile
2-[4-(2-methoxyethyl)piperazin-1-yl]-6-(trifluoroacetyl)benzonitrile
2-(4-allylpiperazin-1-yl)-6-(trifluoroacetyl)benzonitrile
1-[2-chloro-3-(4-propylpiperazin-1-yl)phenyl]-2,2,2-trifluoroethanone
1-[2-chloro-3-(4-ethylpiperazin-1-yl)phenyl]-2,2,2-trifluoroethanone
1-{2-chloro-3-[4-(2-methoxyethyl)piperazin-1-yl]phenyl}-2,2,2-trifluoroethanone
1-[3-(4-allylpiperazin-1-yl)-2-chlorophenyl]-2,2,2-trifluoroethanone
2,2,2-trifluoro-1-[2-methyl-3-(4-propylpiperazin-1-yl)phenyl]ethanol
1-[3-(4-ethylpiperazin-1-yl)-2-methylphenyl]-2,2,2-trifluoroethanol
2,2,2-trifluoro-1-{3-[4-(2-methoxyethyl)piperazin-1-yl]-2-methylphenyl}ethanol
1-[3-(4-allylpiperazin-1-yl)-2-methylphenyl]-2,2,2-trifluoroethanol
2,2,2-trifluoro-1-[2-fluoro-3-(4-propylpiperazin-1-yl)phenyl]ethanol
1-[3-(4-ethylpiperazin-1-yl)-2-fluorophenyl]-2,2,2-trifluoroethanol
2,2,2-trifluoro-1-{2-fluoro-3-[4-(2-methoxyethyl)piperazin-1-yl]phenyl}ethanol
1-[3-(4-allylpiperazin-1-yl)-2-fluorophenyl]-2,2,2-trifluoroethanol
2-(4-propylpiperazin-1-yl)-6-(2,2,2-trifluoro-1-hydroxyethyl)benzonitrile
2-(4-ethylpiperazin-1-yl)-6-(2,2,2-trifluoro-1-hydroxyethyl)benzonitrile
2-[4-(2-methoxyethyl)piperazin-1-yl]-6-(2,2,2-trifluoro-1-hydroxyethyl)benzonitrile
2-(4-allylpiperazin-1-yl)-6-(2,2,2-trifluoro-1-hydroxyethyl)benzonitrile
1-[2-chloro-3-(4-propylpiperazin-1-yl)phenyl]-2,2,2-trifluoroethanol
1-[2-chloro-3-(4-ethylpiperazin-1-yl)phenyl]-2,2,2-trifluoroethanol
1-{2-chloro-3-[4-(2-methoxyethyl)piperazin-1-yl]phenyl}-2,2,2-trifluoroethanol
1-[3-(4-allylpiperazin-1-yl)-2-chlorophenyl]-2,2,2-trifluoroethanol
2-methyl-3-(4-propylpiperazin-1-yl)benzonitrile
3-(4-ethylpiperazin-1-yl)-2-methylbenzonitrile
3-[4-(2-methoxyethyl)piperazin-1-yl]-2-methylbenzonitrile
3-(4-allylpiperazin-1-yl)-2-methylbenzonitrile
2-fluoro-3-(4-propylpiperazin-1-yl)benzonitrile
3-(4-ethylpiperazin-1-yl)-2-fluorobenzonitrile
2-fluoro-3-[4-(2-methoxyethyl)piperazin-1-yl]benzonitrile
3-(4-allylpiperazin-1-yl)-2-fluorobenzonitrile
2-hydroxy-3-(4-propylpiperazin-1-yl)benzonitrile
3-(4-ethylpiperazin-1-yl)-2-hydroxybenzonitrile
2-hydroxy-3-[4-(2-methoxyethyl)piperazin-1-yl]benzonitrile
3-(4-allylpiperazin-1-yl)-2-hydroxybenzonitrile
2-amino-3-(4-propylpiperazin-1-yl)benzonitrile
2-amino-3-(4-ethylpiperazin-1-yl)benzonitrile
2-amino-3-[4-(2-methoxyethyl)piperazin-1-yl]benzonitrile
3-(4-allylpiperazin-1-yl)-2-aminobenzonitrile
3-(4-propylpiperazin-1-yl)phthalonitrile
3-(4-ethylpiperazin-1-yl)phthalonitrile
3-[4-(2-methoxyethyl)piperazin-1-yl]phthalonitrile
3-(4-allylpiperazin-1-yl)phthalonitrile
2-chloro-3-(4-propylpiperazin-1-yl)benzonitrile
2-chloro-3-(4-ethylpiperazin-1-yl)benzonitrile
2-chloro-3-[4-(2-methoxyethyl)piperazin-1-yl]benzonitrile
3-(4-allylpiperazin-1-yl)-2-chlorobenzonitrile The most preferred structures within this class are:
1-[2-fluoro-3-(trifluoromethyl)phenyl]-4-propylpiperazine
1-ethyl-4-[2-fluoro-3-(trifluoromethyl)phenyl]piperazine
1-[2-fluoro-3-(trifluoromethyl)phenyl]-4-(2-methoxyethyl)piperazine
1-allyl-4-[2-fluoro-3-(trifluoromethyl)phenyl]piperazine
1-[2-chloro-3-(trifluoromethyl)phenyl]-4-propylpiperazine
1-[2-chloro-3-(trifluoromethyl)phenyl]-4-ethylpiperazine
1-[2-chloro-3-(trifluoromethyl)phenyl]-4-(2-methoxyethyl)piperazine
1-allyl-4-[2-chloro-3-(trifluoromethyl)phenyl]piperazine
1-[2-fluoro-3-(methylsulfonyl)phenyl]-4-propylpiperazine
1-ethyl-4-[2-fluoro-3-(methylsulfonyl)phenyl]piperazine
1-[2-fluoro-3-(methylsulfonyl)phenyl]-4-(2-methoxyethyl)piperazine
1-allyl-4-[2-fluoro-3-(methylsulfonyl)phenyl]piperazine
1-[2-chloro-3-(methylsulfonyl)phenyl]-4-propylpiperazine
1-[2-chloro-3-(methylsulfonyl)phenyl]-4-ethylpiperazine
1-[2-chloro-3-(methylsulfonyl)phenyl]-4-(2-methoxyethyl)piperazine
1-allyl-4-[2-chloro-3-(methylsulfonyl)phenyl]piperazine
1-{2-fluoro-3-[(trifluoromethyl)sulfonyl]phenyl}-4-propylpiperazine
1-ethyl-4-{2-fluoro-3-[(trifluoromethyl)sulfonyl]phenyl}piperazine
1-{2-fluoro-3-[(trifluoromethyl)sulfonyl]phenyl}-4-(2-methoxyethyl)piperazine
1-allyl-4-{2-fluoro-3-[(trifluoromethyl)sulfonyl]phenyl}piperazine
1-{2-chloro-3-[(trifluoromethyl)sulfonyl]phenyl}-4-propylpiperazine 1-{2-chloro-3-[(trifluoromethyl)sulfonyl]phenyl}-4-ethylpiperazine 1-{2-chloro-3-[(trifluoromethyl)sulfonyl]phenyl}-4-(2-methoxyethyl)piperazine 1-allyl-4-{2-chloro-3-[(trifluoromethyl)sulfonyl]phenyl}piperazine The volume of the substituents of the compounds of Formula 1 is relevant. Particularly, it has been found that if the calculated van der Waals volume of $R_2$ is larger than 27 Å$^3$, then the total van der Waals volume of $R_1$ and $R_2$ ($R_1+R_2$) should not be larger than 70 Å$^3$. One example that was found to be inactive is: 4-[3-(methylsulfonyl)-2-(trifluoromethyl)phenyl]-1-propylpiperidine, in which the total volume is 71 Å$^3$ and the volume for R2 is larger than 27.

The polarity of the compounds of Formula 1 has also proved to be relevant so as to obtain compounds having high activity. In particular, it has been found that the calculated octanol/water partitioning constant value should be greater than 0.6, preferably greater than 0.9.

The present invention also relates to intermediate compounds which are used in the synthesis of compounds of Formula 1. One such intermediate compound has the structure:

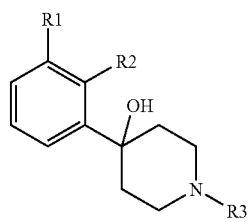

wherein $R_1$, $R_2$, $R_3$, and $R_4$ are as defined above.

Within this group of compounds, $R_1$ is preferably selected from the group consisting of $OSO_2CF_3$, $OSO_2CH_3$, $SO_2CH_3$, $SO_2CF_3$, $COCH_3$, $COCF_3$, $CN$, and $CF_3$. More preferably, $R_1$ is selected from the group consisting of $OSO_2CH_3$, $SO_2CH_3$ and $SO_2CF_3$.

In one embodiment, $R_2$ is selected from the group consisting of F, Cl and OH (provided $R_1$ is not $SO_2CH_3$, $SO_2CF_3$). In another embodiment, $R_3$ is selected from the group consisting of n-propyl and ethyl. Especially preferred compounds of the invention are those in which $R_2$ is F and $R_3$ is selected from the group consisting of n-propyl and ethyl. Further preferred compounds are those in which $R_1$ is $SO_2CH_3$, $R_2$ is F and $R_3$ is selected from the group consisting of n-propyl and ethyl.

Another intermediate in the synthesis of compounds with Formula 1 has the formula

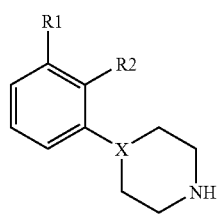

in which X, $R_1$, $R_2$, and $R_4$ are as defined above.

Such intermediate compounds of interest are those in which $R_1$ is selected from the group consisting of $OSO_2CF_3$, $OSO_2CH_3$, $SO_2CH_3$, $SO_2CF_3$, $COCH_3$, $COCF_3$, $CN$ and $CF_3$. Further such intermediate compounds of interest are those in which $R_1$ is selected from the group consisting of $OSO_2CH_3$, $SO_2CH_3$ and $SO_2CF_3$. Additionally, $R_2$ may be selected from the group consisting of F, and Cl and OH (provided $R_1$ is not $SO_2CH_3$, $SO_2CF_3$).

The invention also relates to the use of a compound of Formula 1 for the manufacture of a pharmaceutical composition for treatment of a disorder of the central nervous system, and to the pharmaceutical compositions themselves. The present invention relates to a method for treating disorders of the central nervous system, by administrating a therapeutically active amount of a compound according to FIG. 1 to a mammal, including a human being, suffering from such a disorder. The present invention also relates to a method for treating any disorder named herein, by administrating a therapeutically active amount of a compound according to FIG. 1 to a mammal, including a human being, suffering from such a disorder.

The compounds according to the present invention possess dopamine-modulating properties and both they and their pharmaceutical compositions are useful in treating numerous central nervous system disorders, including both psychiatric and neurological disorders. Particularly, the compounds and their pharmaceutical compositions may be used in the treatment of CNS disorders were the dopaminergic system is dysfunctional due to direct or indirect causes.

The compounds and compositions according to the invention can be used to improve all forms of psychosis, including schizophrenia and schizophreniform and bipolar disorders as well as drug induced psychotic disorders. Iatrogenic and non-iatrogenic psychoses and hallucinoses may also be treated.

Mood and anxiety disorders, depression and obsessive-compulsive disease may also be treated with the compounds and compositions according to the invention.

Compounds with modulating effects on dopaminergic systems may also be used to improve motor and cognitive functions and in the treatment of emotional disturbances related to ageing, neurodegenerative (e.g. dementia and age-related cognitive impairment) and developmental disorders (such as Autism spectrum disorders, ADHD, Cerebral Palsy, Gilles de la Tourette's syndrome) as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds, environmental toxins The compounds and pharmaceutical compositions according to the invention may also be used in behavioural disorders usually first diagnosed in infancy, childhood, or adolescence as well as in impulse control disorders.

They can also be used for treating substance abuse disorders as well as disorders characterized by misuse of food. They are further useful for treatment of a condition selected from the group consisting of sleep disorders, sexual disorders, eating disorders, obesitas, and headaches and other pains in conditions characterized by increased muscular tone.

Neurological indications include the use of the compounds and their pharmaceutical compositions to improve mental and motor function in Parkinson's disease, and in related parkinsonian syndromes, dyskinesias (including L-DOPA induced dyskinesias) and dystonias. They may also be used to ameliorate tics and tremor of different origins. Moreover, they may be used to relieve pain in conditions characterized by increased muscle tone.

They can also be used in the treatment of Huntington's disease and other movement disorders as well as movement disorders induced by drugs. Restless legs and related disorders as well as narcolepsy may also be treated with compounds included according to the invention.

The compounds and their pharmaceutical compositions according to the present invention can be used for the treatment of Alzheimer's disease or related dementia disorders.

The compounds according to the present invention have been shown to display dopaminergic stabilizer profile with improved potency. They have effects on biochemical indices in the brain with the characteristic features of dopamine antagonists, e.g. producing increases in concentrations of dopamine metabolites.

The compounds of this invention show no, or only limited effects on spontaneous locomotion over a wide dose range (Table 2).

TABLE 2

Effects of compounds from the present invention on Locomotor activity in drug-naive rats.
The animals were placed in the motility meters immediately after drug administration and locomotor activity was recorded for 60 minutes (counts/60 min ± SEM).

|  | Control group | 11 μmol/kg | 33 μmol/kg | 100 μmol/fkg |
|---|---|---|---|---|
| Example 1 | 7049 ± 1230 | 9500 ± 617 | 7371 ± 992 | 8103 ± 1047 |
| Example 2 | 8545 ± 1596 | 13113 ± 1795 | 12744 ± 1291 | 12530 ± 2577 |
| Example 3 | 7725 ± 1354 | 6078 ± 605 | 3023 ± 246 | 1327 ± 299 |
| Example 4 | 9485 ± 2066 | 8972 ± 1124 | 9023 ± 1415 | 4473 ± 924 |
| Example 7 | 9224 ± 1175 | 7008 ± 700 | 4694 ± 986 | 2829 ± 358 |

TABLE 2-continued

Effects of compounds from the present invention on Locomotor activity in drug-naive rats. The animals were placed in the motility meters immediately after drug administration and locomotor activity was recorded for 60 minutes (counts/60 min ± SEM).

|  | Control group | 11 µmol/kg | 33 µmol/kg | 100 µmol/fkg |
|---|---|---|---|---|
| 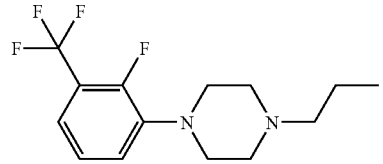⏎Example 9 | 8246 ± 698 | 3721 ± 242 | 3518 ± 435 | 4265 ± 758 |
| 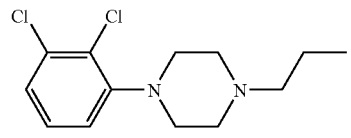⏎Example 11 | 11346 ± 2133 | 5149 ± 374 | 4032 ± 828 | 3299 ± 637 |

In some cases, in particular when the baseline activity is low, they can induce a slight behavioural activation (Table 3). The behavioural activation is limited, not reaching the profound increases in activity induced by direct or indirect dopaminergic agonists.

TABLE 3

Effects of compounds from the present invention on Locomotor activity in drug-naive rats. The animals were placed in the motility meters immediately after drug administration and locomotor activity was recorded between 30 and 60 minutes (counts/30 min ± SEM). During this period the animals have habituated to their environment and therefore the locomotor activity is low in the control group.

|  | Control group | 11 µmol/kg | 33 µmol/kg | 100 µmol/kg |
|---|---|---|---|---|
| 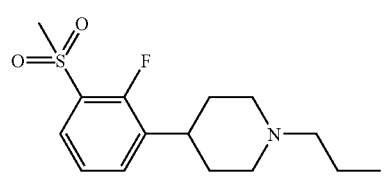⏎Example 1 | 241 ± 131 | 1708 ± 922 | 1337 ± 141 (P = 0.001) | 1365 ± 460 (P = 0.057) |
| 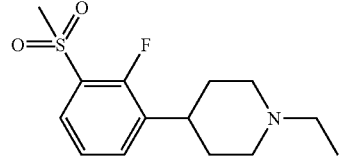⏎Example 2 | 705 ± 581 | 2254 ± 804 | 2499 ± 766 (P = 0.1) | 2418 ± 703 (P = 0.1) |

TABLE 3-continued

Effects of compounds from the present invention on Locomotor activity in drug-naive rats. The animals were placed in the motility meters immediately after drug administration and locomotor activity was recorded between 30 and 60 minutes (counts/30 min ± SEM). During this period the animals have habituated to their environment and therefore the locomotor activity is low in the control group.

| | Control group | 11 μmol/kg | 33 μmol/kg | 100 μmol/kg |
|---|---|---|---|---|
| 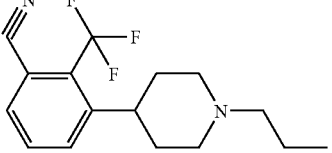<br>Example 13 | 400 ± 175 | 960 ± 710 | 2870 ± 613<br>(P = 0.008) | 4366 ± 1389<br>(P = 0.030) |
| 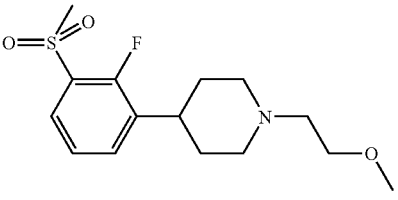<br>Example 17 | 559 ± 252 | 1836 ± 504<br>(P = 0.064) | 1258 ± 623 | 1085 ± 211 |

On the other hand, the preferred substances reduce the increase in activity induced by direct or indirect dopaminergic agonists, i.e. d-amphetamine and congeners (Table 4). The compounds of the invention were also found to be more potent than the comparative examples from WO01/145, WO01/146 and U.S. Pat. No. 4,415,736 (which were found to be inactive).

TABLE 4

Effects of compounds in the present invention on reduction of amphetamine-induced hyper-locomotion. Comparative examples from prior art is also included. For methods and statistical calculations see the enclosed tests

| Examples | $ED_{50}$ μmol/kg | Comparative Examples | $ED_{50}$ μmol/kg |
|---|---|---|---|
| 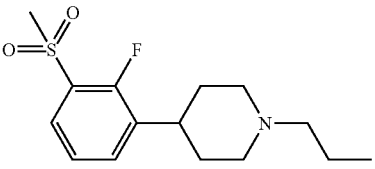<br>Example 1 | 16<br>(8.8–31) | 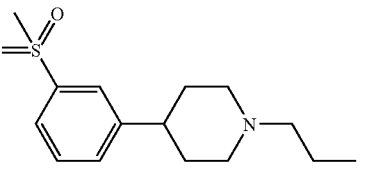<br>Example 6 of<br>WO01/46145 | 52<br>(35–76) |
| 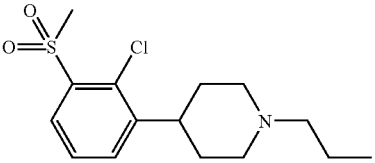<br>Example 3 | 11<br>(8.2–17) | | |

TABLE 4-continued

Effects of compounds in the present invention on reduction of amphetamine-induced hyperlocomotion. Comparative examples from prior art is also included. For methods and statistical calculations see the enclosed tests

| Examples | $ED_{50}$ μmol/kg | Comparative Examples | $ED_{50}$ μmol/kg |
|---|---|---|---|
| Example 2 | 28 (19–56) | Example 12 of WO01/46145 | 86 (34–137) |
| Example 33 | 19 (8.7–38) | | |
| Example 29 | 16 (8.7–26) | Example 43 of WO01/46146 | 30 (21–44) |
| Example 32 | 12.4 (8.3–17) | | |
| Example 9 | 1.4 (0.4–2.6) | Example 9 of WO01/46146 | 34 (12–54) |
| Example 31 | 6.2 (2.9–10) | Example 1 and 2 in U.S. Pat. No. 4,415,736 | Inactive |

Thus, the compounds of this invention show a dopaminergic stabilizer profile (seen in Table 1-4) with improved potency (seen in Table 1 and 4). Given the involvement of dopamine in a large variety of CNS functions and the clinical shortcomings of presently available pharmaceuticals acting on dopamine systems, the novel class of dopaminergic modulators presented in this invention may prove superior to presently known dopaminergic compounds in the treatment of several disorders related to dysfunctions of the CNS, in terms of efficacy as well as side effects.

Compounds in the present invention have also been shown to display high metabolic stability in rat liver microsomes measured as turnover at 15 minutes (Example 1: 3%, Example 2: 1%, Example 4: 4%, Example 7: 22%, Example 8: 49%) and high oral bioavailability in rat, exemplified by Example 1 (about 100%), Example 2 (87%), Example 7 (29%).

These compounds are thus suitable for the preparation of orally-administered pharmaceuticals. There is no guidance in the prior art how to obtain compounds with the dopamine stabilizer profile (Table 1 to Table 4) with improved potency on dopamine systems in the brain.

Pharmacology

Evidence is available that dopaminergic neurotransmission in the CNS is disturbed in psychiatric and neurological diseases. In many instances, for example in schizophrenia, Parkinson's disease, Huntington disease, bipolar disorder and in dementia pharmacotherapies based on antagonism or agonism at dopamine receptors are useful, but not optimal. In recent years many efforts have been made in finding novel and selective compounds for dopamine receptor subtypes (D1, D2, D3, D4, D5) with the aim to improve efficacy and reduce side effects.

The present invention offers another principle for novel therapeutics based on interactions with the dopamine system. The invention provides compounds having, as their major feature, stabilizing effects on the dopaminergic system in the brain.

Description of Animal Models Used in the Invention

The compounds according to the invention have effects on brain neurochemistry similar to antagonists at dopamine D2 receptors (i.e. dose-dependent increases of the dopamine metabolite DOPAC, in cortical, striatal and limbic brain regions). The compounds according to the invention show no, or only limited inhibitory, effects on spontaneous locomotion. Under certain conditions they can induce a behavioural activation. The behavioural activation is limited, not reaching the profound increases in activity induced by direct or indirect dopamine receptor agonists. However, the preferred substances reduce the increase in activity induced by the indirect dopaminergic agonist d-amphetamine. The increase in activity after treatment with d-amphetamine is a standard model of hyperdopaminergia (Table 4). In this model, dopaminergic neurotransmission is increased by systemic administration of d-amphetamine at a dose that is sufficiently high to produce a large increase in locomotor activity. The ability of a compound to antagonize this hyperactivity reflects anti-dopaminergic properties, which are part of the dopaminergic stabiliser profile. Furthermore, antagonism of d-amphetamine induced hyperactivity is widely used as a standard assay of antipsychotic activity (see *Psychopharmacology* 4th *Generation of progress* Chapter 68, p 793-795).

Another animal model of antipsychotic activity is based on administration of the glutamate antagonist MK-801. Glutamate antagonists (i.e. NMDA antagonists), can induce psychoses in man (see *Psychopharmacology*, 4th *Generation of progress* Chapter 101, p. 1205 and 1207) and induce behavioural aberrations in animals. Thus, the ability of a drug to affect schizophrenia and psychotic states can be measured using behavioural models based on experimentally-induced hypoglutamatergic states. In this study the NMDA antagonist MK-801 (0.7 mg/kg i.p.) was used to create a hypoglutamatergic state where the rats display abnormal, hyperactive behaviour. Compounds in the present invention dose-dependently reverse the behavioural aberration induced by MK-801 (see Table 5).

It is known that the dopaminergic systems of the brain interact strongly with other transmitter systems (see *Psychopharmacology*, 4th *Generation of progress*, Chapter 101, pages 1208-1209). Such interactions can explain the powerful effects of dopaminergic stabilizers on the behavioural aberrations induced by the glutamate antagonist MK-801 although these aberrations are not primarily based on or caused by changes in dopaminergic transmission.

TABLE 5

Effects of compounds from the present invention on Locomotor activity in MK-801 pre-treated rats (0.7 mg/kg I.p. 90 minutes before test compound). The animals were placed in the motility meters immediately after test compound administration and locomotor activity was recorded between 30 and 60 minutes after administration (counts/30 mm ± SEM)

|  | Control group | MK-801 0.7 mg/kg i.p | MK + example 33 μmol/kg |
|---|---|---|---|
|  | 578 ± 510 | 51333 ± 2148 | 29636 ± 10019 (P = 0.08) |

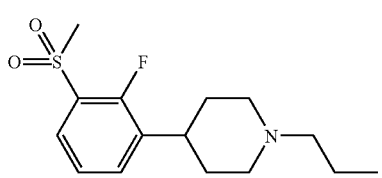

Example 1

TABLE 5-continued

Effects of compounds from the present invention on Locomotor activity in MK-801 pre-treated rats (0.7 mg/kg I.p. 90 minutes before test compound). The animals were placed in the motility meters immediately after test compound administration and locomotor activity was recorded between 30 and 60 minutes after administration (counts/30 mm ± SEM)

| | Control group | MK-801 0.7 mg/kg i.p | MK + example 33 µmol/kg |
|---|---|---|---|
| 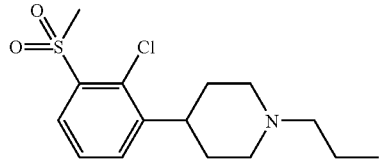  Example 3 | 369 ± 330 | 25899 ± 9703 | [1]4911 ± 2953[1] (P = 0.08) |
| 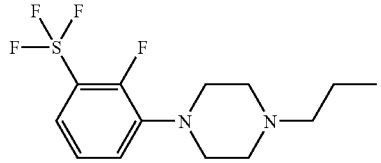  Example 9 | 47 ± 21 | 45714 ± 7127 | [1]5916 ± 1918[2] (P = 0.002) |

[1] 100 µmol/kg
[2] 11 µmol/kg

Therapeutic Use of Dopaminergic Stabilizers

The claimed invention provides compounds having, as their major feature, stabilizing effects on the dopaminergic system in the brain. These compounds are useful for treating CNS disorders in which the symptoms can be affected by dopaminergic functions. In support of this assertion, please see the following references:

In support of schizophrenia and psychosis, Applicants refer to *Psychopharmacology 4th Generation of progress* Chapter 26, p. 295-301;

Parkinson's disease (*Psychopharmacology 4th Generation of progress* Chapter 26, p 295, Chapter 1479-1482);

Anxiety disorders (*Psychopharmacology 4th Generation of progress* Chapter 21, p. 227 and 237, Chapter 111, p. 1317-1318 and 1320);

Mood disorders (*Psychopharmacology 4th Generation of progress* Chapter 80, p. 921-928; and Substance abuse (*Psychopharmacology 4th Generation of progress* Chapter 25, p. 283 and 292, Chapter 66, p. 759-760, Chapter 147, p. 1725 (see also Nisell et al., "Systemic Nicotine-Induced Dopamine Release in the Rat Nucleus Accumbens is Regulated by Nicotinic receptors in the Ventral Tegmental Area; *Synapse* (1994) 16: 36-44). Chapter 149, p. 1745-1747 and 1751-1752). Drugs abused by humans preferentially increase synaptic dopamine concentrations in the mesolimbic system of freely moving rats Di Chiara et al *Proc Natl Acad Sci USA* 85, 5274, 1988. Drug addiction as a disorder of associative learning. Role of nucleus accumbens shell/extended amygdala dopamine *Ann N.Y. Acad Sci* 877, 461, 1999.

As shown by these references, the claimed conditions are recognized in the art as diseases which concern dopaminergic neurotransmission.

Furthermore, pharmacological interaction with dopaminergic neurotransmission is widely believed to be useful in the treatment of several CNS disorders, which are not generally believed to be directly caused by disruptions in dopaminergic neurotransmission. For example, the symptoms of Huntington's disease and other movement disorders can be treated with dopaminergic agents due to the involvement of dopamine in motor functions—(see *Psychopharmacology 4th Generation of progress*, Chapter 26, p. 295-301). Likewise, it is known that cognitive disorders (see *Psychopharmacology 4th Generation of progress* Chapters 25, p. 292, Chapter 120, p. 1417 and 1420, Chapter 123, p. 1447 and 1452 and 1455-1457) autism (see *Psychopharmacology 4th Generation of progress* Chapter 142, p. 1653 and 1661), attention-deficit hyperactivity disorder (see *Psychopharmacology 4th Generation of progress* Chapter 141, p. 1643 and 1649-1650), sexual disorders (see *Psychopharmacology 4th Generation of progress* Chapters 65, p. 743-746 and Chapter 22, p. 245 and 254) and eating disorders (see *Psychopharmacology 4th Generation of progress* Chapters 137, p. 1600, Chapter 138, p. 1609-1610 and 1612) may be treated with agents which interact with dopaminergic transmission. Thus, the above references support the argument that the compounds of the invention would be useful in the treatment of such diseases.

Depression

Dopamine and norepinephrine are cathecholamines. The cathecholamine hypothesis of depression was formulated in the 1960s (Schildkraut 1967). Evidence exists for a role for norepinephrine in depression (Principles of Neuropsychopharmacology, 1997, Sinauer Asociates Inc, USA. Chapter 19, p 838-9). Evidence also exists for a role for dopamine in depression (Principles of Neuropsychopharmacology, 1997, Sinauer Asociates Inc, USA. Chapter 19, p 848). Abnormalites in the cortex have been reported in those suffering from major depression (Neuropsychopharmacology: The fifth generation of progress, 2002, American college of Neuropsychopharmacology, USA, Chapter 73, p 1054 and chapter 74, p 1067)

Some antidepressants have a predominant effect upon the extracellullar levels of norepinephrine and dopamine versus 5-HT in the cortex, as measured by microdialysis. The common trait for all clinically effective classes of antidepressants is an elevation of the levels of dopamine and norepinephrine in the cortex (Tanda, Carboni et al. 1994; Millan, Lejeune et al. 2000). The clinically effective antdepressant mirtazapine (remeron) has been shown to increase predominantly extracellullar norepinephrine and dopamine in the cortex (See FIG. 1, Devoto, Flore et al. 2004). As the compounds of the present invention elevate the levels of dopamine and norepinephrine in the cortex we argue that they function as antidepressants (see FIG. 2, Example 2 in the present invention).

Figure 2:
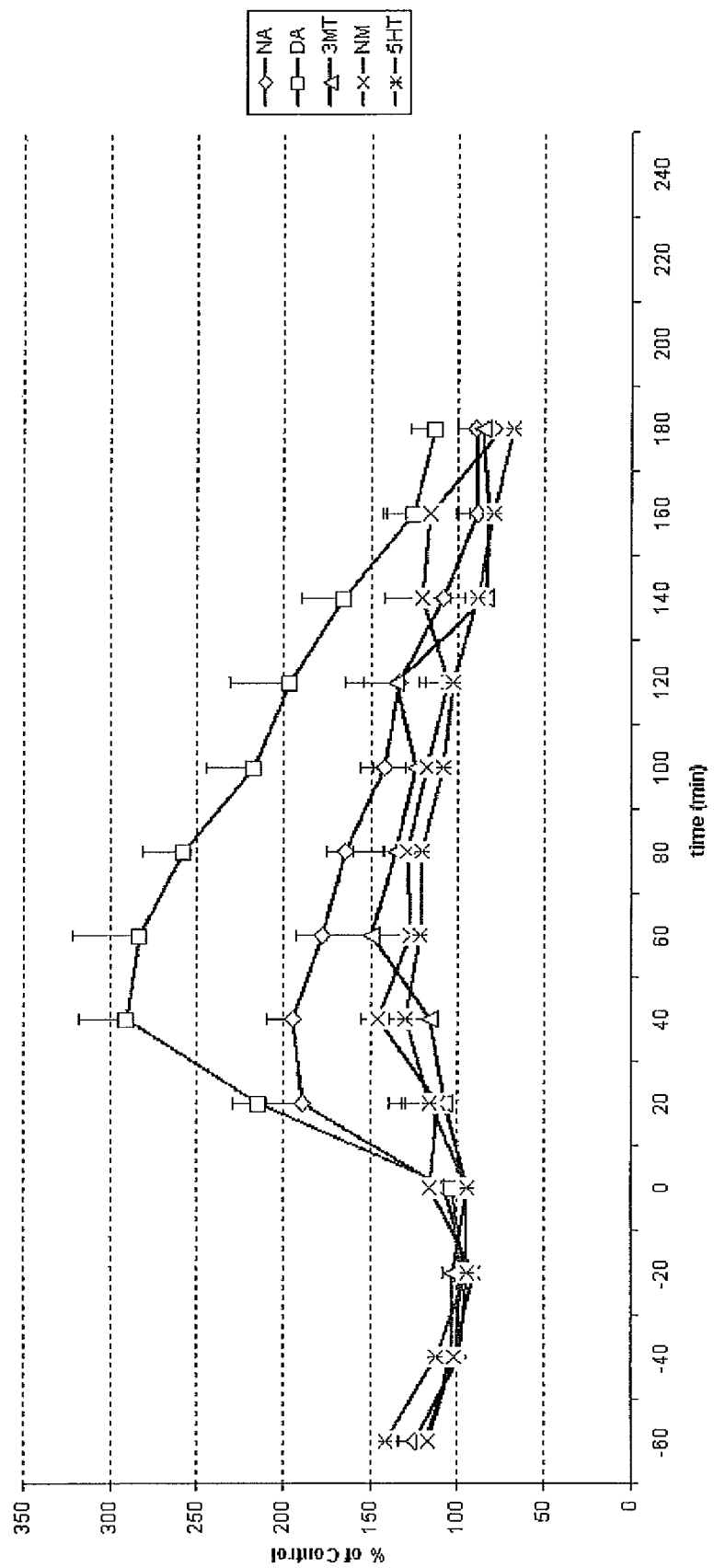
FIG. 2 is a graph showing the percent of control in relation to baseline values where Example 2 is injected (s.c.) at time-point 0.

FIG. 1. Remeron 10 mg/kg s.c. Cortex

Remeron is injected (s.c.) at time-point 0. The values depicted in the graph represent percent of control in relation to baseline values. The microdialysis was performed in awake and freely moving rats. Error-bars=SEM FIG. 2. 50 μmol/kg s.c. Summary pf. Cortex Amines n: 2.4

Example 2 is injected (s.c.) at time-point 0. The values depicted in the graph represent percent of control in relation to baseline values. The microdialysis was performed in awake and freely moving rats. Error-bars=SEM

REFERENCES

Devoto, P., G. Flore, L. Pira, G. Longu and G. L. Gessa (2004). "Mirtazapine-induced corelease of dopamine and noradrenaline from noradrenergic neurons in the medial prefrontal and occipital cortex." Eur J Pharmacol 487(1-3): 105-11.

Millan, M. J., F. Lejeune and A. Gobert (2000). "Reciprocal autoreceptor and heteroreceptor control of serotonergic, dopaminergic and noradrenergic transmission in the frontal cortex: relevance to the actions of antidepressant agents." J Psychopharmacol 14(2): 114-38.

Tanda, G., E. Carboni, R. Frau and G. Di Chiara (1994). "Increase of extracellular dopamine in the prefrontal cortex: a trait of drugs with antidepressant potential?" Psychopharmacology (Berl) 115(1-2): 285-8.

Schildkraut, J. J. (1967). "The catecholamine hypothesis of affective disorders. A review of supporting evidence." Int J Psychiatry 4(3): 203-17.

Methods of Preparation

The compounds of the invention may be prepared as outlined below in Schemes 1-4. However, the invention is not limited to these methods. The compounds may also be prepared as described for structurally-related compounds in the prior art. The reactions can be carried out according to standard procedures[1,2] or as described in the working examples. The starting materials for the processes described in the present application are known or may readily be prepared by conventional methods from commercially available chemicals.

Persons skilled in the art will appreciate that, in order to obtain compounds of the invention in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

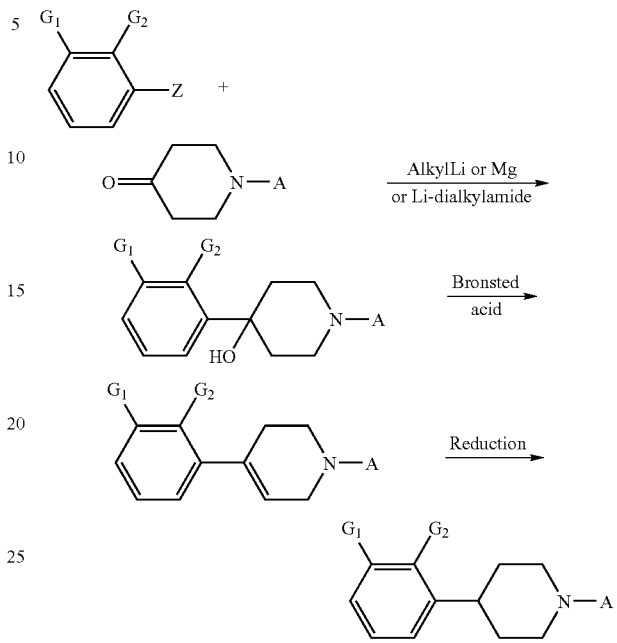

Scheme 1

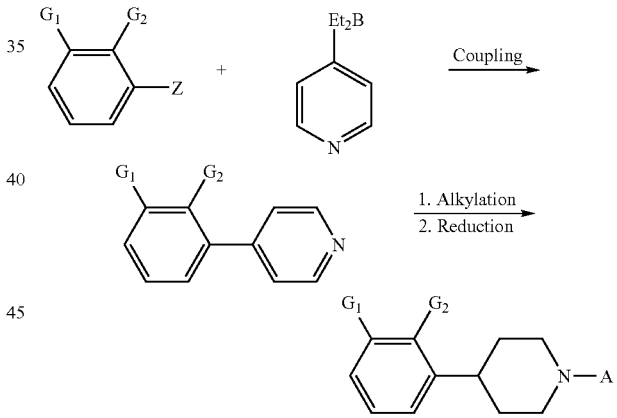

Scheme 2

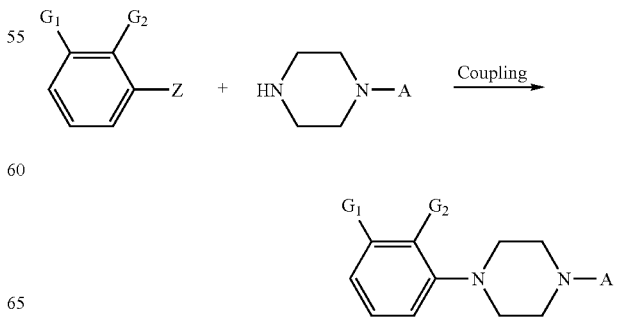

Scheme 3

Scheme 4

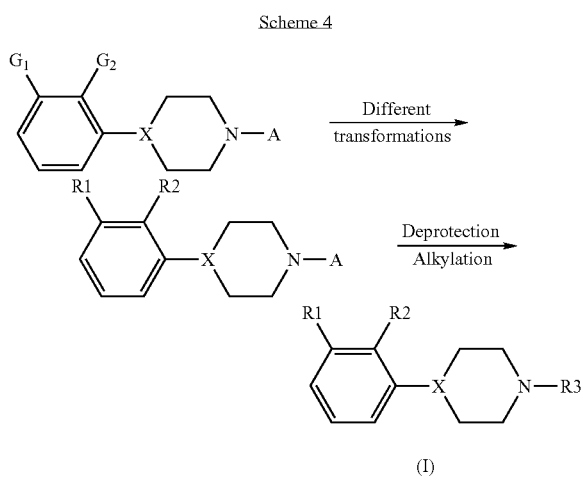

(I)

The substituents in Scheme 1-4, are as follows: Z is a leaving group, G1 is R1 or a group that can be transformed into R1, G2 is R2 or a group that can be transformed into R2, A is alkyl, hydrogen or a protecting group. X, R1, R2 and R3 are as defined above.

REFS

1. *Comprehensive Organic Transformations: A Guide to Functional Group Preparations* Richard C. Larock, 22 Oct. 1999 Wiley-VCH, ISBN: 0471190314
2. *March's Advanced Organic Chemistry: Reactions, Mechanisms, and Structure, 5th Edition*. Michael B. Smith, Jerry March, Jan. 15, 2001 Wiley-Interscience, ISBN: 0471585890

The term "patient" used herein refers to an individual in need of the treatment according to the invention.

The term "treatment" used herein relates to both treatment in order to cure or alleviate a disease or a condition and to treatment in order to prevent the development of a disease or a condition. The treatment may either be performed in an acute or in a chronic way.

Any chemical formula or name given herein is meant to include all stereo and optical isomers and racemates and mixtures thereof in any ratio. The various isomers can be obtained by standard methods well known to persons skilled in the art, e.g. via chromatography or fractional crystallisation. For example, cis/trans mixtures can be separated into the individual stereoisomers by stereoselective synthesis. Enantiomers or diastereomers may be isolated by separation of their mixtures, for instance by fractional crystallisation, resolution or HPLC. Alternatively separation can be afforded by derivatisation with a chiral reagent. Stereoisomers may be made by stereoselective synthesis from stereochemically pure starting materials under conditions which will not cause loss of stereochemical integrity. All stereoisomers are included within the scope of the invention.

The compounds of the present invention may be isolated in any level of purity by standard methods and purification can be achieved by conventional means known to those skilled in the art, such as distillation, recrystallization and chromatography.

The present invention relates to pharmaceutical compositions comprising the compounds of the present invention, and their use in treating CNS disorders. Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as toluensulfonate, methanesulfonate, fumarate, hydrochloride, hydrobromide, hydroiodide, nitrate, acetate, lactate, citrate, acid citrate, tartrate, bitartrate, aliphatic, alicyclic, aromatic or heterocyclic carboxylate, succinate, maleate, fumarate, gluconate, glycolate, saccharate, ascorbate, acetate, propionate, benzoate, pyruvate, pamoate [i.e., 1,1'-methylene-bis-(2-hydroxy-3-naphthoate)], phosphate, acid phosphate, sulphate or bisulfate salts. These salts are readily prepared by methods known in the art.

It is also to be understood that compounds of the present invention can exist in solvated as well as unsolvated forms such as, e.g, hydrated forms.

The pharmaceutical composition comprising a compound according to the invention may also comprise substances used to facilitate the production of the pharmaceutical preparation or the administration of the preparations. Such substances are well known to people skilled in the art and may for instance be pharmaceutically acceptable adjuvants, carriers and preservatives.

In clinical practice, the compounds according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate or sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Examples of tablet and capsule formulations suitable for oral administration are given below:

| Tablet I | mg/tablet |
|---|---|
| Compound | 100 |
| Lactose Ph.Eur | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound | 10 |
| Lactose Ph.Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 µM of the compound is obtained.

The invention is further illustrated in the examples below, which in no way are intended to limit the scope of the invention.

EXAMPLE 1

4-[2-FLUORO-3-(METHYLSULFONYL)PHENYL]-1-PROPYLPIPERIDINE

To a solution of 4-[2-fluoro-3-(methylsulfonyl)phenyl]piperidine (0.4 g, 1.55 mmol) in acetonitrile (40 ml) was added potassium carbonate (0.3 g, 2.17 mmol) and 1-iodopropane (0.151 ml, 1.55 mmol) and the mixture was heated at reflux for 15 h. The mixture was cooled to ambient temperature and water (50 ml) was added. The aqueous residue was extracted with ethylacetate (3×50 ml) and the combined organic phases was dried, concentrated, and purified by flash column chromatography (ethylacetate/methanol, 1:1) to give the title compound (0.37 g, 79%). The amine was converted to the hydrochloric acid salt and recrystallized from ethanol/diethyl ether: M.p. 255-257° C. MS m/z (relative intensity, 70 eV) 299 (M+, 2), 271 (16), 270 (bp), 147 (9) 133 (10).

EXAMPLE 2

1-ETHYL-4-[2-FLUORO-3-(METHYLSULFONYL)PHENYL]-PIPERIDINE

Preparation according to Example 1: 4-[2-fluoro-3-(methylsulfonyl)phenyl]-piperidine (0.185 g, 0.72 mmol), acetonitrile (10 ml), potassium carbonate (0.2 g, 1.44 mmol), 1-iodoethane (0.06 ml, 0.75 mmol). Yield: 0.15 g (73%). The amine was converted to several different salts and recrystallized from ethanol/diethyl ether. Hydrochloric acid salt m.p.

273-275° C., hydrobromic acid salt m.p. 267-268° C., fumaric acid salt m.p. 204-206° C., oxalic acid salt m.p. 163-165° C., sulfate salt m.p. 263-265° C., maleic acid salt m.p. 112-113° C. MS m/z (relative intensity, 70 eV) 285 (M+, 12), 271 (15), 270 (bp), 147 (7) 133 (8).

EXAMPLE 2

Synthesised Via Another Route

1-ETHYL-4-[2-FLUORO-3-(METHYLSULFO-NYL)PHENYL]PIPERIDINE

A mixture of 1-ethyl-4-[2-fluoro-3-(methylsulfonyl)phenyl]-1,2,3,6-tetrahydropyridine (5 g, 17, 7 mmol), formic acid (3.4 ml, 90 mmol) and palladium on carbon (1.1 g) in isopropanol (50 ml) was shaken in a parr apparatus for 20 h. The reaction mixture was filtered through a pad of celite and the filtrate was concentrated and evaporated to dryness. Aqueous sodium carbonate (10%, 200 ml) was added and the mixture was extracted with ethyl acetate (3×100 ml). The combined organic phases was dried ($MgSO_4$) and evaporated to dryness. Flash column chromatography (ethylacetate/methanol, 1:1) gave the title compound (3.5 g, 70%). The amine was converted to the hydrochloric acid salt and recrystallized from ethanol/diethyl ether: M.p. 280.2° C. MS m/z (relative intensity, 70 eV) 285 (M+, 12), 270 (bp), 57 (19), 84 (15) 133 (9).

EXAMPLE 3

4-[2-CHLORO-3-(METHYLSULFONYL)PHE-NYL]-1-PROPYLPIPERIDINE

A mixture of 4-[2-chloro-3-(methylsulfonyl)phenyl]-1-propyl-1,2,3,6-tetrahydropyridine (0.46 g, 1.47 mmol), platinum oxide (0.11 g) and hydrochloric acid (0.1 ml, conc) in methanol (30 ml) was hydrogenated at 50 psi for 1 h under hydrogen gas. The reaction mixture was filtered through a pad of celite and the filtrate was concentrated and evaporated to dryness to give 0.48 g of crude product as the hydrochloric acid salt. Purification by flash column chromatography (ethylacetate/methanol, 1:1) gave the title compound (0.35 g, 75%). The amine was converted to the hydrochloric acid salt and recrystallized from ethanol/diethyl ether: M.p. 250-252° C. MS m/z (relative intensity, 70 eV) 315 (M+, 3), 288 (37), 287 (15), 286 (bp) 129 (7).

EXAMPLE 4

4-[2-METHYL-3-(METHYLSULFONYL)PHE-NYL]-1-PROPYLPIPERIDINE

Preparation according to Example 1: 4-[2-methyl-3-(methylsulfonyl)phenyl]piperidine (0.41 g, 1.62 mmol), acetonitrile (40 ml), potassium carbonate (0.53 g, 4.8 mmol) and 1-iodopropane (0.127 ml, 1.62 mmol). Yield: 0.238 g (50%). The amine was converted to the hydrochloric acid salt and recrystallized from ethanol/diethyl ether: M.p. 233-235° C. MS m/z (relative intensity, 70 eV) 295 (M+, 4), 267 (17), 266 (bp), 129 (13), 115 (14).

EXAMPLE 5

3-(1-ETHYLPIPERIDIN-4-YL)-2-HYDROXY-BENZONITRILE

To a solution of 3-(1-ethylpiperidin-4-yl)-2-fluorobenzonitrile (10 mg, 0.031 mmol) in dimethylsulfoxide (1 ml) was added 2-butyn-1-ol (4.3 mg, 0.062 mmol) and potassium-tert-butoxide (7 mg, 0.063 mmol). The mixture was heated to 125° C. in a sealed tube under microwave radiation for 120 s. Aqueous hydrochloric acid (10%, 10 ml) was added and the aqueous phase was washed with diethyl ether (2×20 ml). The aqueous phase was basified by addition of sodium hydroxide (5 M, 5 ml) and extracted with ethyl acetate (3×20 ml). The combined organic phase was dried ($MgSO_4$) and evaporated under reduced pressure to give the title compound. MS m/z (relative intensity, 70 eV) 230 (M+, 60), 229 (24), 216 (23), 215 (bp) 110 (30).

EXAMPLE 6

2-(METHYLSULFONYL)-6-(1-PROPYLPIPERI-DIN-4-YL)ANILINE

4-[2-fluoro-3-(methylsulfonyl)phenyl]-1-propylpiperidine (0.45 g, 1.52 mmol) was dissolved in a solution of ammonia in methanol (7 M, 15 ml). The mixture was heated to 160° C. in a sealed tube under microwave radiation for 20 h. The solvent was evaporated and the crude product was purified on a preparative HPLC-system. Yield: 0.125 g (30%). The amine was converted to the hydrochloric acid salt and recrystallized from ethanol/diethyl ether: M.p. 232-233° C. MS m/z (relative intensity, 70 eV) 296 (M+, 22), 267 (bp), 224 (31), 130 (23) 117 (20).

EXAMPLE 7

2-(1-PROPYLPIPERIDIN-4-YL)-6-(TRIFLUO-ROMETHYL) BENZONITRILE

To a solution of 4-[2-fluoro-3-(trifluoromethyl)phenyl]-1-propylpiperidine (1.57 g, 5.4 mmol) in N,N-dimethylformamide (35 ml) was added sodium cyanide (1.0 g, 20 mmol) and 18-crown-6-ether (50 mg). The mixture was heated at reflux for 15 h and then brought to ambient temperature. Aqueous sodium carbonate (10%, 50 ml) was added and the phases were separated. The aqueous phase was extracted with ethylacetate (2×50 ml) and the combined organic phases was dried (MgSO4) and evaporated under reduced pressure to give an oil. Purification by flash column chromatography (ethylacetate/methanol, 1:1) gave the title compound: 0.72 g (45%). The amine was converted to the hydrochloric acid salt and recrystallized from ethanol/diethyl ether: M.p. 272-274° C. MS m/z (relative intensity, 70 eV) 296 (M+, 4), 268 (16), 267 (bp), 204 (3), 184 (3).

EXAMPLE 8

4-[2-METHOXY-3-(TRIFLUOROMETHYL)PHE-NYL]-1-PROPYLPIPERIDINE

Preparation according to Example 1: 4-[2-methoxy-3-(trifluoro-methyl)phenyl]piperidine (0.38 g, 1.47 mmol), acetonitrile (40 ml), potassium carbonate (0.4 g, 3.7 mmol) and 1-iodopropane (0.115 ml, 1.47 mmol). Yield: 0.33 g (74%). The amine was converted to the hydrochloric acid salt and

EXAMPLE 9

1-[2-FLUORO-3-(TRIFLUOROMETHYL)PHENYL]-4-PROPYLPIPERAZINE

Preparation according to Example 1: 1-[2-fluoro-3-(trifluoro-methyl)phenyl]piperazine (0.97 g, 3.9 mmol), acetonitrile (50 ml), potassium carbonate (0.81 g, 5.86 mmol) and 1-iodopropane (0.457 ml, 4.6 mmol). Yield: 0.57 g (50%). The amine was converted to the hydrochloric acid salt and recrystallized from ethanol/diethyl ether: M.p. 180-181° C. MS m/z (relative intensity, 70 eV) 290 (M+, 22), 262 (13), 261 (bp), 218 (18), 190 (22).

EXAMPLE 10

1-[2-FLUORO-3-(TRIFLUOROMETHYL)PHENYL]-4-(2-METHOXYETHYL)PIPERAZINE

Preparation according to Example 1: 1-[2-fluoro-3-(trifluoro-methyl)phenyl]piperazine (0.5 g, 2.0 mmol), acetonitrile (25 ml), potassium carbonate (0.42 g, 3.0 mmol) and 1-bromo-2-methoxyethane (0.189 ml, 2.0 mmol). Yield: 0.26 g (42%). The amine was converted to the hydrochloric acid salt and recrystallized from ethanol/diethyl ether: M.p. 170-171° C. MS m/z (relative intensity, 70 eV) 306 (M+, 9), 262 (13), 261 (bp), 218 (23), 190 (23).

EXAMPLE 11

1-(2,3-DICHLOROPHENYL)-4-PROPYLPIPERAZINE

Preparation according to Example 1: 1-(2,3-dichlorophenyl)piperazine (1.0 g, 3.74 mmol), acetonitrile (40 ml), potassium carbonate (1.55 g, 11.2 mmol) and 1-iodopropane (0.293 ml, 3.74 mmol). Yield: 0.23 g (20%). The amine was converted to the hydrochloric acid salt and recrystallized from ethanol/diethyl ether: M.p. 220-221° C. MS m/z (relative intensity, 70 eV) 274 (M+, 15), 272 (M+, 22), 245 (63), 243 (bp), 174 (22), 172 (27).

EXAMPLE 12

1-ALLYL-4-[2-METHYL-3-(METHYLSULFONYL)PHENYL]PIPERIDINE

Preparation according to Example 1: 4-[2-methyl-3-(methylsulfonyl)phenyl]piperidine (0.01 g), acetonitrile (2 ml), potassium carbonate (0.01) and allylbromide (0.01 g). MS m/z (rel. intensity, 70 eV) 293 (M+, 16), 292 (16), 278 (26), 266 (bp), 129 (19).

EXAMPLE 13

3-(1-PROPYLPIPERIDIN-4-YL)-2-(TRIFLUOROMETHYL)BENZONITRILE

Preparation according to Example 7: 4-[3-fluoro-2-(trifluoromethyl)phenyl]-1-propylpiperidine (0.81 g, 2.8 mmol), N,N-dimethylformamide (30 ml), sodium cyanide (0.5 g, 10 mmol) and 18-crown-6-ether (30 mg). Yield: 0.53 g (64%). The amine was converted to the hydrochloric acid salt and recrystallized from ethanol/diethyl ether: M.p. 266-269° C. MS m/z (relative intensity, 70 eV) 296 (M+, 3), 268 (16), 267 (bp), 204 (3), 184 (3).

EXAMPLE 14

3-(4-PROPYLPIPERAZIN-1-YL)-2-(TRIFLUOROMETHYL)BENZONITRILE

Preparation according to Example 1: 3-piperazin-1-yl-2-(trifluoromethyl)benzonitrile (0.83 g, 3.25 mmol), acetonitrile (40 ml), potassium carbonate (0.88 g, 8.1 mmol) and 1-iodopropane (0.255 ml, 3.25 mmol). Yield: 0.74 g (77%). The amine was converted to the hydrochloric acid salt and recrystallized from ethanol/diethyl ether: M.p. 234-236° C. MS m/z (relative intensity, 70 eV) 297 (M+, 15), 269 (14), 268 (bp), 225 (26), 177 (8).

EXAMPLE 15

2-(METHYLSULFONYL)-6-(1-PROPYLPIPERIDIN-4-YL)BENZONITRILE

Preparation according to Example 7: 4-[2-fluoro-3-(methylsulfonyl)phenyl]-1-propylpiperidine (0.2 g, 0.67 mmol), N,N-dimethylformamide (30 ml), sodium cyanide (0.82 g, 1.67 mmol) and 18-crown-6-ether (5 mg). Yield: 0.06 g (29%). The amine was converted to the hydrochloric acid salt and recrystallized from ethanol/diethyl ether: MS m/z (relative intensity, 70 eV) 306 (M+, 3), 279 (6), 278 (16), 277 (bp), 198 (5).

EXAMPLE 16

4-[3-FLUORO)-2-(TRIFLUOROMETHYL)PHENYL]-1-PROPYLPIPERIDINE

To a solution of 4-[3-fluoro-2-(trifluoromethyl)phenyl]-1-propyl-1,2,3,6-tetrahydro pyridine (1.73 g, 6.0 mmol) in ethanol (30 ml) was added Raney nickel (slurry in water, 10 ml) and the reaction mixture was hydrogenated under hydrogen (50 psi) for 2 days. Filtration through a pad of celite and evaporation of the filtrate gave 1.35 g of crude product. MS m/z (relative intensity, 70 eV) 289 (M+, 4), 261 (16), 260 (bp), 176 (6) 70 (20).

EXAMPLE 17

4-[2-FLUORO-3-(METHYLSULFONYL)PHENYL]-1-(2-METHOXYETHYL)-PIPERIDINE

Preparation according to Example 1: 4-[2-fluoro-3-(methylsulfonyl)-phenyl]-piperidine (0.53 g, 1.64 mmol), acetonitrile (20 ml), potassium carbonate (0.45 g, 3.2 mmol), 1-bromo-2-methoxyethane (0.167 ml, 1.72 mmol). MS m/z (relative intensity, 70 eV) 315 (M+, 1), 271 (14), 270 (bp), 147 (10) 133 (9).

EXAMPLE 18

4-[2-FLUORO-3-(METHYLSULFONYL)PHENYL]-1-METHYLPIPERIDINE

To a solution of 4-[2-fluoro-3-(methylsulfonyl)-phenyl]-piperidine (0.02 g, 0.078 mmol) in acetonitrile (2 ml) was added potassium carbonate (0.02 g, 0.14 mmol) and iodomethane (0.0047 ml, 0.078 mmol). The mixture was stirred at ambient temperature for 1 h. MS m/z (relative intensity, 70 eV) 271 (M+, 66), 270 (bp), 192 (9), 133 (13) 97 (32).

EXAMPLE 19

1-BUTYL-4-[2-FLUORO-3-(METHYLSULFONYL)PHENYL]PIPERIDINE

Preparation according to Example 1: 4-[2-fluoro-3-(methylsulfonyl)-phenyl]-piperidine (0.02 g, 0.078 mmol), acetonitrile (2 ml), potassium carbonate (0.02 g, 0.14 mmol), 1-bromobutane (0.009 ml, 0.082 mmol). MS m/z (relative intensity, 70 eV) 313 (M+, 2), 271 (14), 270 (bp), 147 (7) 133 (7).

EXAMPLE 20

4-[2-FLUORO-3-(METHYLSULFONYL)PHENYL]-1-ISOPROPYL-PIPERIDINE

Preparation according to Example 1: 4-[2-fluoro-3-(methylsulfonyl)-phenyl]-piperidine (0.02 g, 0.078 mmol), acetonitrile (2 ml), potassium carbonate (0.02 g, 0.14 mmol), 2-bromopropane (0.008 ml, 0.082 mmol). MS m/z (relative intensity, 70 eV) 299 (M+, 3), 285 (15), 284 (bp), 205 (6) 133 (4).

EXAMPLE 21

4-[2-FLUORO-3-(METHYLSULFONYL)PHENYL]-1-ISOBUTYL-PIPERIDINE

Preparation according to Example 1: 4-[2-fluoro-3-(methylsulfonyl)-phenyl]-piperidine (0.02 g, 0.078 mmol), acetonitrile (2 ml), potassium carbonate (0.02 g, 0.14 mmol), 1-bromo-2-methylpropane (0.009 ml, 0.082 mmol). MS m/z (relative intensity, 70 eV) 313 (M+, 1), 271 (15), 270 (bp), 147 (8) 133 (8).

EXAMPLE 22

4-[2-FLUORO-3-(METHYLSULFONYL)PHENYL]-1-(3,3,3-TRIFLUORO-PROPYL)PIPERIDINE

Preparation according to Example 1: 4-[2-fluoro-3-(methylsulfonyl)phenyl]piperidine (0.02 g, 0.078 mmol), acetonitrile (2 ml), potassium carbonate (0.02 g, 0.14 mmol), 1,1,1-trifluoro-3-iodopropane (0.010 ml, 0.082 mmol). MS m/z (relative intensity, 70 eV) 353 (M+, 11), 271 (15), 270 (bp), 152 (14) 133 (9).

EXAMPLE 23

2-FLUORO-3-(1-PROPYLPIPERIDIN-4-YL)PHENYL METHANESULFONATE

Preparation according to Example 1: 2-fluoro-3-piperidin-4-ylphenyl methanesulfonate (0.01 g), acetonitrile (2 ml), potassium carbonate (0.01 g) and iodopropane (0.01 g). MS m/z (rel. intensity, 70 eV) 315 (M+, 4), 287 (16), 286 (bp), 236 (2), 207 (41).

EXAMPLE 24

3-(1-ALLYLPIPERIDIN-4-YL)-2-FLUOROPHENYL METHANESULFONATE

Preparation according to Example 1: 2-fluoro-3-piperidin-4-ylphenyl methanesulfonate (0.01 g), acetonitrile (2 ml), potassium carbonate (0.01 g) and allylbromide (0.01 g). MS m/z (rel. intensity, 70 eV) 313 (M+, 28), 312 (25), 286 (42), 234 (bp), 207 (19).

EXAMPLE 25

2-FLUORO-3-[1-(2-METHOXYETHYL)PIPERIDIN-4-YL]PHENYL METHANESULFONATE

Preparation according to Example 1: 2-fluoro-3-piperidin-4-ylphenyl methanesulfonate (0.01 g), acetonitrile (2 ml), potassium carbonate (0.01 g) and 1-bromo-2-methoxyethane (0.01 g). MS m/z (rel. intensity, 70 eV) 331 (M+, 1), 288 (6), 287 (15), 286 (bp), 207 (47).

EXAMPLE 26

1-[2-(1,3-DIOXOLAN-2-YL)ETHYL]-4-[2-FLUORO-3-(METHYLSULFONYL)PHENYL]-PIPERIDINE

Preparation according to Example 1: 4-[2-fluoro-3-(methylsulfonyl)phenyl]piperidine (0.42 g, 1.63 mmol), acetonitrile (20 ml), potassium carbonate (0.45 g, 3.2 mmol) and 2-(2-bromoethyl)-1,3-dioxolan (0.205 ml, 1.65 mmol). Yield: 0.18 g (31%). The amine was converted to the hydrochloric acid salt and recrystallized from ethanol/diethyl ether: M.p. 224-225° C. MS m/z (relative intensity, 70 eV) 357 (M+, 3), 270 (bp), 257 (59), 256 (27), 178 (90).

EXAMPLE 27

2-{4-[2-FLUORO-3-(TRIFLUOROMETHYL)PHENYL]PIPERIDIN-1-YL}ETHANOL

Preparation according to Example 1: 4-[2-fluoro-3-(trifluoromethyl)phenyl]piperidine (0.45 g, 1.82 mmol), acetonitrile (20 ml), potassium carbonate (0.6 g, 1.1 mmol) and 2-iodoethanol (0.16 ml, 2.0 mmol). Yield: 0.35 g (66%). The amine was converted to the hydrochloric acid salt and recrystallized from ethanol/diethyl ether: M.p. 224-226° C. MS m/z (relative intensity, 70 eV) 291 (M+, 1), 260 (bp), 217 (5), 189 (3), 177 (7).

EXAMPLE 28

4-[2-CHLORO-3-(METHYLSULFONYL)PHENYL]-1-ETHYLPIPERIDINE

Preparation according to Example 3: 4-[2-chloro-3-(methylsulfonyl)phenyl]-1-ethyl-1,2,3,6-tetrahydropyridine (0.6 g, 2.0 mmol), methanol (25 ml), platinum oxide (0.15 g). Yield: 0.35 g (58%). The amine was converted to hydrochlorid acid salt and recrystallized from ethanol/diisopropyl ether: M.p. 264-265° C. MS m/z (relative intensity, 70 eV) 301 (M+, 6), 301 (13), 300 (11), 288 (35) 286 (bp).

EXAMPLE 29

2-(1-PROPYLPIPERIDIN-4-YL)-6-(TRIFLUOROMETHYL)PHENOL

4-[2-methoxy-3-(trifluoromethyl)phenyl]-1-propylpiperidine (0.18 g, 0.6 mmol) and pyridine hydrochloride (2 g) was heated to 190° C. and stirred for 2 h. Aqueous sodium carbonate (10%, 50 ml) and ethyl acetate (50 ml) was added and the phases were separated. The aqueous phase was extracted with ethyl acetate (2×50 ml) and the combined organic phase was dried (MgSO4) and evaporated under reduced pressure to give an oil. Purification by flash column chromatography (ethyl acetate/methanol, 1:1) gave the title compound: 0.17 g (98%). The amine was converted to the hydrochloric acid salt and recrystallized from ethanol/diethyl ether: M.p. 218-220° C. MS m/z (relative intensity, 70 eV) 287 (M+, 10), 259 (14), 258 (bp), 238 (15), 195 (19).

EXAMPLE 30

2-(1-PROPYLPIPERIDIN-4-YL)-6-(TRIFLUOROMETHOXY)PHENOL

Preparation according to Example 29: 4-[2-methoxy-3-(trifluoromethoxy)phenyl]-1-propylpiperidine (1.32 g, 4.16 mmol), pyridine hydrochloride (3 g). Yield: 0.7 g (55%). The amine was converted to the hydrochloric acid salt and recrystallized from ethanol/diethyl ether: M.p. 203-205° C. MS m/z (relative intensity, 70 eV) 303 (M+, 11), 275 (15), 274 (bp), 145 (4), 117 (6).

EXAMPLE 31

3-(1-PROPYLPIPERIDIN-4-YL)PHTHALONITRILE

To a solution of 4-[2-fluoro-3-(methylsulfonyl)phenyl]-1-propylpiperidine (0.2 g, 0.67 mmol) in N,N-dimethylformamide (30 ml) was added sodium cyanide (0.82 g, 1.67 mmol) and 18-crown-6-ether (5 mg). The mixture was heated at reflux for 15 h and then brought to ambient temperature. Aqueous sodium carbonate (10%, 50 ml) was added and the phases were separated. The aqueous phase was extracted with ethylacetate (2×50 ml) and the combined organic phases was dried (MgSO4) and evaporated under reduced pressure to give an oil. Purification by flash column chromatography (ethylacetate/methanol, 1:1) gave the title compound: 0.07 g (41%). MS m/z (relative intensity, 70 eV) 253 (M+, 3), 225 (17), 224 (bp), 154 (6), 70 (12).

EXAMPLE 32

3-{4-[2-FLUORO-3-(TRIFLUOROMETHYL)PHENYL]PIPERIDIN-1-YL}PROPAN-1-OL

Preparation according to Example 1: 4-[2-fluoro-3-(trifluoromethyl)phenyl]piperidine (0.45 g, 1.82 mmol), acetonitrile (20 ml), potassium carbonate (0.6 g, 1.1 mmol) and 3-bromo-1-propanol (0.185 ml, 2.0 mmol). Yield: 0.16 g (29%). The amine was converted to the hydrochloric acid salt and recrystallized from ethanol/diethyl ether: M.p. 259-261° C. MS m/z (relative intensity, 70 eV) 305 (M+, 4), 261 (16), 260 (bp), 217 (5), 177 (9).

EXAMPLE 33

3-(1-ETHYLPIPERIDIN-4-YL)-2-FLUOROPHENYL METHANESULFONATE

To a solution of 3-(1-ethylpiperidin-4-yl)-2-fluorophenol (0.44 g, 1.97 mmol)) in methylene chloride (20 ml) was added triethylamine (4 ml) and methanesulfonyl chloride (0.56 ml, 3.67 mmol). The mixture was stirred for 20 h and water (50 ml) and methylene chloride (50 ml) was added and the phases were separated. The aqueous phase was extracted with methylene chloride (2×50 ml) and the combined organic phases was dried (MgSO4) and evaporated under reduced pressure to give an oil. Purification by flash column chromatography (ethyl acetate/methanol, 1:1) gave the title compound: 0.39 g (66%). The amine was converted to the oxalic acid salt and recrystallized from ethanol/diethyl ether: M.p. 161.5-163.2. MS m/z (relative intensity, 70 eV) 301 (M+, 15), 287 (15), 286 (bp), 222 (23), 207 (38).

EXAMPLE 34

3-(1-ETHYLPIPERIDIN-4-YL)-2-FLUOROPHENYL TRIFLUOROMETHANESULFONATE

To a solution of 3-(1-ethylpiperidin-4-yl)-2-fluorophenol (0.5 g, 2.24 mmol) in methylene chloride (20 ml) was added triethylamine (4 ml) and trifluoromethanesulfonic anhydride (0.75 ml, 4.5 mmol). The mixture was stirred for 20 h, water (50 ml) and methylene chloride (50 ml) was added and the phases were separated. The aqueous phase was extracted with methylene chloride (2×50 ml) and the combined organic phases was dried (MgSO4) and evaporated under reduced pressure to give an oil. Purification by flash column chromatography (ethyl acetate/methanol, 1:1) gave the title compound: 0.47 g (59%). The amine was converted to the fumaric acid salt and recrystallized from ethanol/diethyl ether: M.p. 158-159° C. MS m/z (relative intensity, 70 eV) 355 (M+, 20), 341 (18), 340 (bp), 222 (18), 207 (77).

EXAMPLE 35

3-(1-ETHYLPIPERIDIN-4-YL)-2-FLUORO-N,N-DIMETHYLBENZENESULFONAMIDE

Preparation according to Example 3: 3-(1-ethyl-1,2,3,6-tetrahydropyridin-4-yl)-2-fluoro-N,N-dimethylbenzenesulfonamide (0.27 g, 0.86 mmol), methanol (10 ml), platinum oxide (0.05 g). Yield: 0.16 g (59%). The amine was converted to fumaric acid salt and recrystallized from ethanol/diisopropyl ether: M.p. 151-152° C. MS m/z (relative intensity, 70 eV) 314 (M+, 18), 313 (11), 300 (17), 299 (bp) 191 (11).

EXAMPLE 36

1-[3-(1-ETHYLPIPERIDIN-4-YL)-2-FLUOROPHENYL]ETHANONE

To a solution of 1-ethyl-4-[2-fluoro-3-(2-methyl-1,3-dioxolan-2-yl)phenyl]piperidine (0.28 g, 0.95 mmol) in methanol (20 ml) was added a solution of hydrogen chloride in ethanol (5 ml, saturated) and the mixture was stirred for 20 h. The solvent was evaporated and the crude product was recrystallized from ethanol/diethyl ether to give the title compound as the hydrochloric acid salt. Yield: 0.13 g (47%). M.p. 199-202° C. MS m/z (relative intensity, 70 eV) 249 (M+, 19), 235 (15), 234 (bp), 149 (11) 133 (18).

EXAMPLE 37

1-[3-(1-ETHYLPIPERIDIN-4-YL)-2-HYDROXYPHENYL]ETHANONE

Preparation according to Example 5: 1-[3-(1-ethylpiperidin-4-yl)-2-fluorophenyl]ethanone (12 mg, 0.048 mmol), dimethylsulfoxide (1 ml), 2-butyn-1-ol (6.7 mg, 0.096 mmol), potassium-tertbutoxide (11 mg, 0.096 mmol). MS m/z (relative intensity, 70 eV) 247 (M+, 57), 232 (bp), 218 (28), 147 (24) 84 (67).

EXAMPLE 38

1-[2-FLUORO-3-(METHYLSULFONYL)PHENYL]-4-PROPYLPIPERAZINE

Preparation according to Example 1: 1-[2-fluoro-3-(methylsulfonyl)phenyl]piperazine (0.13 g, 0.52 mmol), acetonitrile (4 ml), potassium carbonate (014 g, 1.1 mmol) and 1-iodopropane (0.05 ml, 0.55 mmol). Yield: 0.1 g (64%). The amine was converted to the hydrochloric acid salt and recrystallized from ethanol/diethyl ether: M.p. 241-243° C. MS m/z (relative intensity, 70 eV) 300 (M+, 18), 272 (14), 271 (bp), 228 (11), 70 (49).

EXAMPLE 39

1-ETHYL-4-{2-FLUORO-3-[(TRIFLUOROMETHYL)SULFONYL]PHENYL}PIPERIDINE

Preparation according to Example 1: 4-{2-fluoro-3-[(trifluoromethyl)sulfonyl]phenyl}-piperidine (0.11 g, 0.35 mmol), acetonitrile (4 ml), potassium carbonate (0.063 g, 0.7 mmol) and 1-iodoethane (0.055 g, 0.35 mmol). Yield: 0.068 g (57%). The amine was converted to the hydrochloric acid salt and recrystallized from ethanol/diethyl ether: M.p. 189-191° C. MS m/z (relative intensity, 70 eV) 339 (M+, 8), 325 (15), 324 (bp), 205 (6), 191 (15).

EXAMPLE 40

1-ALLYL-4-[2-FLUORO-3-(METHYLSULFONYL)PHENYL]PIPERIDINE

Preparation according to Example 1: 4-[2-fluoro-3-(methylsulfonyl)phenyl]piperidine (0.34 g, 1.32 mmol), acetonitrile (4 ml), potassium carbonate (0.34 g, 2.6 mmol) and allyl bromide (0.12 ml, 1.38 mmol). Yield: 0.2 g (51%). The amine was converted to the hydrochloric acid salt and recrystallized from ethanol/diethyl ether: M.p. 259-261° C. MS m/z (relative intensity, 70 eV) 297 (M+, 87), 296 (82), 270 (bp, 268 (41), 133 (57).

EXAMPLE 41

1-ETHYL-4-[2-FLUORO-3-(METHYLSULFONYL)PHENYL]PIPERAZINE

Preparation according to Example 1: 1-[2-fluoro-3-(methylsulfonyl)phenyl]piperazine (0.13 g, 0.52 mmol), acetonitrile (4 ml), potassium carbonate (0.14 g, 1.1 mmol) and iodoethane (0.48 ml, 0.52 mmol). Yield: 0.09 g (60%). The amine was converted to the hydrochloric acid salt and recrystallized from ethanol/diethyl ether: M.p. 214-216° C. MS m/z (relative intensity, 70 eV) 286 (M+, 59), 272 (14), 271 (87), 201 (11), 57 (bp).

EXAMPLE 42

2-(1-ETHYLPIPERIDIN-4-YL)-6-(TRIFLUOROMETHYL)PHENOL

Preparation according to Example 1: 2-piperidin-4-yl-6-(trifluoromethyl)phenol (0.01 g, 0.04 mmol), acetonitrile (2 ml), potassium carbonate (0.01 g) and iodoethane (0.01 ml). MS m/z (relative intensity, 70 eV) 273 (M+, 37), 259 (15), 258 (bp), 238 (18), 195 (19).

EXAMPLE 43

2-[1-(2-FLUOROETHYL)PIPERIDIN-4-YL]-6-(TRIFLUOROMETHYL)PHENOL

Preparation according to Example 1: 2-piperidin-4-yl-6-(trifluoromethyl)phenol (0.01 g, 0.04 mmol), acetonitrile (2 ml), potassium carbonate (0.01 g) and 1-bromo-2-fluoroethane (0.01 ml). MS m/z (relative intensity, 70 eV) 291 (M+, 29), 259 (15), 258 (bp), 194 (22), 167 (11).

EXAMPLE 44

2-(1-ISOPROPYLPIPERIDIN-4-YL)-6-(TRIFLUOROMETHYL)PHENOL

Preparation according to Example 1: 2-piperidin-4-yl-6-(trifluoromethyl)phenol (0.01 g, 0.04 mmol), acetonitrile (2 ml), potassium carbonate (0.01 g) and isopropyl bromide (0.01 ml). MS m/z (relative intensity, 70 eV) 287 (M+, 13), 272 (bp), 253 (13), 252 (44), 166 (12).

EXAMPLE 45

2-(1-ISOBUTYLPIPERIDIN-4-YL)-6-(TRIFLUOROMETHYL)PHENOL

Preparation according to Example 1: 2-piperidin-4-yl-6-(trifluoromethyl)phenol (0.01 g, 0.04 mmol), acetonitrile (2 ml), potassium carbonate (0.01 g) and isobutyl bromide (0.01 ml). MS m/z (relative intensity, 70 eV) 301 (M+, 4), 259 (13), 258 (bp), 238 (9), 194 (11).

EXAMPLE 46

2-[1-(2,2,2-TRIFLUOROETHYL)PIPERIDIN-4-YL]-6-(TRIFLUOROMETHYL)PHENOL

Preparation according to Example 1: 2-piperidin-4-yl-6-(trifluoromethyl)phenol (0.01 g, 0.04 mmol), acetonitrile (2 ml), potassium carbonate (0.01 g) and 1,1,1-trifluoro-3-iodopropane (0.01 ml). MS m/z (relative intensity, 70 eV) 341 (M+, 40), 258 (bp), 195 (25), 167 (28), 152 (56).

EXAMPLE 47

4-[2-FLUORO-3-(TRIFLUOROMETHYL)PHENYL]-1-(2-METHOXYETHYL)PIPERIDINE

Preparation according to Example 1: 4-[2-fluoro-3-(trifluoromethyl)phenyl]piperidine (0.45 g, 1.82 mmol), acetonitrile (20 ml), potassium carbonate (0.6 g, 1.1 mmol) and 1-bromo-2-methoxyethane (0.16 ml, 2.0 mmol). Yield: 0.34 g (61%). The amine was converted to the hydrochloric acid salt and recrystallized from ethanol/diethyl ether: M.p. 180-181° C. MS m/z (relative intensity, 70 eV) 305 (M+, 2), 261 (14), 260 (bp), 217 (5), 177 (9).

EXAMPLE 48

4-[2-METHYL-3-(METHYLSULFONYL)PHENYL]-1-ETHYLPIPERIDINE

Preparation according to Example 1: 4-[2-methyl-3-(methyl-sulfonyl)phenyl]piperidine (0.17 g, 0.67 mmol), acetonitrile (20 ml), potassium carbonate (0.23 g, 1.67 mmol) and 1-iodoethane (0.065 ml, 0.74 mmol). Yield: 0.12 g (64%). MS m/z (relative intensity, 70 eV) 281 (M+, 22), 267 (17), 266 (bp), 129 (12), 115 (24).

EXAMPLE 49

1-ETHYL-4-[2-FLUORO-3-(METHYLSULFINYL) PHENYL]PIPERIDINE

Preparation according to Example 2. 1-ethyl-4-[2-fluoro-3-(methylsulfinyl)phenyl]-1,2,3,6-tetrahydropyridine (150 mg, 0.56 mmol), formic acid (0.1 ml, 2.8 mmol), palladium on carbon (0.1 g), isopropanol (20 ml). MS m/z (relative intensity, 70 eV) 269 (M+, 11), 254 (bp), 239 (84), 84 (13), 57 (11).

EXAMPLE 50

4-{2-FLUORO-3-[(TRIFLUOROMETHYL)SULFONYL]PHENYL}-1-PROPYLPIPERIDINE

Preparation according to Example 1: 4-{2-fluoro-3-[(trifluoromethyl)sulfonyl]phenyl}-piperidine (0.01 g), acetonitrile (2 ml), potassium carbonate (0.01 g) and 1-iodopropane (0.01 g). MS m/z (rel. intensity, 70 eV) 353 (M+, 1), 325 (15), 324 (bp), 191 (37), 133 (14).

EXAMPLE 51

1-ALLYL-4-{2-FLUORO-3-[(TRIFLUOROMETHYL)SULFONYL]PHENYL}PIPERIDINE

Preparation according to Example 1: 4-{2-fluoro-3-[(trifluoromethyl)sulfonyl]phenyl}-piperidine (0.01 g), acetonitrile (2 ml), potassium carbonate (0.01 g) and allylbromide (0.01 g). MS m/z (rel. intensity, 70 eV) 351 (M+, 47), 350 (61), 324 (bp), 322 (29), 133 (36).

EXAMPLE 52

4-{2-FLUORO-3-[(TRIFLUOROMETHYL)SULFONYL]PHENYL}-1-(2-METHOXYETHYL)-PIPERIDINE

Preparation according to Example 1: 4-{2-fluoro-3-[(trifluoromethyl)sulfonyl]phenyl}-piperidine (0.01 g), acetonitrile (2 ml), potassium carbonate (0.01 g) and 1-bromo-2-methoxyethane (0.01 g). MS m/z (rel. intensity, 70 eV) 369 (M+, 1), 325 (15), 324 (bp), 191 (37), 133 (14).

EXAMPLE 53

2-(4-{2-FLUORO-3-[(TRIFLUOROMETHYL) SULFONYL]PHENYL}PIPERIDIN-1-YL)ETHANOL

Preparation according to Example 1: 4-{2-fluoro-3-[(trifluoromethyl)sulfonyl]phenyl}-piperidine (0.01 g), acetonitrile (2 ml), potassium carbonate (0.01 g) and 2-iodoethanol (0.01 g). MS m/z (rel. intensity, 70 eV) 355 (M+, 1), 325 (15), 324 (bp), 191 (36), 133 (12).

EXAMPLE 54

4-{2-FLUORO-3-[(TRIFLUOROMETHYL)SULFONYL]PHENYL}-1-METHYLPIPERIDINE

Preparation according to Example 18: 4-{2-fluoro-3-[(trifluoromethyl)sulfonyl]phenyl}-piperidine (0.01 g), acetonitrile (2 ml), potassium carbonate (0.01 g) and iodomethane (0.01 g). MS m/z (rel. intensity, 70 eV) 325 (M+, 63), 324 (bp), 305 (13), 191 (32), 133 (24).

EXAMPLE 55

1-(2-METHOXYETHYL)-4-[2-METHYL-3-(METHYLSULFONYL)PHENYL]PIPERIDINE

Preparation according to Example 1: 4-[2-methyl-3-(methylsulfonyl)phenyl]piperidine (0.01 g), acetonitrile (2 ml), potassium carbonate (0.01) and allylbromide (0.01 g). MS m/z (rel. intensity, 70 eV) 311 (M+, 2), 267 (17), 266 (bp), 129 (8), 70 (10).

EXAMPLE 56

2-(1-ETHYLPIPERIDIN-4-YL)-6-(TRIFLUOROMETHOXY)PHENOL

Preparation according to Example 1: 2-piperidin-4-yl-6-(trifluoromethoxy)phenol (0.01 g), acetonitrile (2 ml), potassium carbonate (0.01 g) and 2-iodoethane (0.01 g). MS m/z (relative intensity, 70 eV) 289 (M+, 45), 288 (20), 275 (15), 274 (bp), 84 (26).

EXAMPLE 57

2-[1-(2-HYDROXYETHYL)PIPERIDIN-4-YL]-6-(TRIFLUOROMETHOXY)PHENOL

Preparation according to Example 1: 2-piperidin-4-yl-6-(trifluoromethoxy)phenol (0.01 g), acetonitrile (2 ml), potassium carbonate (0.01 g) and 2-iodoethanol (0.01 g). MS m/z (relative intensity, 70 eV) 305 (M+, 1), 275 (15), 274 (bp), 117 (5), 70 (20).

EXAMPLE 58

1-[2-FLUORO-3-(1-PROPYLPIPERIDIN-4-YL) PHENYL]ETHANONE

Preparation according to Example 1: 1-(2-fluoro-3-piperidin-4-ylphenyl)ethanone (0.01 g), acetonitrile (2 ml), potassium carbonate (0.01 g) and 2-iodopropane (0.01 g). MS m/z (rel. intensity, 70 eV) 263 (M+, 4), 235 (15), 234 (bp), 163 (3), 133 (4).

EXAMPLE 59

1-{2-FLUORO-3-[1-(2-HYDROXYETHYL)PIPERIDIN-4-YL]PHENYL}ETHANONE

Preparation according to Example 1: 1-(2-fluoro-3-piperidin-4-ylphenyl)ethanone (0.01 g), acetonitrile (2 ml), potassium carbonate (0.01 g) and 2-iodoethanol (0.01 g). MS m/z (rel. intensity, 70 eV) 265 (M+, 1), 235 (16), 234 (bp), 133 (5), 109 (5).

EXAMPLE 60

1-[3-(1-ALLYLPIPERIDIN-4-YL)-2-FLUOROPHENYL]ETHANONE

Preparation according to Example 1: 1-(2-fluoro-3-piperidin-4-ylphenyl)ethanone (0.01 g), acetonitrile (2 ml), potassium carbonate (0.01 g) and allylbromide (0.01 g). MS m/z (rel. intensity, 70 eV) 261 (M+, 89), 260 (82), 234 (bp), 218 (25), 82 (32).

EXAMPLE 61

1-{2-FLUORO-3-[1-(2-METHOXYETHYL)PIPERIDIN-4-YL]PHENYL}ETHANONE

Preparation according to Example 1: 1-(2-fluoro-3-piperidin-4-ylphenyl)ethanone (0.01 g), acetonitrile (2 ml), potassium carbonate (0.01 g) and 1-bromo-2-methoxyethane (0.01 g). MS m/z (rel. intensity, 70 eV) 279 (M+, 1), 235 (16), 234 (bp), 163 (3), 133 (4).

EXAMPLE 62

1-[3-(1-ALLYLPIPERIDIN-4-YL)-2-FLUOROPHENYL]-2,2,2-TRIFLUOROETHANONE

Preparation according to Example 1: 2,2,2-trifluoro-1-(2-fluoro-3-piperidin-4-ylphenyl)ethanone (0.01 g), acetonitrile (2 ml), potassium carbonate (0.01 g) and allylbromide (0.01 g). MS m/z (rel. intensity, 70 eV) 315 (M+, 60), 314 (82), 288 (bp), 286 (31), 96 (36).

EXAMPLE 63

2,2,2-TRIFLUORO-1-{2-FLUORO-3-[1-(2-METHOXYETHYL)PIPERIDIN-4-YL]PHENYL}ETHANONE

Preparation according to Example 1: 2,2,2-trifluoro-1-(2-fluoro-3-piperidin-4-ylphenyl)ethanone (0.01 g), acetonitrile (2 ml), potassium carbonate (0.01 g) and 1-bromo-2-methoxyethane (0.01 g). MS m/z (rel. intensity, 70 eV) 333 (M+, 1), 289 (15), 288 (bp), 264 (4), 148 (6).

EXAMPLE 64

1-[3-(1-ETHYLPIPERIDIN-4-YL)-2-FLUOROPHENYL]-2,2,2-TRIFLUOROETHANONE

Preparation according to Example 1: 2,2,2-trifluoro-1-(2-fluoro-3-piperidin-4-ylphenyl)ethanone (0.70 g, 2.54 mmol), acetonitrile (30 ml), potassium carbonate (0.35 g) and 2-iodoethane (0.40 g, 2.54 mmol). Yield: 0.21 g (27%). The amine was converted to the fumaric acid salt and recrystallized from ethanol/diethyl ether: M.p. 109-110° C. MS m/z (rel. intensity, 70 eV) 303 (M+, 13), 302 (10), 289 (16), 288 (bp), 234 (7).

EXAMPLE 65

2,2,2-TRIFLUORO-1-[2-FLUORO-3-(1-PROPYLPIPERIDIN-4-YL)PHENYL]ETHANONE

Preparation according to Example 1: 2,2,2-trifluoro-1-(2-fluoro-3-piperidin-4-ylphenyl)ethanone (0.01 g), acetonitrile (2 ml), potassium carbonate (0.01 g) and 1-iodopropane (0.01 g). MS m/z (rel. intensity, 70 eV) 317 (M+, 3), 289 (15), 288 (bp), 248 (4), 109 (6).

EXAMPLE 66

2,2,2-TRIFLUORO-1-{2-FLUORO-3-[1-(2-METHOXYETHYL)PIPERIDIN-4-YL]PHENYL}ETHANOL

Preparation according to Example 1: 2,2,2-trifluoro-1-(2-fluoro-3-piperidin-4-ylphenyl)ethanol (0.01 g), acetonitrile (2 ml), potassium carbonate (0.01 g) and 1-bromo-2-methoxyethane (0.01 g). MS m/z (rel. intensity, 70 eV) 335 (M+, 1), 291 (15), 290 (bp), 207 (4), 149 (7).

EXAMPLE 67

1-[3-(1-ETHYLPIPERIDIN-4-YL)-2-FLUOROPHENYL]-2,2,2-TRIFLUOROETHANOL

Preparation according to Example 1: 2,2,2-trifluoro-1-(2-fluoro-3-piperidin-4-ylphenyl)ethanol (0.01 g), acetonitrile (2 ml), potassium carbonate (0.01 g) and iodoethane (0.01 g). MS m/z (rel. intensity, 70 eV) 305 (M+, 17), 304 (13), 291 (15), 290 (bp), 149 (5).

EXAMPLE 68

2,2,2-TRIFLUORO-1-[2-FLUORO-3-(1-PROPYLPIPERIDIN-4-YL)PHENYL]ETHANOL

Preparation according to Example 1: 2,2,2-trifluoro-1-(2-fluoro-3-piperidin-4-ylphenyl)ethanol (0.01 g), acetonitrile (2 ml), potassium carbonate (0.01 g) and iodopropane (0.01 g). MS m/z (rel. intensity, 70 eV) 319 (M+, 4), 291 (14), 290 (bp), 220 (3), 149 (3).

EXAMPLE 69

3-(1-ETHYLPIPERIDIN-4-YL)PHTHALONITRILE

Preparation according to Example 31: 1-ethyl-4-[2-fluoro-3-(methylsulfonyl)phenyl]-piperidine (1.06 g, 3.72 mmol), N,N-dimethylformamide (30 ml), sodium cyanide (0.7 g, 14.0 mmol) and 18-crown-6-ether (5 mg). Yield: 0.35 g. MS m/z (relative intensity, 70 eV) 239 (M+, 3), 225 (17), 224 (bp), 154 (6), 71 (5).

EXAMPLE 70

1-ALLYL-4-[2-FLUORO-3-(TRIFLUOROMETHYL)PHENYL]PIPERIDINE

Preparation according to Example 1: 4-[2-fluoro-3-(trifluoromethyl)phenyl]piperidine (0.45 g, 1.82 mmol), acetonitrile (20 ml), potassium carbonate (0.6 g, 1.1 mmol) and allyl bromide (0.16 ml, 2.0 mmol). Yield: 0.42 g (80%). The amine was converted to the hydrochloric acid salt and recrystallized

EXAMPLE 71

4-[2-FLUORO-3-(TRIFLUOROMETHYL)PHENYL]-1-PROPYLPIPERIDINE

A mixture of 4-[2-fluoro-3-(trifluoromethyl)phenyl]-1-propyl-1,2,3,6-tetrahydropyridine (5.0 g, 17.4 mmol), palladium on carbon (0.4 g) and hydrochloric acid (0.5 ml, conc) in methanol (30 ml) was hydrogenated at 50 psi for 15 h under hydrogen. The reaction mixture was filtered through a pad of celite and the filtrate was concentrated and evaporated to dryness to give 4.7 g of crude product. Purification by flash column chromatography (Isooctane/ethylacetate, 1:1) gave the title compound (2.57 g, 51%). The amine was converted to the hydrochloric acid salt and recrystallized from ethanol/diethyl ether: M.p. 258-260° C. MS m/z (relative intensity, 70 eV) 289 (M+, 4), 261 (16), 260 (bp), 177 (6) 70 (15).

Synthesis of intermediates used in the above Examples is described in the preparations below.

Preparation 1

4-[2-FLUORO-3-(TRIFLUOROMETHYL)PHENYL]-1-PROPYLPIPERIDIN-4-OL

To a solution of 3-Bromo-2-fluorobenzotrifluoride (9.0 g, 37 mmol) in dry tetrahydrofuran (100 ml), under nitrogen, was added dropwise at −78° C., n-butyllithium (2.5 M in hexane, 16.2 ml, 40.5 mmol). The mixture was stirred for 1 h after which a solution of newly distilled 4-propyl-1-piperidone (5.2 g, 37 mmol) in dry tetrahydrofuran (50 ml) was added dropwise. The resulting mixture was stirred at −78° C. for 30 min and then brought to ambient temperature. Water (100 ml) was added and the mixture was extracted with ethylacetate (3×100 ml). The combined organic phases was dried (MgSO$_4$), filtered and evaporated to dryness. The oily residue was purified by flash column chromatography (ethylacetate/methanol, 1:1) to give the title compound (8.0 g). MS m/z (rel. intensity, 70 eV) 305 (M+, 5), 276 (bp), 258 (35), 191 (21), 185 (17).

Preparation 2

4-[2-FLUORO-3-(TRIFLUOROMETHYL)PHENYL]-1-PROPYL-1,2,3,6-TETRAHYDROPYRIDINE

A solution of 4-[2-fluoro-3-(trifluoromethyl)phenyl]-1-propylpiperidin-4-ol (8.0 g, 26 mmol) in trifluoroacetic acid (80 ml) was heated at reflux for 20 h. The mixture was poured on to ice and was basified with 10 M sodium hydroxide. The mixture was extracted with ethylacetate (3×100 ml) and the combined organic phases was dried (MgSO$_4$), filtered and evaporated to dryness. The residue was purified by flash column chromatography (ethylacetate/methanol, 1:1) to give the title compound (5.6 g). MS m/z (rel. intensity, 70 eV) 287 (M+, 22), 259 (16), 258 (bp), 177 (10), 147 (10).

Preparation 3

1-BROMO-2-CHLORO-3-(METHYLTHIO)BENZENE

To a solution of 1,3-dibromo-2-chlorobenzene (3.4 g, 12.6 mmol) in dry diethyl ether (60 ml), under nitrogen, at −78° C., was added dropwise n-butyllithium (2.5 M in hexane, 5.0 ml, 12.6 mmol). The mixture was stirred for 1 h after which dimethyldisulfide (1.0 ml, 13.9 mmol) was added dropwise. The resulting mixture was stirred at −78° C. for 30 min and then brought to ambient temperature. Water (100 ml) was added and the mixture was extracted with ethylacetate (3×100 ml). The combined organic phases was dried (MgSO$_4$), filtered and evaporated to dryness. The residue was purified by flash column chromatography (isooctane) to give the title compound (1.23 g). MS m/z (rel. intensity, 70 eV) 240 (M+, 28), 238 (M+, bp), 236 (71), 205 (29), 142 (27).

Preparation 4

1-BROMO-2-CHLORO-3-(METHYLSULFONYL)-BENZENE

To a mixture of 1-bromo-2-chloro-3-(methylthio)benzene (1.23 g, 5.2 mmol) and sodium periodate (3.3 g, 15.6 mmol) in carbon tetrachloride/acetonitrile/water (1:1:2, 30 ml) was added ruthenium trichloride (1 mg, 0.05 mol %). The resulting mixture was stirred at ambient temperature for 20 min after which aqueous sodium carbonate (10%, 50 ml) was added and the mixture was extracted with ethylacetate (3×100 ml). The combined organic phases was dried (MgSO$_4$), filtered and evaporated to dryness to give the title compound (1.4 g). MS m/z (rel. intensity, 70 eV) 270 (M+, 66), 268 (M+, 48), 208 (65), 190 (77), 75 (bp).

Preparation 5

4-[2-CHLORO-3-(METHYLSULFONYL)PHENYL]-PYRIDINE

To a mixture of 1-bromo-2-chloro-3-(methylsulfonyl)benzene (1.3 g, 4.8 mmol), 1-pyridyl-4-boronic acid (0.78 g, 6.3 mmol) and sodium carbonate (0.98 g, 12 mmol) in toluene/ethanol (1:1, 60 ml) under nitrogen, was added palladium tetrakis (0.7 g, 0.48 mmol). The mixture was heated at reflux for 48 h, cooled to ambient temperature after which water (50 ml) and ethylacetate (100 ml) was added. The organic layer was separated and the aqueous phase was extracted with ethylacetate (2×50 ml). The combined organic phases was evaporated to dryness and dissolved in aqueous hydrochloric acid (10%, 50 ml). The solution was washed with diethyl ether (2×40 ml), basified with 2 M sodium hydroxide and extracted with ethylacetate (2×50 ml). The combined organic phases was dried (MgSO$_4$) and evaporated to dryness to give the title compound (1.0 g). MS m/z (rel. intensity, 70 eV) 269 (M+, 39), 267 (M+, bp), 188 (67), 153 (47), 126 (82).

Preparation 6

4-[2-CHLORO-3-(METHYLSULFONYL)PHENYL]-1-PROPYL-1,2,3,6-TETRAHYDROPYRIDINE

To neat 4-[2-chloro-3-(methylsulfonyl)phenyl]-pyridine (1.0 g, 3.8 mmol) was added 1-iodopropane (5 ml) and the resulting mixture was heated at 100° C. for 2 h. Excess 1-iodopropane was evaporated under reduced pressure and ethanol (60 ml) was added. The mixture was cooled to −20° C. and sodium borohydride (1.3 g, 38 mmol) was added in portions. The resulting mixture was stirred for 1 h, after which aqueous sodium carbonate (10%, 50 ml) was added. The aqueous phase was extracted with ethylacetate (3×100 ml) and the combined organic phases was dried (MgSO$_4$), filtered and evaporated to dryness. The residue was purified by flash column chromatography (ethylacetate/methanol, 1:1) to give the title compound (0.5 g). MS m/z (rel. intensity, 70 eV) 313 (M+, 18), 286 (39), 285 (17), 284 (bp), 128 (12).

Preparation 7

1-BROMO-2-METHOXY-3-(TRIFLUOROM-ETHYL)-BENZENE

To a solution of 3-bromo-2-fluorobenzotrifluoride (1.0 g, 4.1 mmol) in methanol (5 ml) was added a solution of sodium methoxide in methanol (30%, 0.73 ml, 4.1 mmol). The mixture was heated under microwave radiation to 150° C. for 10 min. The reaction mixture was poured into water and extracted with ethylacetate (3×50 ml). The combined organic phases was dried (MgSO$_4$), filtered and evaporated to dryness to give the title compound (0.89 g). MS m/z (rel. intensity, 70 eV) 256 (M+, 87), 254 (M+, 89), 239 (26), 211 (24), 132 (bp).

Preparation 8

4-[2-METHOXY-3-(TRIFLUOROMETHYL)PHE-NYL]-PYRIDINE

Preparation according to preparation 5: 1-bromo-2-methoxy-3-(trifluoromethyl)benzene (0.89 g, 3.5 mmol), toluene (30 ml), ethanol (30 ml), 1-pyridyl-4-boronic acid (0.56 g) and sodium carbonate (0.71 g), palladium tetrakis (0.51 g). Yield: 0.42 g. MS m/z (rel. intensity, 70 eV) 253 (M+, bp), 238 (29), 233 (18), 183 (31), 133 (19).

Preparation 9

4-[2-METHOXY-3-(TRIFLUOROMETHYL)PHE-NYL]-PIPERIDINE

To a solution of 4-[2-methoxy-3-(trifluoro-methyl)phenyl]pyridine (0.42 g, 1.66 mmol) in methanol (10 ml), was added platinum oxide (0.10 g) and hydrochloric acid (0.1 ml, conc) and the reaction mixture was hydrogenated at 50 psi for 1 h under hydrogen. Filtration through a pad of celite and evaporation of the filtrate gave 0.48 g of crude product as the hydrochloric acid salt. The salt was dissolved in aqueous sodium carbonate (10%, 50 ml) and extracted with ethylacetate (3×50 ml). The combined organic phases was dried (MgSO$_4$), filtered and evaporated to dryness to give the title compound (0.38 g). MS m/z (relative intensity, 70 eV) 260 (M+, 2), 258 (M+, 7), 229 (14), 228 (bp) 59 (15).

Preparation 10

1-BROMO-2-METHYL-3-(METHYLTHIO)BEN-ZENE

To a solution of 1-bromo-3-fluoro-2-methylbenzene (2.0 g, 10.6 mmol) in N,N-dimethylformamide (10 ml) was added sodium methanethiolate (0.85 g, 11.7 mmol) and the mixture was stirred for 15 min at 150° C. After cooling, aqueous sodium carbonate (10%, 50 ml) was added and the phases were separated. The aqueous phase was extracted with ethylacetate (2×50 ml) and the combined organic phases was dried (MgSO4) and evaporated under reduced pressure to give an oil. The residue was purified by flash column chromatography (isooctane) to give the title compound (1.33 g). MS m/z (relative intensity, 70 eV) 218 (M+, 98), 216 (M+, 92), 202 (26), 200 (26), 122 (bp), 121 (56).

Preparation 11

1-BROMO-2-METHYL-3-(METHYLSULFO-NYL)-BENZENE

Preparation according to preparation 4: 1-bromo-2-methyl-3-(methylthio)benzene (1.33 g), carbon tetrachloride (8 ml), acetonitrile (8 ml), water (16 ml), sodium periodate (3.9 g), ruthenium trichloride (1 mg). Yield: 1.6 g. MS m/z (rel. intensity, 70 eV) 250 (M+, 69), 248 (M+, 67), 169 (49), 90 (63), 89 (bp).

Preparation 12

4-[2-METHYL-3-(METHYLSULFONYL)PHE-NYL]-PYRIDINE

Preparation according to preparation 5: 1-bromo-2-methyl-3-(methylsulfonyl)benzene (1.1 g, 4.5 mmol), toluene (30 ml), ethanol (30 ml), 1-pyridyl-4-boronic acid (0.73 g) and sodium carbonate (0.91 g), palladium tetrakis (0.65 g). Yield: 0.40 g. MS m/z (rel. intensity, 70 eV) 247 (M+, 96), 246 (51), 168 (53), 167 (bp), 139 (51).

Preparation 13

4-[2-METHYL-3-(METHYLSULFONYL)PHE-NYL]-PIPERIDINE

Preparation according to preparation 9: 4-[2-methyl-3-(methylsulfonyl)phenyl]pyridine (0.4 g, 1.6 mmol), methanol (10 ml), platinum oxide (0.10 g), hydrochloric acid (0.1 ml, conc). Yield: 0.41 g. MS m/z (rel. intensity, 70 eV) 247 (M+, 96), 246 (51), 168 (53), 167 (bp), 139 (51).

Preparation 14

4-[3-FLUORO)-2-(TRIFLUOROMETHYL)PHE-NYL]-1-PROPYLPIPERIDIN-4-OL

Preparation according to preparation 1: 1-bromo-3-fluoro-2-(trifluoromethyl)benzene (2.5 g, 10.3 mmol), dry diethyl ether (100 ml), n-butyllithium (2.5 M in hexane, 4.0 ml, 10.3 mmol), 4-propyl-1-piperidone (1.45 g, 10.3 mmol). Yield: 2.98 g. MS m/z (rel. intensity, 70 eV) 305 (M+, 7), 277 (14), 276 (bp), 258 (57), 163 (7).

Preparation 15

4-[3-FLUORO)-2-(TRIFLUOROMETHYL)PHE-NYL]-1-PROPYL-1,2,3,6-TETRAHYDROPYRI-DINE

Preparation according to preparation 2: 4-[3-fluoro-2-(trifluoromethyl)phenyl]-1-propylpiperidin-4-ol (2.98 g, 9.8 mmol), hydrochloric acid (40 ml, conc). Yield: 2.37 g. MS m/z (rel. intensity, 70 eV) 305 (M+, 7), 277 (14), 276 (bp), 258 (57), 163 (7).

Preparation 16

4-[3-FLUORO-2-(TRIFLUOROMETHYL)PHE-NYL]-1-PROPYLPIPERIDINE

To a solution of 4-[3-fluoro-2-(trifluoromethyl)phenyl]-1-propyl-1,2,3,6-tetrahydro pyridine (1.73 g, 6.0 mmol) in ethanol (30 ml) was added Raney nickel (slurry in water, 10 ml) and the reaction mixture was hydrogenated under hydrogen (50 psi) for 2 days. Filtration through a pad of celite and evaporation of the filtrate gave 1.35 g of crude product. MS m/z (relative intensity, 70 eV) 289 (M+, 4), 261 (16), 260 (bp), 176 (6) 70 (20).

Preparation 17

3-(1-ETHYLPIPERIDIN-4-YL)-2-FLUOROBENZONITRILE

To a solution of 3-(1-ethylpiperidin-4-yl)-2-fluorobenzamide (0.46 g, 1.83 mmol) in dry N,N-dimethylformamide (4 ml) was added freshly distilled phosphoryl trichloride (0.42 ml, 4.57 mmol) and the reaction mixture was stirred for 1 h. The solution was poured on to ice and was made basic by addition of aqueous sodium carbonate (10%, 50 ml). Ethyl acetate (50 ml) was added and the phases were separated. The aqueous phase was extracted with ethyl acetate (2×50 ml) and the combined organic phases was dried (MgSO4) and evaporated under reduced pressure to give an oil. Purification by flash column chromatography (ethyl acetate/methanol, 1:1) gave the title compound: 0.32 g (75%). The amine was converted to the oxalic acid salt and recrystallized from ethanol/diethyl ether: M.p. 156-158° C. MS m/z (relative intensity, 70 eV) 232 (M+, 12), 218 (14), 217 (bp), 147 (10), 134 (13).

Preparation 18

4-[2-FLUORO)-3-(TRIFLUOROMETHYL)PHENYL]-1-PROPYLPIPERIDINE

A mixture of 4-[2-fluoro-3-(trifluoromethyl)phenyl]-1-propyl-1,2,3,6-tetrahydropyridine (5.0 g, 17.4 mmol), palladium on carbon (0.4 g) and hydrochloric acid (0.5 ml, conc) in methanol (30 ml) was hydrogenated at 50 psi for 15 h under hydrogen. The reaction mixture was filtered through a pad of celite and the filtrate was concentrated and evaporated to dryness to give 4.7 g of crude product. Purification by flash column chromatography (Isooctane/ethylacetate, 1:1) gave the title compound (2.57 g, 51%). The amine was converted to the hydrochloric acid salt and recrystallized from ethanol/diethyl ether: M.p. 258-260° C. MS m/z (relative intensity, 70 eV) 289 (M+, 4), 261 (16), 260 (bp), 177 (6) 70 (15).

Preparation 19

TERT-BUTYL 4-[2-FLUORO-3-(TRIFLUOROMETHOXY)PHENYL]-4-HYDROXYPIPERIDINE-1-CARBOXYLATE

Preparation according to preparation 30:1-fluoro-2-(trifluoromethoxy)benzene (10 g, 55.5 mmol), dry tetrahydrofurane (30 ml), lithium diisopropylamide (2 M in hexane, 31 ml, 62 mmol) and 4-boc-1-piperidone (13.3 g, 66.6 mmol). Yield: 11.5 g. MS m/z (rel. intensity, 70 eV) 379 (M+, 1), 306 (7), 305 (14), 261 (10), 57 (bp).

Preparation 20

4-[2-FLUORO-3-(TRIFLUOROMETHOXY)PHENYL]-1,2,3,6-TETRAHYDROPYRIDINE

Preparation according to preparation 31: tert-butyl 4-[2-fluoro-3-(trifluoromethoxy)-phenyl]-4-hydroxypiperidine-1-carboxylate (11.5 g, 30.3 mmol), polyphosphoric acid (15 ml). Yield: 3.33 g. MS m/z (rel. intensity, 70 eV) 261 (M+, bp), 232 (17), 193 (24), 147 (64), 82 (86).

Preparation 21

3-PIPERAZIN-1-YL-2-(TRIFLUOROMETHYL)-BENZONITRILE

A solution of 3-fluoro-2-(trifluoromethyl)benzonitrile (1.2 g, 6.3 mmol) and piperazine (0.72 g, 8.4 mmol) in acetonitrile (6 ml) was heated under microwave radiation at 150° C. for 15 minutes. The reaction mixture was poured into water (50 ml) and the aqueous phase was extracted with ethylacetate (3×50 ml). The combined organic phases was dried (MgSO4), filtered and evaporated to dryness. Purification by flash column chromatography (ethylacetate/methanol, 1:1) gave the title compound: 1.1 g. MS m/z (rel. intensity, 70 eV) 255 (M+, 16), 214 (11), 213 (bp), 171 (8), 151 (7).

Preparation 22

1-[2-FLUORO-3-(TRIFLUOROMETHYL)PHENYL]-PIPERAZINE

To a solution of 3-bromo-2-fluorobenzotrifluoride (1.72 g, 7.1 mmol) in toluene (50 ml) under nitrogen, was added piperazine (0.89 g, 10.6 mmol), potassium tert-butoxide (0.95 g, 9.9 mmol), bis(dibenzylideneacetone)palladium(0) (0.19 g, 0.21 mmol) and (+/−)-1,1'-binaphthyl-2,2'-diyl hydrogen phosphate (0.13 g, 0.21 mmol). The resulting mixture was heated at 80° C. for 20 h. Filtration through a pad of celite and evaporation of the filtrate gave 2.1 g of crude product. The residue was purified by flash column chromatography (ethylacetate/methanol, 1:1) to give the title compound (0.96 g). MS m/z (rel. intensity, 70 eV) 248 (M+, 23), 207 (10), 206 (bp), 190 (17), 163 (8).

Preparation 23

1-BROMO-2-FLUORO-3-(METHYLTHIO)BENZENE

To a solution of 1-bromo-2-fluorobenzene (2.0 g, 11.4 mmol) in dry tetrahydrofuran (50 ml) under nitrogen, at −78° C. was added lithium diisopropylamide (2.5 M in hexane, 6.28 ml, 15.4 mmol). The mixture was stirred for 5 minutes after which dimethyldisulfide (0.92 ml, 15.4 mmol) was added and the stirring was continued at −78° C. for an additional hour. The reaction mixture was brought to ambient temperature and aqueous sulfuric acid (10%, 50 ml) was added. The phases were separated and the aqueous phase extracted with ethylacetate (3×100 ml). The combined organic phases was dried (MgSO4) and evaporated to dryness to give an oil. The residue was purified by flash column chromatography (isooctane) to give the title compound (1.26 g). MS m/z (relative intensity, 70 eV) 222 (M+, bp), 220 (M+, 91), 189 (24), 187 (25), 126 (97).

Preparation 24

TERT-BUTYL 4-[2-FLUORO)-3-(METHYLTHIO)-PHENYL]-4-HYDROXYPIPERIDINE-1-CARBOXYLATE

To a solution of 1-bromo-2-fluoro-3-(methylthio)benzene (1.1 g, 4.95 mmol) in dry tetrahydrofuran (50 ml), under nitrogen, at −78° C. was added dropwise n-butyllithium (2.5 M in hexane, 2.1 ml, 5.2 mmol). The mixture was stirred for 30 min at −78° C. and then brought to −20° C. for 2 min and cooled again to −78° C. To the resulting mixture at −78° C., a solution of 4-Boc-1-piperidone (1.04 g, 5.2 mmol) in dry tetrahydrofuran (50 ml) was added dropwise. The mixture was stirred at −78° C. for 10 min and then brought to ambient temperature. The reaction mixture was quenched with saturated aqueous ammonium chloride (100 ml) and extracted with ethylacetate (3×100 ml). The combined organic phases was dried, concentrated, and purified by flash column chromatography (isooctane/ethylacetate 2:1) to give the title compound (1.25 g). MS m/z (rel. intensity, 70 eV) 341 (M+, 11), 285 (24), 267(14), 196 (11), 57 (bp).

Preparation 25

4-[2-FLUORO-3-(METHYLTHIO)PHENYL]-1,2,3,6-TETRAHYDROPYRIDINE

Preparation according to preparation 2: Tert-butyl 4-[2-fluoro-3-(methylthio)-phenyl]-4-hydroxy-piperidine-1-carboxylate (2.0 g, 5.86 mmol), trifluoroacetic acid (20 ml). Yield: 1.42 g. MS m/z (rel. intensity, 70 eV) 223 (M+, bp), 222 (32), 147 (61), 146 (47), 133 (27).

Preparation 26

METHYL 4-[2-FLUORO)-3-(METHYLTHIO)PHENYL]-3,6-DIHYDROPYRIDINE-1(2H)-CARBOXYLATE

To a solution of 4-[2-fluoro-3-(methylthio)phenyl]-1,2,3,6-tetrahydropyridine (1.35 g, 6.05 mmol) and triethyl amine (1.2 ml, 7.2 mmol) in methylen chloride (20 ml) at 0° C., a solution of methyl chloroformate (0.49 g, 6.6 mmol) in methylen chloride (5 ml), was added dropwise. The mixture was stirred for 15 min at 0° C. and for 1 h at ambient temperature. The reaction was quenched with aqueous sodium carbonate (10%, 50 ml), the phases were separated and the aqueous phase was extracted with methylen chloride (3×50 ml). The combined organic phases was dried (MgSO$_4$), filtered and evaporated to dryness to give the title compound (0.95 g). MS m/z (rel. intensity, 70 eV) 281 (M+, 65), 267 (16), 266(bp), 147 (27), 146 (25).

Preparation 27

METHYL 4-[2-FLUORO-3-(METHYLSULFONYL)-PHENYL]-3,6-DIHYDROPYRIDINE-1(2H)-CARBOXYLATE

To a solution of methyl 4-[2-fluoro-3-(methylthio)phenyl]-3,6-dihydro-pyridine-1(2H)-carboxylate (0.9 g, 3.2 mmol) in methylen chloride (50 ml) at 0° C., m-chloroperbenzoic acid (1.21 g, 7.0 mmol) was added in portions over a period of 30 min. The mixture was stirred at 0° C. for 1.5 h, and then at ambient temperature for an additional hour. Aqueous sodium carbonate (10%, 100 ml) was added and the phases were separated. The aqueous phase was extracted with methylen chloride (3×50 ml) and the combined organic phases was washed with brine (50 ml), dried (MgSO$_4$) and evaporated to dryness to give the title compound (1.24 g). MS m/z (rel. intensity, 70 eV) 313 (M+, 47), 298 (bp), 254(25), 147 (22), 146 (26).

Preparation 28

METHYL 4-[2-FLUORO-3-(METHYLSULFONYL)-PHENYL]PIPERIDINE-1-CARBOXYLATE

Preparation according to preparation 18: Methyl 4-[2-fluoro-3-(methylsulfonyl)-phenyl]-3,6-dihydropyridine-1(2H)-carboxylate (1.45 g, 4.6 mmol), palladium on carbon (0.2 g) and hydrochloric acid (0.5 ml, conc). Yield: 0.76 g. MS m/z (relative intensity, 70 eV) 315 (M+, 41), 256 (bp), 236 (54), 141 (43) 114 (50).

Preparation 29

4-[2-FLUORO-3-(METHYLSULFONYL)PHENYL]-PIPERIDINE

To a solution of methyl 4-[2-fluoro-3-(methylsulfonyl)-phenyl]piperidine-1-carboxylate (0.7 g, 2.2 mmol) in ethanol (4 ml), hydrochloric acid (3 M, 10 ml) was added and the mixture was heated at reflux for 24 h. The ethanol was evaporated and the aqueous residue was basified with sodium hydroxide (5 M) and extracted with ethylacetate (3×50 ml). The combined organic phases was washed with brine (50 ml), dried (MgSO$_4$) and evaporated to dryness to give the title compound (0.5 g, 91%). MS m/z (relative intensity, 70 eV) 257 (M+, 6), 237 (95), 208 (83), 173 (bp) 130 (69).

Preparation 30

4-[2-FLUORO-3-(TRIFLUOROMETHOXY)PHENYL]-1-PROPYLPIPERIDIN-4-OL

To a solution of 1-fluoro-2-(trifluoromethoxy)benzene (1.22 g, 6.77 mmol) in dry tetrahydrofurane (30 ml) at −78° C., under nitrogen, lithium diisopropylamide (2.5 M in hexane, 3.0 ml, 7.45 mmol) was added dropwise. The mixture was stirred for 1 h after which a solution of newly distilled 4-propyl-1-piperidone (0.96 g, 6.77 mmol) in dry tetrahydrofuran (20 ml) was added dropwise. The resulting mixture was stirred at −78° C. for 30 min and then brought to ambient temperature. Water (100 ml) was added and the mixture was extracted with ethylacetate (3×100 ml). The combined organic phases was dried (MgSO$_4$), filtered and evaporated to dryness. The oily residue was purified by flash column chromatography (ethylacetate/methanol, 1:1) to give the title compound (0.83 g). MS m/z (rel. intensity, 70 eV) 321 (M+, 5), 293 (14), 292 (bp), 274 (25), 207 (10).

Preparation 31

4-[2-FLUORO-3-(TRIFLUOROMETHOXY)PHENYL]-1-PROPYL-1,2,3,6-TETRAHYDROPYRIDINE

A mixture of 4-[2-fluoro-3-(trifluoromethoxy)phenyl]-1-propyl-piperidin-4-ol (0.83 g, 2.6 mmol) and polyphosphoric acid (10 ml) was heated at 100° C. for 2 h. The mixture was poured on to ice and was basified with 5 M sodium hydroxide. The mixture was extracted with ethylacetate (3×100 ml) and the combined organic phases was dried (MgSO$_4$), filtered and evaporated to dryness to give the title compound (0.62 g). MS m/z (rel. intensity, 70 eV) 303 (M+, 24), 275 (14), 274 (bp), 147 (7), 133 (6).

Preparation 32

4-[2-FLUORO-3-(TRIFLUOROMETHOXY)PHENYL]-1-PROPYL-PIPERIDINE

Preparation according to preparation 18: 4-[2-fluoro-3-(trifluoromethoxy)phenyl]-1-propyl-1,2,3,6-tetrahydro-pyridine (0.55 g, 1.8 mmol), palladium on carbon (0.09 g) and hydrochloric acid (0.5 ml, conc). Yield: 0.22 g (40%). The amine was converted to the hydrochloric acid salt and recrystallized from ethanol/diethyl ether: M.p. 221-222° C. MS m/z (relative intensity, 70 eV) 305 (M+, 3), 277 (14), 276 (bp), 233 (6) 193 (8).

Preparation 33

4-[2-FLUORO-3-(TRIFLUOROMETHOXY)PHENYL]PIPERIDINE

Preparation according to preparation 18: 4-[2-fluoro-3-(trifluoromethoxy)phenyl]-1,2,3,6-tetrahydropyridine (3.33 g, 12.7 mmol), palladium on carbon (0.35 g), hydrochloric acid (0.5 ml), methanol (30 ml). Yield: 2.68 g. MS m/z (relative intensity, 70 eV) 263 (M+, 39), 262 (27), 206 (8), 178 (7) 56 (bp).

Preparation 34

4-[2-METHOXY-3-(TRIFLUOROMETHOXY)PHENYL]-1-PROPYLPIPERIDINE

To a solution of 4-[2-fluoro-3-(trifluoromethoxy)phenyl]-1-propylpiperidine (1.92 g, 6.3 mmol) in N,N-dimethylformamide (20 ml) was added a solution of sodium methoxide in methanol (30%, 3 ml) and the mixture was heated to 150° C. for 1 h. Water (50 ml) and ethyl acetate (50 ml) was added and the phases were separated. The aqueous phase was extracted with ethyl acetate (2×50 ml) and the combined organic phases was dried (MgSO4) and evaporated under reduced pressure to give an oil. The residue was purified by flash column chromatography (ethyl acetate/methanol, 1:1) to give the title compound (1.32 g). MS m/z (rel. intensity, 70 eV) 317 (M+, 6), 289 (17), 288 (bp), 204 (6), 175 (8).

Preparation 35

3-BROMO-2-FLUORO-N,N-DIMETHYLBENZENESULFONAMIDE 3-bromo-2-fluorobenzenethiol (1.9 g, 9.2 mmol), sodium periodate (4.8 g, 22.9 mmol) and ruthenium trichloride (5 mg) in acetonitrile (60 ml) was stirred at 0° C. for 5 min. after which sulfonyl chloride (1.9 ml, 22.9 mmol) was added dropwise. The mixture was stirred for an additional hour and ethyl acetate (50 ml) and aqueous sodium carbonate (10%, 50 ml) was added. The phases were separated and the aqueous phase was extracted with ethyl acetate (2×50 ml). To the combined organic phase, dimethylamine (40% in water, 10 ml) was added and the mixture was stirred for 1 h. Evaporation of the solvents and purification by flash chromatography yielded the title compound (1.1 g). MS m/z (rel. intensity, 70 eV) 283 (M+, 47), 281 (M+, 44), 239 (32), 73 (59), 94 (bp).

Preparation 36

2-FLUORO-N,N-DIMETHYL-3-PYRIDIN-4-YL-BENZENESULFONAMIDE

Preparation according to preparation 5: 3-bromo-2-fluoro-N,N-dimethylbenzene-sulfonamide (1.2 g, 3.54 mmol), toluene (30 ml), ethanol (30 ml), 1-pyridyl-4-boronic acid (0.57 g, 4.25 mmol), sodium carbonate (0.8 g), palladium tetrakis (0.55 g). Yield: 0.51 g. MS m/z (rel. intensity, 70 eV) 280 (M+, bp), 173 (95), 172 (90), 145 (32), 125 (40).

Preparation 37

3-(1-ETHYL-1,2,3,6-TETRAHYDROPYRIDIN-4-YL)-2-FLUORO-N,N-DIMETHYLBENZENE-SULFONAMIDE

Preparation according to preparation 6: 2-fluoro-N,N-dimethyl-3-pyridin-4-ylbenzene sulfonamide (0.59 g, 2.11 mmol), 1-iodoethane (3 ml), ethanol (40 ml), sodium borohydride (0.4 g, 10.5 mmol). Yield: 0.27 g. MS m/z (rel. intensity, 70 eV) 312 (M+, bp), 311 (33), 297 (93), 146 (36), 110 (32).

Preparation 38

1-BROMO-2-FLUORO-3-[(TRIFLUOROMETHYL)THIO]BENZENE 1-bromo-3-[(3-bromo-2-fluorophenyl)dithio]-2-fluorobenzene (1.23 g, 2.98 mmol) was dissolved in dry tetrahydrofuran (40 ml) and trifluoromethyltrimethylsilane (2M in THF) was added under nitrogen atmosphere. The solution was cooled to −10° C. and tris(dimethylamino)sulfur(trimethylsilyl)difluoride (3 ml, 6.0 mmol) was added in portions. The mixture was warmed to room temperature and stirred for 12 h. Water (50 ml) and ethyl acetate (50 ml) was added and the phases were separated. The aqueous phase was extracted with ethyl acetate (2×50 ml) and the combined organic phases was dried (MgSO4) and evaporated under reduced pressure to give an oil. The residue was purified by flash column chromatography (isooctane/ethyl acetate, 1:1) to give the title compound (0.45 g). MS m/z (rel. intensity, 70 eV) 276 (M+, 62), 274 (M+, 58), 207 (35), 205 (31), 126 (bp).

Preparation 39

1-BROMO-2-FLUORO-3-[(TRIFLUOROMETHYL)SULFONYL]BENZENE

Preparation according to preparation 4: 1-bromo-2-fluoro-3-[(trifluoromethyl)thio]benzene (0.37 g), carbon tetrachloride (4 ml), acetonitrile (4 ml), water (8 ml), sodium periodate (0.86 g), ruthenium trichloride (1 mg). Yield: 0.3 g. MS m/z (rel. intensity, 70 eV) 308 (M+, 18), 306 (M+, 19), 239 (57), 173 (60), 94 (bp).

Preparation 40

4-{2-FLUORO-3-[(TRIFLUOROMETHYL)SULFONYL]PHENYL}PYRIDINE

Preparation according to preparation 5: 1-bromo-2-fluoro-3-[(trifluoromethyl) sulfonyl]benzene (0.3 g, 0.98 mmol), toluene (20 ml), ethanol (20 ml), 1-pyridyl-4-boronic acid (0.16 g, 1.17 mmol), sodium carbonate (0.22 g), palladium tetrakis (0.15 g). Yield: 0.16 g. MS m/z (rel. intensity, 70 eV) 305 (M+, bp), 236 (64), 172 (79), 145 (35), 125 (36).

Preparation 41

4-{2-FLUORO-3-[(TRIFLUOROMETHYL)SULFONYL]PHENYL}PIPERIDINE

Preparation according to preparation 9: 4-{2-fluoro-3-[(trifluoromethyl)sulfonyl]phenyl}-pyridine (0.16 g, 0.53 mmol), methanol (10 ml), platinum oxide (0.02 g). Yield: 0.11 g. MS m/z (relative intensity, 70 eV) 311 (M+, 2), 291 (47), 164 (92), 130 (62) 69 (bp).

Preparation 42

TERT-BUTYL 4-[2-FLUORO-3-(TRIFLUOROMETHYL)PHENYL]-4-HYDROXYPIPERIDINE-1-CARBOXYLATE

Preparation according to preparation 24: 1-bromo-2-fluoro-3-(trifluoromethyl)benzene (8.0 g, 32.9 mmol), dry diethyl ether (100 ml), n-butyllithium (2.5 M in hexane, 13 ml, 32.9 mmol), 4-boc-1-piperidone (7.8 g, 39.5 mmol). Yield: 8.5 g. MS m/z (rel. intensity, 70 eV) 363 (M+, 2), 289 (44), 245 (28), 191 (23), 57 (bp).

Preparation 43

4-[2-FLUORO-3-(TRIFLUOROMETHYL)PHENYL]-1,2,3,6-TETRAHYDROPYRIDINE

Preparation according to preparation 31: tert-butyl 4-[2-fluoro-3-(trifluoromethyl)phenyl]-4-hydroxypiperidine-1-carboxylate (8.5 g, 23.4 mmol), polyphosphoric acid (30 ml). Yield: 4.2 g. MS m/z (rel. intensity, 70 eV) 245 (M+, bp), 244 (52), 177 (45), 147 (99), 82 (96).

Preparation 44

4-[2-FLUORO-3-(TRIFLUOROMETHYL)PHENYL]PIPERIDINE

Preparation according to preparation 18: 4-[2-fluoro-3-(trifluoromethyl)phenyl]-1,2,3,6-tetrahydropyridine (4.2 g, 17.1 mmol), methanol (20 ml), palladium on carbon (0.42 g) and hydrochloric acid (0.2 ml, conc). Yield: 1.8 g. MS m/z (relative intensity, 70 eV) 247 (M+, 22), 190 (8), 177 (5), 169 (7) 56 (bp).

Preparation 45

4-[2-CHLORO-3-(METHYLSULFONYL)PHENYL]-1-ETHYL-1,2,3,6-TETRAHYDROPYRIDINE

Preparation according to preparation 6: 4-[2-chloro-3-(methylsulfonyl)phenyl]-pyridine (1.77 g, 6.6 mmol), 1-iodoethane (5 ml), ethanol (40 ml), sodium borohydride (2.2 g, 58 mmol). Yield: 0.6 g. MS m/z (rel. intensity, 70 eV) 300 (M+, 24), 299 (M+, 71), 298 (33), 284 (bp), 110 (74).

Preparation 46

1-(BENZYLOXY)-3-BROMO-2-FLUOROBENZENE

To a solution of 3-bromo-2-fluorophenol (1.8 g, 9.42 mmol) in acetone (25 ml) was added sodium carbonate (2.55 g, 20 mmol) and the mixture was stirred for 5 min. Benzylbromide (1.2 ml, 10.3 mmol) was added and the reaction mixture was heated at reflux for 20 h. Water (50 ml) and ethyl acetate (50 ml) was added and the phases were separated. The aqueous phase was extracted with ethyl acetate (2×50 ml) and the combined organic phases was dried (MgSO4) and evaporated under reduced pressure to give an oil. The residue was purified by flash column chromatography (isooctane/ethyl acetate, 5:1) to give the title compound (2.8 g). MS m/z (rel. intensity, 70 eV) 282 (M+, 2), 280 (M+, 2), 163 (2), 161 (2), 91 (bp).

Preparation 47

4-[3-(BENZYLOXY)-2-FLUOROPHENYL]-1-ETHYLPIPERIDIN-4-OL

Preparation according to preparation 1: 1-(benzyloxy)-3-bromo-2-fluorobenzene (2.8 g, 9.96 mmol), dry diethyl ether (100 ml), n-butyllithium (2.5 M in hexane, 5.2 ml, 9.9 mmol), 4-ethyl-1-piperidone (1.5 ml, 10.9 mmol). Yield: 2.1 g. MS m/z (rel. intensity, 70 eV) 329 (M+, 30), 314 (56), 296 (20), 238 (59), 91 (bp).

Preparation 48

3-(1-ETHYL-1,2,3,6-TETRAHYDROPYRIDIN-4-YL)-2-FLUOROPHENOL

Preparation according to preparation 2: 4-[3-(benzyloxy)-2-fluorophenyl]-1-ethylpiperidin-4-ol (1.9 g, 5.77 mmol), trifluoroacetic acid (5 ml). Yield: 1.1 g. MS m/z (rel. intensity, 70 eV) 221 (M+, bp), 220 (43), 206 (95), 163 (10), 110 (14).

Preparation 49

3-(1-ETHYLPIPERIDIN-4-YL)-2-FLUOROPHENOL

Preparation according to preparation 18: 3-(1-ethyl-1,2,3,6-tetrahydropyridin-4-yl)-2-fluorophenol (1.1 g, 4.97 mmol), methanol (20 ml), palladium on carbon (0.26 g) and hydrochloric acid (0.2 ml, conc). Yield: 1.1 g. MS m/z (relative intensity, 70 eV) 223 (M+, 32), 222 (17), 209 (13), 208 (bp) 84 (20).

Preparation 50

3-TRIMETHYLSILYL-2-FLUOROBROMOBENZENE

To a solution of 1-bromo-2-fluorobenzene (2.0 g, 11.42 mmol) and trimethylsilyl chloride (5.79 ml, 45.69 mmol) in dry tetrahydrofurane (30 ml) at −78° C., under nitrogen, lithium diisopropylamide (2 M in hexane, 28 ml, 12.56 mmol) was added dropwise. The mixture was stirred for 1 h and then brought to ambient temperature. 10% Hydrochloric acid (100 ml) was added and the mixture was extracted with ethyl acetate (3×100 ml). The combined organic phases was dried (MgSO4), filtered and evaporated to dryness. The oily residue was purified by flash column chromatography (ethyl acetate/isooctane, 1:1) to give the title compound (2.3 g). MS m/z (rel. intensity, 70 eV) 248 (M+, 22), 246 (20), 151 (96), 105 (bp), 75 (64).

Preparation 51

1-(3-BROMO-2-FLUOROPHENYL)ETHANONE

Aluminium trichloride (1.51 g, 11.3 mmol) in dry methylene chloride (10 ml) was cooled to 0° C. and acetyl chloride (0.80 ml, 11.3 mmol) was added in one portion. The mixture was stirred for 15 min. after which a solution of 3-trimethylsilyl-2-fluorobromobenzene (2.33 g, 9.4 mmol) in dry methylene chloride (10 ml) was added dropwise. The mixture was warmed to ambient temperature and stirred for 2 h. The mixture was kept at ambient temperature in a water bath and aqueous sodium carbonate (10%, 50 ml) was added slowly. The aqueous phase was extracted with ethyl acetate (2×50 ml) and the combined organic phase was dried MgSO4), filtered and evaporated. Purification by flash chromatography (ethyl acetate/isooctane, 1:1) yielded the title compound (1.7 g). MS m/z (rel. intensity, 70 eV) 218 (M+, 32), 216 (M+, 34), 203 (bp), 201 (97), 94 (61).

Preparation 52

1-(2-FLUORO-3-PYRIDIN-4-YLPHENYL)ETHANONE

Preparation according to preparation 5: 1-(3-bromo-2-fluorophenyl)ethanone (2.18 g, 10.0 mmol), toluene (20 ml), ethanol (20 ml), 1-pyridyl-4-boronic acid (1.35 g, 11.0 mmol), sodium carbonate (2.65 g), palladium tetrakis (0.9 g). Yield: 1.14 g. MS m/z (rel. intensity, 70 eV) 215 (M+, 35), 201 (12), 200 (bp), 171 (18), 125 (14).

Preparation 53

4-[2-FLUORO-3-(2-METHYL-1,3-DIOXOLAN-2-YL)PHENYL]PYRIDINE

A mixture of 1-(2-fluoro-3-pyridin-4-ylphenyl)ethanone (1.28 g, 5.95 mmol), ethylene glycol (1.66 ml, 29.75 mmol), molecular sieves (5 g, 3 Å) and p-toluenesulfonic acid monohydrate (0.11 g, 0.59 mmol) in toluene (20 ml) was heated at reflux for 2 h. The molecular sieves was filtered off and the residue was evaporated to dryness. Purification by flash column chromatography (ethyl acetate) gave the title compound (1.0 g). MS m/z (rel. intensity, 70 eV) 259 (M+, 1), 245 (15), 244 (bp), 200 (56), 87 (17).

Preparation 54

1-ETHYL-4-[2-FLUORO-3-(2-METHYL-1,3-DIOXOLAN-2-YL)PHENYL]-1,2,3,6-TETRAHYDROPYRIDINE

Preparation according to preparation 6: 4-[2-fluoro-3-(2-methyl-1,3-dioxolan-2-yl)phenyl]pyridine (0.95 g, 3.66 mmol), 1-iodoethane (4 ml), ethanol (40 ml), sodium borohydride (1.0 g, 29.3 mmol). Yield: 0.88 g. MS m/z (rel. intensity, 70 eV) 291 (M+, bp), 276 (94), 219 (29), 110 (46), 87 (29).

Preparation 55

1-ETHYL-4-[2-FLUORO-3-(2-METHYL-1,3-DIOXOLAN-2-YL)PHENYL]PIPERIDINE

Preparation according to preparation 18: 1-ethyl-4-[2-fluoro-3-(2-methyl-1,3-dioxolan-2-yl)phenyl]-1,2,3,6-tetrahydropyridine (0.73 g, 2.5 mmol), methanol (20 ml), palladium on carbon (0.32 g) and hydrochloric acid (0.2 ml, conc). Yield: 0.7 g. MS m/z (relative intensity, 70 eV) 293 (M+, 23), 292 (12), 279 (15), 278 (bp) 84 (16).

Preparation 56

3-BROMO-2-FLUOROBENZOIC ACID

To a solution of 1-bromo-2-fluorobenzene (6.0 g, 34.3 mmol) in dry tetrahydrofuran (50 ml) under nitrogen, at −78° C. was added lithium diisopropylamide (2.5 M in hexane, 18.8 ml, 37.7 mmol). The mixture was stirred for 50 minutes and then poured onto crushed solid carbon dioxide. The reaction mixture was brought to ambient temperature and aqueous sodium carbonate (10%, 50 ml) was added. The aqueous phase was washed with diethyl ether (2×100 ml), and then made acidic by addition of aqueous hydrochloric acid. The acidified aqueous phase was extracted with ethyl acetate (2×50 ml) and the combined organic phases was dried (MgSO4) and evaporated to dryness to give the title compound (4.24 g).

Preparation 57

3-BROMO-2-FLUOROBENZAMIDE

To a solution of 3-bromo-2-fluorobenzoic acid (3.77 g, 17.2 mmol) in dry tetrahydrofuran (200 ml) was added triethylamine (4.77 ml, 34.4 mmol) and thionyl chloride (1.69 ml, 21.5 mmol). The reaction mixture was stirred for 1 h and then quenched with ammonia in methanol (10 ml, saturated). After an additional hour of stirring the mixture was evaporated and the crude product was purified by flash column chromatography (ethyl acetate/isooctane 1:1) to give the title compound (1.76 g). MS m/z (rel. intensity, 70 eV) 219 (M+, 26), 217 (M+, 26), 203 (62), 201 (70), 94 (bp).

Preparation 58

2-FLUORO-3-PYRIDIN-4-YLBENZAMIDE

Preparation according to preparation 5: 3-bromo-2-fluorobenzamide (1.2 g, 5.5 mmol), toluene (20 ml), ethanol (20 ml), 1-pyridyl-4-boronic acid (0.74 g, 6.05 mmol), sodium carbonate (2.65 g), palladium tetrakis (0.57 g). Yield: 0.47 g. MS m/z (rel. intensity, 70 eV) 216 (M+, 76), 200 (bp), 172 (20), 145 (18), 125 (19).

Preparation 59

3-(1-ETHYL-1,2,3,6-TETRAHYDROPYRIDIN-4-YL)-2-FLUOROBENZAMIDE

Preparation according to preparation 6: 2-fluoro-3-pyridin-4-ylbenzamide (0.94 g, 4.34 mmol), 1-iodoethane (3 ml), ethanol (40 ml), sodium borohydride (1.25 g, 34.8 mmol). Yield: 0.75 g. MS m/z (rel. intensity, 70 eV) 248 (M+, bp), 247 (37), 233 (99), 146 (22), 110 (41).

Preparation 60

3-(1-ETHYLPIPERIDIN-4-YL)-2-FLUOROBENZAMIDE

Preparation according to preparation 18: 3-(1-ethyl-1,2,3,6-tetrahydropyridin-4-yl)-2-fluorobenzamide (0.75 g, 3.0 mmol), methanol (20 ml), palladium on carbon (0.2 g) and hydrochloric acid (0.2 ml, conc.). Yield: 0.57 g. MS m/z (relative intensity, 70 eV) 250 (M+, 48), 249 (26), 236 (34), 235 (bp), 109 (30).

Preparation 61

2-PIPERIDIN-4-YL-6-(TRIFLUOROMETHYL) PHENOL

Preparation according to Example 29: 4-[2-methoxy-3-(trifluoromethyl)phenyl]piperidine (0.07 g, 0.27 mmol), pyridine hydrochloride (0.4 g). Yield: 0.05 g. MS m/z (relative intensity, 70 eV) 245 (M+, bp), 226 (21), 167 (25), 140 (15), 56 (42).

Preparation 62

1-[2-FLUORO-3-(METHYLTHIO)PHENYL] PERAZINE

Preparation according to preparation 22: 1-bromo-2-fluoro-3-(methylthio)benzene (2.15 g, 9.7 mmol), toluene (50 ml), piperazine (4.19 g, 48.5 mmol), potassium tert-butoxide (1.31 g, 13.6 mmol), bis(dibenzylideneacetone)palladium(0) (0.27 g, 0.064 mmol) and (+/−)-1,1'-binaphthyl-2,2'-diyl hydrogen phosphate (0.18 g, 0.064 mmol). Yield: 1.25 g. MS m/z (rel. intensity, 70 eV) 226 (M+, 20), 191 (12), 185 (10), 184 (bp), 168 (15).

Preparation 63

METHYL 4-[2-FLUORO-3-(METHYLTHIO)PHENYL]PIPERAZINE-1-CARBOXYLATE

Preparation according to preparation 26: 1-[2-fluoro-3-(methylthio)phenyl]piperazine (1.25 g, 5.53 mmol), triethylamine (1.2 ml, 7.2 mmol), methylen chloride (50 ml), methyl chloroformate (0.49 g, 6.6 mmol). Yield: 1.56 g. MS m/z (rel. intensity, 70 eV) 284 (M+, 99), 196 (bp), 184 (44), 169 (54), 56 (60).

Preparation 64

METHYL 4-[2-FLUORO-3-(METHYLSULFONYL)PHENYL]PIPERAZINE-1-CARBOXYLATE

To an ice cooled solution of methyl 4-[2-fluoro-3-(methylthio)phenyl]piperazine-1-carboxylate (1.4 g, 4.9 mmol) in sulfuric acid (1 M, 10 ml) was added sodium tungstate (0.016 g, 0.05 mmol) in one portion followed by droppwise addition of hydroperoxide (30%, 1.25 ml, 12.2 mmol). The reaction mixture was warmed to 55° C. and was stirred for 20 h. The reaction mixture was brought to ambient temperature and aqueous sodium hydroxide (5 M, 50 ml) was added. The aqueous phase was extracted with ethyl acetate (2×50 ml). The combined organic phase was dried (MgSO4) and evaporated to dryness to give the title compound. Yield (1.1 g). MS m/z (rel. intensity, 70 eV) 316 (M+, 58), 296 (30), 228 (bp), 216 (38), 56 (71).

Preparation 65

1-[2-FLUORO-3-(METHYLSULFONYL)PHENYL]PIPERAZINE

Preparation according to preparation 29: methyl 4-[2-fluoro-3-(methylsulfonyl)phenyl]piperazine-1-carboxylate (1.0 g, 3.16 mmol) in ethanol (8 ml), hydrochloric acid (6 M, 20 ml). Yield: 0.34 g. MS m/z (rel. intensity, 70 eV) 258 (M+, 17), 215 (13), 216 (bp), 209 (6), 137 (9).

Preparation 66

4-[2-METHOXY-3-(TRIFLUOROMETHOXY) PHENYL]PIPERIDINE

Preparation according to preparation 34: 4-[2-fluoro-3-(trifluoromethoxy)phenyl]piperidine (1.23 g, 4.7 mmol), N,N-dimethylformamide (20 ml), sodium methoxide in methanol (30%, 2.35 ml, 13.2 mmol). Yield: 1.32 g.

Preparation 67

2-PIPERIDIN-4-YL-6-(TRIFLUOROMETHOXY) PHENOL

Preparation according to Example 29: 4-[2-methoxy-3-(trifluoromethoxy)phenyl]piperidine (1.31 g, 4.7 mmol), pyridine hydrochloride (4 g). Yield: 0.5 g. MS m/z (relative intensity, 70 eV) 261 (M+, bp), 260 (31), 244 (11), 215 (6), 56 (93).

Preparation 68

1-(2-FLUORO-3-PIPERIDIN-4-YLPHENYL) ETHANONE

Preparation according to preparation 9: 1-(2-fluoro-3-pyridin-4-ylphenyl)ethanone (0.2 g, 0.93 mmol), hydrochloric acid (0.05 ml, conc.) methanol (5 ml), platinum oxide (0.02 g). Yield: 0.2 g. MS m/z (relative intensity, 70 eV) 221 (M+, 25), 220 (37), 178 (96), 149 (41) 101 (20).

Preparation 69

1-(3-BROMO-2-FLUOROPHENYL)-2,2,2-TRIFLUOROETHANONE

To a solution of 1-bromo-2-fluorobenzene (5.0 g, 28.6 mmol) in dry tetrahydrofuran (50 ml) under nitrogen, at −78° C. was added lithium diisopropylamide (2.0 M in hexane, 15.7 ml, 31.4 mmol). The mixture was stirred for 5 minutes after which ethyl trifluoroacetate (3.76 ml, 31.4 mmol) was added and the stirring was continued at −78° C. for an additional hour. The reaction mixture was brought to ambient temperature and water (50 ml) was added. The phases were separated and the aqueous phase extracted with ethylacetate (3×100 ml). The combined organic phases was dried (MgSO4) and evaporated to dryness to give an oil. The residue was purified by flash column chromatography (isooctane) to give the title compound (2.38 g). MS m/z (relative intensity, 70 eV) 272 (M+, 11), 270 (M+, 11), 203 (97), 201 (bp, 173 (46).

Preparation 70

2,2,2-TRIFLUORO-1-(2-FLUORO-3-PYRIDIN-4-YLPHENYL)ETHANONE

Preparation according to preparation 5: 1-(3-bromo-2-fluorophenyl)-2,2,2-trifluoro-ethanone (2.38 g, 8.78 mmol), toluene (40 ml), ethanol (40 ml), 1-pyridyl-4-boronic acid (1.43 g, 10.5 mmol), sodium carbonate (2.0 g), palladium tetrakis (1.38 g, 0.88 mmol). Yield: 1.36 g. MS m/z (rel. intensity, 70 eV) 269 (M+, 43), 200 (bp), 172 (22), 145 (18), 125 (22).

Preparation 71

2,2,2-TRIFLUORO-1-(2-FLUORO-3-PIPERIDIN-4-YLPHENYL)ETHANONE

Preparation according to preparation 9: 2,2,2-trifluoro-1-(2-fluoro-3-pyridin-4-ylphenyl)ethanone (1.26 g, 4.68 mmol), hydrochloric acid (0.2 ml, conc), methanol (20 ml), platinum oxide (0.12 g). Yield: 0.98 g. MS m/z (relative intensity, 70 eV) 275 (M+, 94), 274 (66), 149 (23), 101 (25) 56 (bp).

Preparation 72

2,2,2-TRIFLUORO-1-(2-FLUORO-3-PIPERIDIN-4-YLPHENYL)ETHANOL 2,2,2-trifluoro-1-(2-fluoro-3-piperidin-4-ylphenyl)ethanone (0.045 g, 0.16 mmol) was dissolved in ethanol (10 ml) and sodium borohydride (0.026 g, 0.064 mmol) was added. The resulting mixture was stirred for 24 h, after which aqueous sodium carbonate (10%, 20 ml) was added. The aqueous phase was extracted with ethylacetate (3×20 ml) and the combined organic phases was dried (MgSO$_4$), filtered and evaporated to dryness. Yield: 0.03 g. MS m/z (rel. intensity, 70 eV) 277 (M+, 87), 276 (69), 178 (14), 103 (19), 56 (bp).

Preparation 73

2-FLUORO-3-PIPERIDIN-4-YLPHENYL METHANESULFONATE 3-(1-ethylpiperidin-4-yl)-2-fluorophenyl methanesulfonate (0.020 g, 0.033 mmol) was dissolved in dry 1,2-dichloroethane (5 ml) and α-chloroethylchloroformat (0.014 ml, 0.033 mmol) was added. The resulting mixture was refluxed for 1 h, and the solvent was evaporated. MS m/z (rel. intensity, 70 eV) 273 (M+, 2), 195 (11), 194 (bp), 178 (5), 56 (60).

Preparation 74

1-ETHYL-4-[2-FLUORO-3-(METHYLTHIO)PHENYL]PIPERIDIN-4-OL

Preparation according to preparation 1 with the exception that n-hexyllitium was used instead of n-butyllithium: 1-bromo-2-fluoro-3-(methylthio)benzene (15 g, 67.8 mmol), dry tetrahydrofurane (70 ml), n-hexyllithium (2.3 M in hexane, 31 ml, 71 mmol), 1-ethylpiperidin-4-one (9.06 g, 71 mmol). Yield: 20.7 g. MS m/z (rel. intensity, 70 eV) 269 (M+, 49), 254 (bp), 236 (36), 56 (31), 84 (23).

Preparation 75

1-ETHYL-4-[2-FLUORO-3-(METHYLTHIO)PHENYL]-1,2,3,6-TETRAHYDROPYRIDINE

A mixture of 1-ethyl-4-[2-fluoro-3-(methylthio)phenyl] piperidin-4-ol (42 g, 156 mmol), sulphuric acid (conc, 8.5 ml) and toluene (200 ml) was heated in a Dean-Stark trap for 20 h. The mixture was cooled to 70° C., water (200 ml) was added and the phases were separated. The aqueous phase was basified with aqueous sodium hydroxide (5 M) and extracted with ethyl acetate (2×50 ml). The combined organic phases was dried (MgSO$_4$) and evaporated to dryness to give the title compound (22.6 g). MS m/z (rel. intensity, 70 eV) 251 (M+, bp), 236 (85), 147 (65), 146 (45), 110 (44).

Preparation 76

1-ETHYL-4-[2-FLUORO-3-(METHYLSULFONYL)PHENYL]-1,2,3,6-TETRAHYDROPYRIDINE

Preparation according to preparation 64: 1-ethyl-4-[2-fluoro-3-(methylthio)phenyl]-1,2,3,6-tetrahydropyridine (22.5 g, 89.6 mmol), sulfuric acid (1 M, 180 ml), sodium tungstate (0.296 g, 0.89 mmol), hydrogen peroxide (30%, 22.9 ml, 224 mmol). Flash column chromatography (ethyl acetate/methanol, 1:1) gave the title compound (17.2 g). MS m/z (rel. intensity, 70 eV) 283 (M+, 63), 268 (bp), 146 (51), 110 (87), 56 (59).

Preparation 77

1-ETHYL-4-[2-FLUORO-3-(METHYLSULFINYL) PHENYL]-1,2,3,6-TETRAHYDROPYRIDINE

Flash column chromatography (ethyl acetate/methanol, 1:1) of the reaction mixture from preparation 76 gave the title compound (150 mg). MS m/z (rel. intensity, 70 eV) 267 (M+, bp), 252 (87), 237 (74), 146 (43), 110 (43).

Preparation 78

4-[2-FLUORO-3-(TRIFLUOROMETHYL)PHENYL]-1-PROPYL-1,2,3,6-TETRAHYDROPYRIDINE

A solution of 4-[2-fluoro-3-(trifluoromethyl)phenyl]-1-propylpiperidin-4-ol (8.0 g, 26 mmol) in trifluoroacetic acid (80 ml) was heated at reflux for 20 h. The mixture was poured on to ice and was basified with 10 M sodium hydroxide. The mixture was extracted with ethylacetate (3×100 ml) and the combined organic phases was dried (MgSO$_4$), filtered and evaporated to dryness. The residue was purified by flash column chromatography (ethylacetate/methanol, 1:1) to give the title compound (5.6 g). MS m/z (rel. intensity, 70 eV) 287 (M+, 22), 259 (16), 258 (bp), 177 (10), 147 (10).

Preparation 79

4-[2-FLUORO-3-(TRIFLUOROMETHYL)PHENYL]-1-PROPYLPIPERIDIN-4-OL

To a solution of 3-Bromo-2-fluorobenzotrifluoride (9.0 g, 37 mmol) in dry tetrahydrofuran (100 ml), under nitrogen, was added dropwise at −78° C., n-butyllithium (2.5 M in hexane, 16.2 ml, 40.5 mmol). The mixture was stirred for 1 h after which a solution of newly distilled 4-propyl-1-piperidone (5.2 g, 37 mmol) in dry tetrahydrofuran (50 ml) was added dropwise. The resulting mixture was stirred at −78° C. for 30 min and then brought to ambient temperature. Water (100 ml) was added and the mixture was extracted with ethylacetate (3×100 ml). The combined organic phases was dried (MgSO$_4$), filtered and evaporated to dryness. The oily residue was purified by flash column chromatography (ethylacetate/methanol, 1:1) to give the title compound (8.0 g). MS m/z (rel. intensity, 70 eV) 305 (M+, 5), 276 (bp), 258 (35), 191 (21), 185 (17).

The following tests were used for evaluation of the compounds according to the invention.

In Vivo Test: Behaviour

Behavioural activity was measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB DIO-24, National Instruments, USA). Each activity monitor consisted of a quadratic metal frame (W×L=40 cm×40 cm) equipped with photobeam sensors. During measurements of behavioural activity, a rat was put in a transparent acrylic cage (W×L×H, 40×40×30 cm) which in turn was placed in the activity monitor. Each activity monitor was equipped with three rows of infrared photobeam sensors, each row consisting of 16 sensors. Two rows were placed along the front and the side of the floor of the cage, at a 90° angle, and the third row was placed 10 cm above the floor to measure vertical activity. Photobeam sensors were spaced 2.5 cm apart. Each activity monitor was fitted in an identical sound and light attenuating box containing a weak house light and a fan.

The computer software was written using object oriented programming (LabVIEW®, National instruments, Austin, Tex., USA).

Behavioural data from each activity monitor, representing the position (horizontal center of gravity and vertical activity) of the animal at each time, were recorded at a sampling frequency of 25 Hz and collected using a custom written LABView™ application. The data from each recording session were stored and analyzed with respect to distance traveled. Each behavioural recording session lasted 60 min, starting approximately 4 min after the injection of test compound. Similar behavioural recording procedures were applied for drug-naïve and drug pre-treated rats. Rats pre-treated with d-amphetamine were given a dose of 1.5 mg/kg i.p. 10 min before the recording session in the activity monitor. Rats pre-treated with MK-801 were given a dose of 0.7 mg/kg i.p. 90 min before the recording session in the activity monitor. The results are presented as counts/60 minutes, or counts/30 minutes, in arbitrary length units. Statistical comparisons were carried out using Student's t-test against the control group. In MK-801 or amphetamine pre-treated animals, statistical comparisons were made against the MK801 or d-amphetamine controls, respectively.

$ED_{50}$ values for reduction of amphetamine-induced hyperlocomotion are calculated by curve fitting. For most compounds, the evaluation is based on 16 amphetamine pre-treated animals over the dose range 0, 11, 33 and 100 μmmol/kg s.c. in one single experiment, with complementary doses in separate experiments. Calculations are based on distance during the last 45 minutes of one hour of measurement. The distances are normalised to amphetamine-control and fitted by least square minimization to the function "End-(End-Control)/(1+(dose/$ED^{50}$)$^{Slope}$)". The four parameters are fitted with the restrictions: $ED_{50}>0$, $0.5<Slope<3$, $End>0\%$ of control. To estimate confidence levels for the parameters, the fit is repeated 100 times with a random evenly distributed squared weight (0 to 1) for every measurement value. Presented $ED_{50}$-ranges cover 95% of these values.

In Vivo Test: Neurochemistry

After the behavioural activity sessions, the rats were decapitated and their brains rapidly taken out and put on an ice-cold petri-dish. The limbic forebrain, the striatum, the frontal cortex and the remaining hemispheral parts of each rat were dissected and frozen. Each brain part was subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 □m, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, MeOH 9% (v/v), MeCN 10.5% v/v), decane sulfonic acid 0.45 mM, and EDTA 0.1 mM. Detection potentials relative to Ag/AgCl reference are 0.45 and 0.65V.

$ED_{50}$ values for the increase of DOPAC in striatum are calculated by curve fitting. For most compounds, the evaluation is based on 20 animals over the dose range 0, 3.7, 11, 33 and 100 mmol/kg s.c. in one single experiment. The DOPAC levels are normalised to control and fitted by least square minimization to the function "End-(End-Control)/(1+(dose/$ED_{50}$)$^{Slope}$)". The four parameters are fitted with the restrictions: $ED_{50}>0$, $0.5<Slope<3$, $350<End<400$ or $End=200\%$ of control (see table 1). To estimate confidence levels for the parameters, the fit is repeated 100 times with a random evenly distributed squared weight (0 to 1) for every measurement value. Presented $ED_{50}$-ranges cover 95% of these values.

In Vivo Test: Oral Bioavailability

Experiments are performed 24 hours after implantation of arterial and venous catheters. Test compound is administered orally at 12.5 μmmol/kg or intravenously at 5 μmmol/kg using the venous catheters, n=3 per group. Arterial blood samples are then taken during six hours at 0, 3, 9, 27, 60, 120, 180, 240, 300 and, 360 minutes after administration of the test compound. The oral bioavailability was calculated as the ratio of the AUC (Area under curve) obtained after oral administration over the AUC obtained after intravenous administration for each rat. The parameter AUC was calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling was performed with a HP ChemStation rev.A.06.03. system. Instrument settings:MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: Zorbax eclipse XDB-C8 (4.6*150 mm, 5 μm) at 20° C. The mobile phase was acetic acid (0.03%) (solvent A) and acetonitrile (solvent B). The flow rate of the mobile phase was 0.8 ml/min. The elution was starting at 12% of solvent β isocratic for 4.5 min, then increasing linearity to 60% over 4.5 min.

Extractions procedure: Plasma samples (0.25-0.5 ml) were diluted with water to 1 ml, and 60 pmol (100 µl) internal standard (–)-OSU6241 was added. The pH was adjusted to 11 by the addition of 25 µl saturated $Na_2CO_3$. After mixing, the samples were extracted with 4 ml dichloromethane by shaking for 20 min. The organic layer was after centrifugation transferred to a smaller tube and evaporated to dryness under a stream of nitrogen. The residue was then dissolved in 120 µl mobile phase (acetic acid (0.03%): acetonitrile, 95:5) for LC-MS analysis (10 µl injected). The selective ion ($MH^+$) was monitored for each Example, and $MH^+$ 296 for (–)-OSU6241 ((3-[3-(ethylsulfonyl)phenyl]-1-propylpiperidine).

A standard curve over the range of 1-500 pmol is prepared by adding appropriate amounts of test compound to blank plasma samples.

In Vitro Test: Metabolic Stability in Rat Liver Microsomes

Rat liver microsomes were isolated as described by Förlin (1980) Tox Appl Pharm. 54(3) 420-430, with minor modifications e.g. 3 mL/g liver of a 0.1 M $Na/K*PO_4$ buffer with 0.15M KCl, pH 7.4, (buffer 1) was added before homogenisation, the homogenate was centrifuged for 20 minutes instead of 15, the supernatant was ultracentrifuged at 100.000 g instead of 105.000 g and the pellet from the ultracentrifugation was resuspended in 1 mL/g liver of 20% v/v 87% glycerol in buffer 1.

1 L of, 0.2 or 1 mM test substance diluted in water, and 10 µL 20 mg/mL rat liver microsome were mixed with 149 µL 37° C. buffer 1 and the reaction was started by addition of 40 µL 4.1 mg/mL NADPH. After 0 or 15 minutes incubation at 37° C. in a heating block (LAB-LINE, MULTI-BLOK Heater or lab4you, TS-100 Thermo shaker at 700 rpm) the reaction was stopped by addition of 100 µL pure acetonitrile. The protein precipitation was then removed by rejecting the pellet after centrifugation at 10.000 g for 10 minutes (Heraeus, Biofuge fresco) in 4° C. The test compound was analysed using HPLC-MS (Hewlett-Packard 1100MSD Series) with a Zorbax SB-C18 column (2.1*150 mm, 5 µm) using 0.03% formic acid and acetonitrile as mobile phase (gradient) or a Zorbax Eclipse XDB-C18 (3*75 mm, 3.5 µm) using 0.03% acetic acid and acetonitrile as mobile phase (gradient). The 15 min turnover was calculated as the fraction of test compound eliminated after 15 minutes, expressed in percent of 0 min levels, i.e. 100*[conc test compound at 0 min–concentration at 15 min]/conc at 0 min.

Preparation of liver microsomes was performed as described in Förlin (1980). Protocols for incubation with liver microsomes are referred in Crespi et Stresser (2000), and Renwick et al (2001).

REFERENCES

Crespi C L, and DM Stressser (2000). Fluorometric screening for metabolism based drug-drug interactions. J. Pharm. Tox. Meth. 44. 325-331

Förlin L. (1980) Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex. Tox Appl Pharm. 54(3) 420-430

Renwick, A B et al. (2001). Metabolism of 2,5-bis(trifluoromethyl)-7-benzyloxy-4-trifluoromethylcoumarin by human hepatic CYP isoforms: evidence for selectivity towards CYP3A4. Xenobiotica 31(4): 187-204

Calculation of ClogP Values

Calculated octanol/water/partitioning constant values (ClogP values) have been calculated for compounds of the invention, using the Bio-Loom for Windows software, version 1.0 from BioByte Corporation (www.biobyte.com) using SMILES representations of the structures as input. Values of ClogP for selected compounds of the invention are given below (Table 6).

TABLE 6

ClogP for selected compounds of the invention

| Example | ClogP |
|---|---|
| 1 | 2.47 |
| 2 | 1.95 |
| 3 | 3.04 |
| 4 | 2.66 |
| 7 | 4.3 |
| 9 | 4.6 |
| 10 | 3.73 |
| 11 | 4.75 |
| 17 | 1.6 |

Calculation of van der Waals Volumes (V(vdW)) for R1 and R2 Substituents

Each substituent volume has been calculated as the difference between the volume of its monosubstituted phenyl and the volume of benzene [V(vdW)subst=V(vdW)subst-Ph–V(vdW)Ph]. The volume calculations have been performed on geometries derived from energy minimisations using the Merck Molecular Force Field (mmff94) in the 2004.03 release of Chemical Computing Group's (www.chemcomp.com) Molecular Operating Environment (MOE) software. Selected van der Waals volumes are given in Table 7 below.

TABLE 7

Selected calculated van der Waals volumes for functional groups of the invention.

| name | structure | subst_vol | name | structure | subst_vol |
|---|---|---|---|---|---|
| SCN | 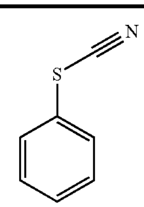 | 39.656255 | COMe | 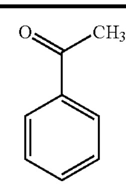 | 35.437505 |

TABLE 7-continued
Selected calculated van der Waals volumes for functional groups of the invention.
| name | structure | subst_vol | name | structure | subst_vol |
|---|---|---|---|---|---|
| OCOMe | 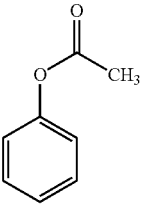 | 43.031255 | COCF3 | 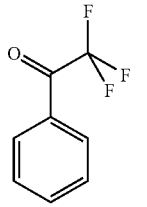 | 43.875005 |
| SCOMe | 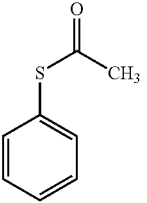 | 51.890625 | OSO2CF3 | 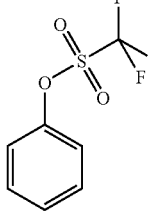 | 62.437505 |
| SCOCF3 | 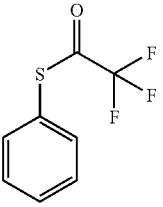 | 64.125005 | OSO2Me | 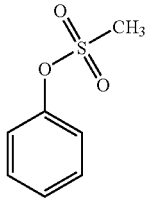 | 55.265625 |
| OCOCF3 | 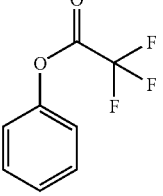 | 52.312505 | CF3 | 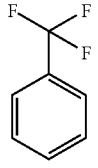 | 27.000005 |
| CH2CN | 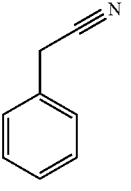 | 32.062505 | OCF3 | 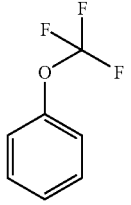 | 32.906255 |
| CH2CF3 | 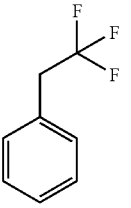 | 41.343755 | OCHF2 | 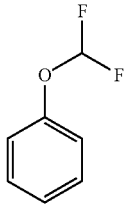 | 30.375005 |

TABLE 7-continued

Selected calculated van der Waals volumes for functional groups of the invention.

| name | structure | subst_vol | name | structure | subst_vol |
| --- | --- | --- | --- | --- | --- |
| CH2SO2Me | 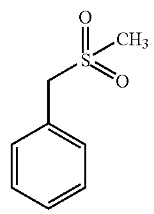 | 59.062505 | CN | 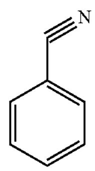 | 18.984375 |
| CH2SO2CF3 | 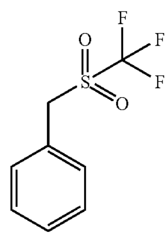 | 72.562505 | F | 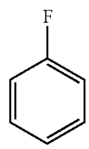 | 2.953125 |
| CH2COMe | 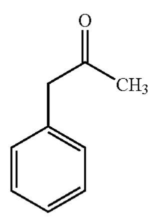 | 48.515625 | Cl | 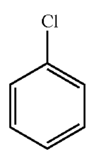 | 15.187505 |
| CH2NO2 | 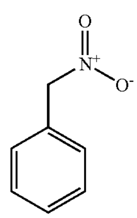 | 35.437505 | SO2NMe2 | 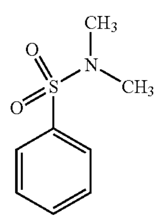 | 76.359375 |
| CH(OH)CF3 | 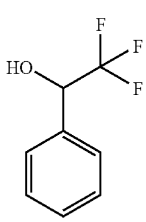 | 47.250005 | OH | 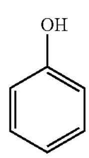 | 3.796875 |
| CH(OH)Me | 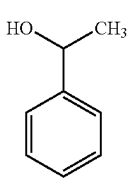 | 38.812505 | OMe | 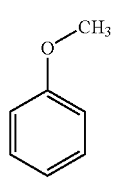 | 22.359375 |

TABLE 7-continued

Selected calculated van der Waals volumes for functional groups of the invention.

| name | structure | subst_vol | name | structure | subst_vol |
|---|---|---|---|---|---|
| NSO2CF3 | 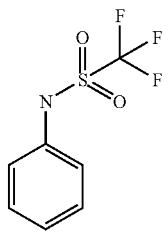 | 64.968755 | Me | CH₃ | 17.718755 |
| NSO2Me | 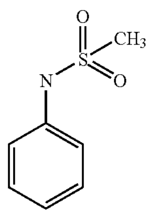 | 51.468755 | NH2 | NH₂ | 9.281255 |
| SO2Me | 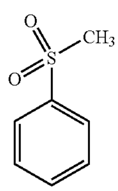 | 44.296875 | SO2NH2 | 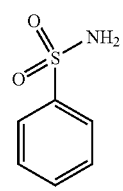 | 37.546875 |
| SO2CF3 | 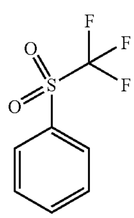 | 53.156255 | SO2CN | 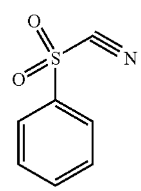 | 42.609375 |
| | | | H | | 0 |

REFERENCES

Crespi C L, and DM Stressser (2000). Fluorometric screening for metabolism based drug-drug interactions. J. Pharm. Tox. Meth. 44. 325-331

Förlin L. (1980) Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex. Tox Appl Pharm. 54(3) 420-430

Renwick, A B et al. (2001). Metabolism of 2,5-bis(trifluoromethyl)-7-benzyloxy-4-trifluoromethylcoumarin by human hepatic CYP isoforms: evidence for selectivity towards CYP3A4. Xenobiotica 31(4): 187-204

Microdialysis

Male Sprague-Dawley rats weighing 220-320 g were used throughout the experiments. Before the experiment the animals were group housed, five animals in each cage, with free access to water and food. The animals were housed at least one week after arrival prior to surgery and use in the experiments. Each rat was used only once for microdialysis.

We use a modified version (Waters, Lofberg et al. 1994) of the I-shaped probe (Santiago and Westerink 1990). The dialysis membrane we use is the AN69 polyacrylonitrile/sodiummethalylsulfonate copolymer (HOSPAL; o.d./i.d. 310/220 µm: Gambro, Lund, Sweden). In the dorsal striatum we use probes with an exposed length of 3 mm of dialysis membrane and in the prefrontal cortex the corresponding length is 2.5 mm. The rats were operated under isoflurane inhalationanesthesia while mounted into a Kopf stereotaxic instrument. Co-ordinates were calculated relative to bregma; dorsal striatum AP +1, ML ±2.6, DV −6.3; Pf cortex, AP +3.2, 8° ML ±1.2, DV −4.0 according to (Paxinos and Watson 1986). The dialysis probe was positioned in a burr hole under stereotaxic guidance and cemented with phosphatine dental cement.

The rats were housed individually in cages for 48 h before the dialysis experiments, allowing them to recover from surgery and minimizing the risk of drug interactions with the anaesthetic during the following experiments. During this period the rats had free access to food and water. On the day of experiment the rats were connected to a micro perfusion pump via a swiwel and were replaced in the cage where they could move freely within its confinements. The perfusion medium was a Ringer's solution containing in mmol/l: NaCl; 140, CaCl2; 1.2, KCl; 3.0, MgCl2; 1.0 and ascorbic acid; 0.04 according to (Moghaddam and Bunney 1989). The pump was set to a perfusion speed of 2 μl/min and 40 μl samples were collected every 20 min.

30 μl of each sample was injected into the chromatograph. On a 10-port injector (Valco C10W), with two sample loops mounted in series (2 μl and 20 μl), each brain dialysate sample is loaded in both loops simultaneously. When the valve is switched to inject the main part of the 20 μl sample is introduced into a reverse-phase ion-pairing system for dopamine (DA), norepinephrine (NA), normetanephrine (NM), 3-methoxytyramine(3-MT) and serotonin (5-hydroxytryptamine, 5-HT) determination (large loop), while a small fraction (2 μl, from the small loop) is introduced on a reverse-phase column for the chromatography of the acidic monoamine metabolites 3,4-di-hydroxyphenylacetic acid (DOPAC), homovanillic acid (HVA) and 5-hydroxyindoleacetic acid (5-HIAA). The currents generated by the two EC detectors are converted to digital data and evaluated using Chromelion software (Dionex, Sunnyvale, Calif.) on a PC. The method sample turn over time was 4.5 min and two parallel experiments are normally analysed simultaneously on the system. After the experiment the rats were uncoupled from the perfusion pump and decapitated. Their brains were rapidly taken out and fixed in Neo-fix solution (Kebo-lab, Sweden) for subsequent inspection of probe localisation. The Animal Ethics Committee in Göteborg, Sweden approved the procedures applied in these experiments.

Moghaddam, B. and B. S. Bunney (1989). "Ionic Composition of Microdialysis Perfusing Solution Alters the Pharmacological Responsiveness and Basal Outflow of Striatal Dopamine." J. Neurochem. 53: 652-654.

Paxinos, G. and C. Watson (1986). The Rat Brain in Stereotaxic Coordinates. New York, Academic Press.

Santiago, M. and B. H. C. Westerink (1990). "Characterization of the in vivo release of dopamine as recorded by different types of intracerebral microdialysis probes." Naunyn-Schmiedeberg's Arch. Pharmacol. 342: 407-414.

Waters, N., L. Lofberg, S. Haadsma-Svensson, K. Svensson, C. Sonesson and A. Carlsson (1994). "Differential effects of dopamine D2 and D3 receptor antagonists in regard to dopamine release, in vivo receptor displacement and behaviour." J Neural Transm Gen Sect 98(1): 39-55.

The invention claimed is:

1. A compound being
1-ethyl-4-[2-fluoro-3-(methylsulfonyl)phenyl]piperidine; or a pharmaceutically acceptable salt thereof.

2. A pharmaceutical composition comprising a compound of Formula 1:

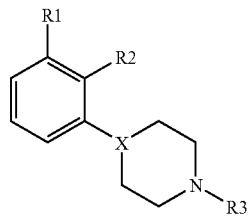

(1)

wherein:
X is CH;
R₁ is SO₂CH₃;
R₂ is F; and R₃ is ethyl; or a pharmaceutically acceptable salt thereof;

and one or more pharmaceutically acceptable carriers or diluents.

3. A method for treating movement disorders selected from the group, consisting of Parkinson's disease, Parkinsonism, dyskinesias, dystonias, tics, tremor, and Hundington's disease, said method comprising the administration of a therapeutically active amount of a compound according to claim 1 to a mammal, suffering from such a disorder.

4. A method for treating movement disorders according to claim 3, wherein the movement disorder is L-Dopa induced dyskinesias.

* * * * *